(12) United States Patent
Taniguchi et al.

(10) Patent No.: US 10,344,093 B2
(45) Date of Patent: Jul. 9, 2019

(54) ANTIBODY GENE EXPRESSION-SECRETION SYSTEM

(71) Applicant: SHINSHU UNIVERSITY, Nagano (JP)

(72) Inventors: Shun-ichiro Taniguchi, Nagano (JP); Yasuto Akiyama, Shizuoka (JP); Takeshi Masaki, Nagano (JP); Hitomi Shimizu, Nagano (JP)

(73) Assignee: Shinshu University, Nagano (JP)

( * ) Notice: Subject to any disclaimer, the term of this patent is extended or adjusted under 35 U.S.C. 154(b) by 0 days.

(21) Appl. No.: 15/308,452

(22) PCT Filed: Apr. 17, 2015

(86) PCT No.: PCT/JP2015/002133
§ 371 (c)(1),
(2) Date: Nov. 2, 2016

(87) PCT Pub. No.: WO2015/166641
PCT Pub. Date: Nov. 5, 2015

(65) Prior Publication Data
US 2017/0218072 A1 Aug. 3, 2017

(30) Foreign Application Priority Data
May 2, 2014 (JP) .................... 2014-095440

(51) Int. Cl.
| | | |
|---|---|---|
| *C07K 16/32* | (2006.01) | |
| *C07K 16/28* | (2006.01) | |
| *A61K 39/395* | (2006.01) | |
| *A61K 35/74* | (2015.01) | |
| *C12N 15/00* | (2006.01) | |
| *C12N 15/09* | (2006.01) | |
| *C12P 21/00* | (2006.01) | |

(52) U.S. Cl.
CPC .......... *C07K 16/2863* (2013.01); *A61K 35/74* (2013.01); *A61K 39/395* (2013.01); *C07K 16/32* (2013.01); *C12N 15/00* (2013.01); *C12N 15/09* (2013.01); *C12P 21/005* (2013.01); *C07K 2317/24* (2013.01); *C07K 2317/622* (2013.01); *C07K 2317/73* (2013.01); *C07K 2317/92* (2013.01); *C07K 2319/02* (2013.01)

(58) Field of Classification Search
None
See application file for complete search history.

(56) References Cited

U.S. PATENT DOCUMENTS

2017/0183667 A1  6/2017  Koseki et al.

FOREIGN PATENT DOCUMENTS

| EP | 1227152 | 7/2002 |
|---|---|---|
| JP | 2006-180708 | 7/2006 |
| JP | 2010-035472 | 2/2010 |
| JP | 2011-087586 | 5/2011 |
| WO | 2001/062907 | 8/2001 |
| WO | 2011/093465 | 8/2011 |
| WO | 2011/093467 | 8/2011 |
| WO | 2011/093468 | 8/2011 |
| WO | 2013/065869 | 5/2013 |

OTHER PUBLICATIONS

Deng, Qiwen, "Signal peptide of Arabinosidase enhances secretion of interferon-α2b protein by Bifidobacteria longum" *Archives of Microbiology*, Sep. 1, 2009, v. 191, No. 9, pp. 681-686.
Schell, Mark A., "The genome sequence of Bifidobacterium longum reflects its adaptation to the human gastrointestinal tract" *Proc Natl Acad Sci USA*, Oct. 29, 2002, v. 99, No. 22, pp. 14422-14427.
International Preliminary Report for corresponding PCT/JP2015/002133, dated Nov. 17, 2016.
Shinji Fukuda et al. "Bifidobacteria can protect from enteropathogenic infection through production of acetate," Nature, vol. 469, No. 7331, Jan. 27, 2011, pp. 543-547.
Zhijian Yu et al. "Bifidobacteria as an Oral Delivery Carrier of Interleukin-12 for the Treatment of Coxsackie virus B3-induced myocarditis in the Balb/c mice," International Immunopharmacology, vol. 12, No. 1, Oct. 31, 2011 pp. 125-130.
Extended European Search Report, European Application No. 15786443.0, dated Oct. 5, 2017 (6 pages).

*Primary Examiner* — Jana A Hines
*Assistant Examiner* — Khatol S Shahnan Shah
(74) *Attorney, Agent, or Firm* — Occhiuti & Rohlicek LLP

(57) ABSTRACT

It is an object of the present invention to provide signal sequence information capable of secreting an antibody to the outside of cells in generation of the antibody by microorganisms of genus *Bifidobacterium*, and an antibody expression vector capable of secreting an antibody to the outside of cells by utilizing the signal sequence information. As a means for achieving the aforementioned object, there is prepared *Bifidobacterium longum*, which is transformed with a vector having inserted thereinto a DNA insert comprising the 5'-terminus of an antibody gene linked to the 3'-terminus of a DNA encoding a signal peptide-linker conjugate having a linker linked to the C-terminus of a signal peptide consisting of an amino acid sequence shown in SEQ ID NO: 1.

9 Claims, 16 Drawing Sheets
Specification includes a Sequence Listing.

[Figure 1]
Structure of Trastuzumab scFv secretion plasmid
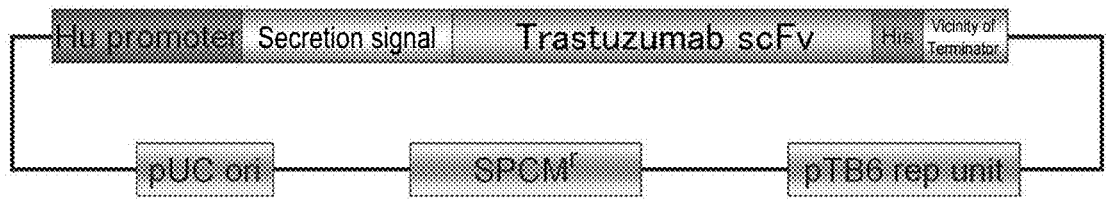
Vector framework: pBEshuttle (having SPCM$^r$ and replication origins of E. coli and bifidobacteria)

[Figure 2]

Total nucleotide sequence of Trastuzumab scFv antibody

Trastuzumab-scFv-His :

```
  1 ATGGAAGTTC AGCTGGTTGA AAGCGGTGGC GGTCTGGTTC AGCCTGGTGG
 51 TAGCCTGCGT CTGAGCTGTG CAGCAAGCGG TTTTAACATT AAAGATACCT
101 ATATTCATTG GGTGCGTCAG GCACCGGGTA AAGGTCTGGA ATGGGTTGCA
151 CGTATTTATC CGACCAATGG TTATACCCGT TATGCCGATA GCGTTAAAGG
201 TCGTTTTACC ATTAGCGCAG ATACCAGCAA AAATACCGCA TATCTGCAGA
251 TGAATAGCCT GCGTGCAGAG GATACCGCAG TGTATTATTG TAGCCGTTGG
301 GGTGGTGATG GTTTTTATGC AATGGATTAT TGGGGTCAGG GCACCCTGGT
351 TACCGTTAGC AGTGGTGGTG GTGGTAGCGG TGGTGGGGGT TCAGGTGGTG
401 GTGGATCCGA TATTCAGATG ACCCAGAGCC CGAGCAGCCT GAGCGCAAGC
451 GTTGGTGATC GTGTTACCAT TACCTGTCGT GCAAGCCAGG ATGTTAATAC
501 CGCAGTTGCA TGGTATCAGC AGAAACCGGG TAAAGCACCG AAACTGCTGA
551 TTTATAGCGC AAGCTTTCTG TATAGCGGTG TTCCGAGCCG TTTTAGCGGT
601 AGCCGTAGCG GCACCGATTT TACCCTGACC ATTAGCAGCC TGCAGCCGGA
651 AGATTTTGCA ACCTATTATT GTCAGCAGCA TTACACCACC CCTCCGACCT
701 TTGGTCAGGG CACCAAAGTT GAAATTAAAC ATCATCATCA CCATCATTAA
```

|  |  |  |
|---|---|---|
| 1~750 : | Trastuzumab-scFv-His | SEQ ID NO: 5 |
| 1~363 : | Trastuzumab-scFv VH | SEQ ID NO: 6 |
| (292~331 : | CDR3-1) | SEQ ID NO: 7 |
| 364~408 : | Trastuzumab-scFv linker | SEQ ID NO: 8 |
| 409~729 : | Trastuzumab-scFv VK | SEQ ID NO: 9 |
| (673~699 : | CDR3-2) | SEQ ID NO: 10 |
| 730~747 : | 6xHis-tag | SEQ ID NO: 11 |

[Figure 3]
Plasmid SP1B-9
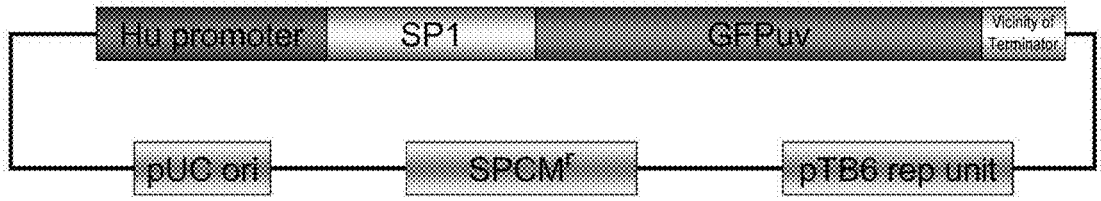
[Figure 4]
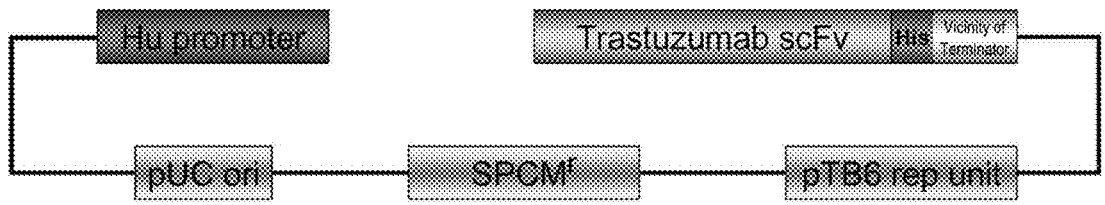
[Figure 5]
Trastuzumab scFv structure in recombinant bifidobacteria detected by Western blot analysis
HuSP27L0: SP (52aa) | scFv (249aa)
HuSP27L6: SP (52aa) Linker(6aa) | scFv (249aa)
HuSP3L22: SP (33aa) Linker(22aa) | scFv (249aa)
Size of Trastuzumab scFv body: approximately 25 kDa

[Figure 6]
Trastuzumab scFv expression in bifidobacteria (Western blot analysis)
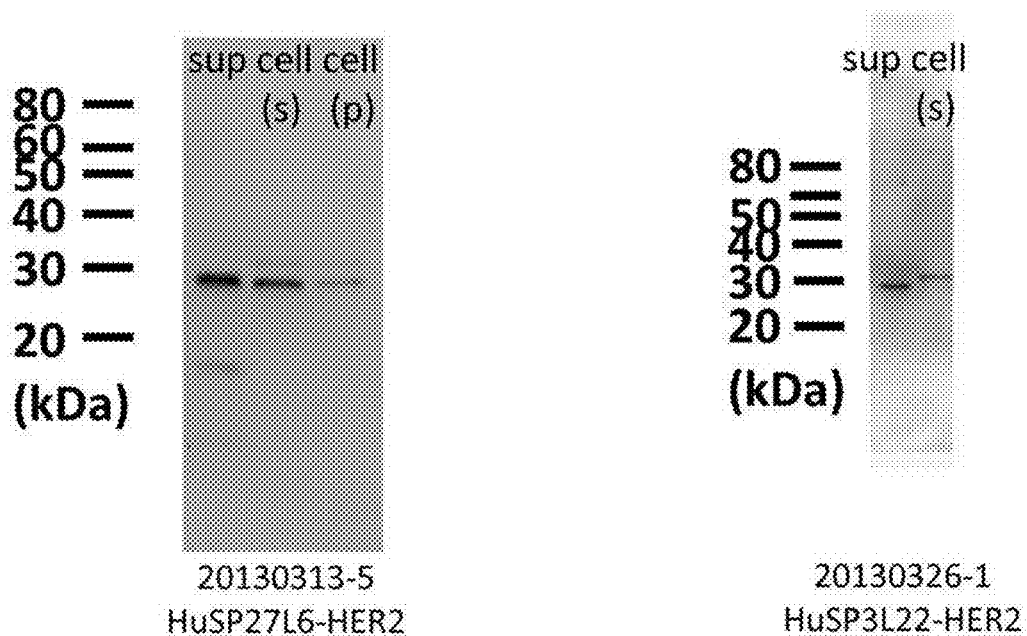
Sup: bifidobacteria culture supernatant in 500 µL of culture solution
Cell-s: bifidobacteria soluble fraction in 2.5 µL of culture solution
Cell-p: bifidobacteria insoluble fraction in 25 µL of culture solution
Detected using histidine tag at C-terminus as indicator

[Figure 7]
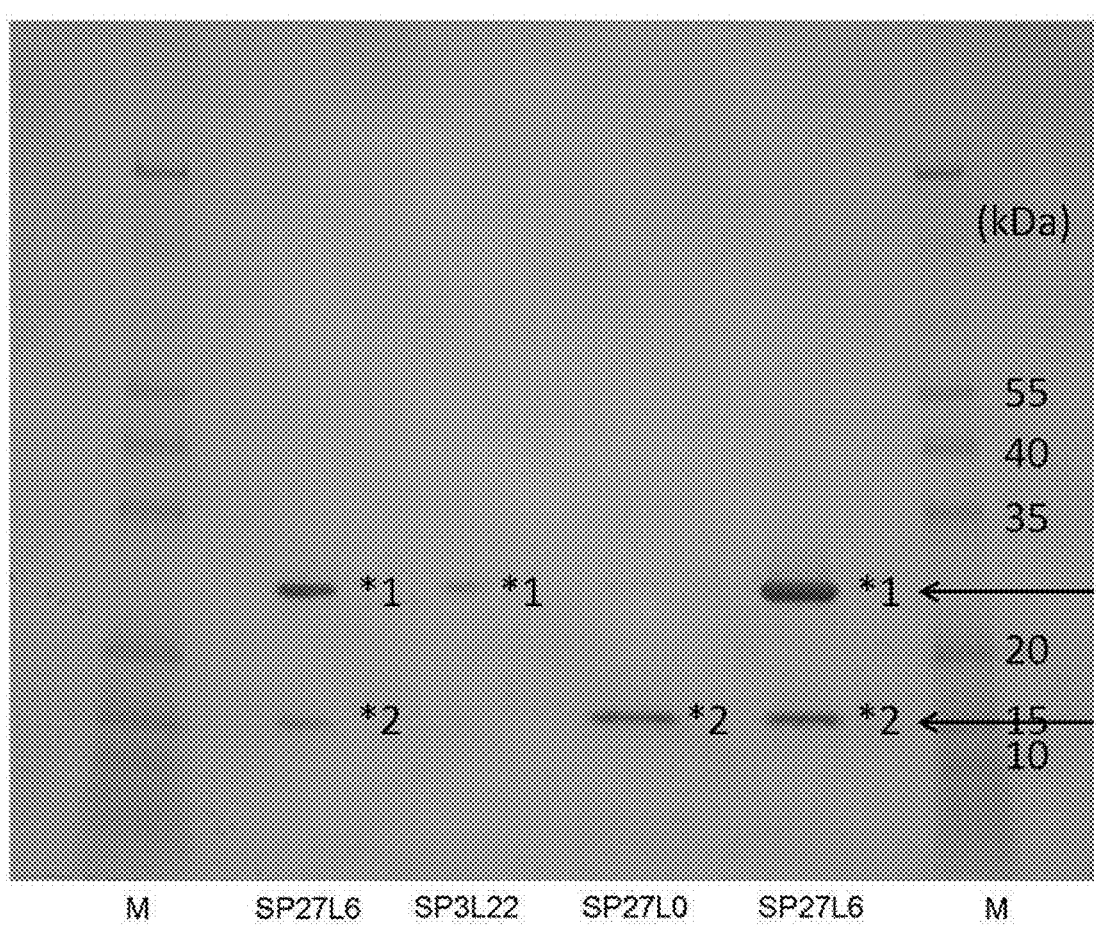

[Figure 8]

Analysis results of His-Tag-purified protein by LC-MS/MS

SP27L6-Trastuzumab scFv(1) (Coverage 39%) Band 1
SEQ ID NO: 111

SP27L6-Trastuzumab scFv(1) (Coverage 17%) Band 2
SEQ ID NO: 111

SP27L6-Trastuzumab scFv(2) (Coverage 50%)
Band 1
SEQ ID NO: 111

SP27L0-Trastuzumab scFv (coverage 17%)
Band 2
SEQ ID NO: 112

SP3L22-Trastuzumab scFv (coverage 44%)
Band 1
SEQ ID NO: 113

----- Signal sequence     ----- Linker sequence

[Figure 9]

Peptide fragments matched with Trastuzumab scFv amino acid sequence by LC-MS/MS analysis 1) TEVQLVESGGGLVQPGGSLR          SEQ ID NO: 114
2) LSCAASGFNIKDTYIHWVR           SEQ ID NO: 115
3) GLEWVARIYPTNGYTR              SEQ ID NO: 116
4) NTAYLQMNSLR                   SEQ ID NO: 117
5) WGGDGFYAMDYWGQGTLVTVSSGGGGSGGGGSGGGGSDIQMTQSPSSLSASVGDR
                                 SEQ ID NO: 118
6) VTITCRASQDVNTAVAWYQQKPGK      SEQ ID NO: 119
7) LLIYSASFLYSGVPSR              SEQ ID NO: 120

[Figure 10]

Construction of Trastuzumab scFv secretion vector and expression of Trastuzumab scFv in E. coli

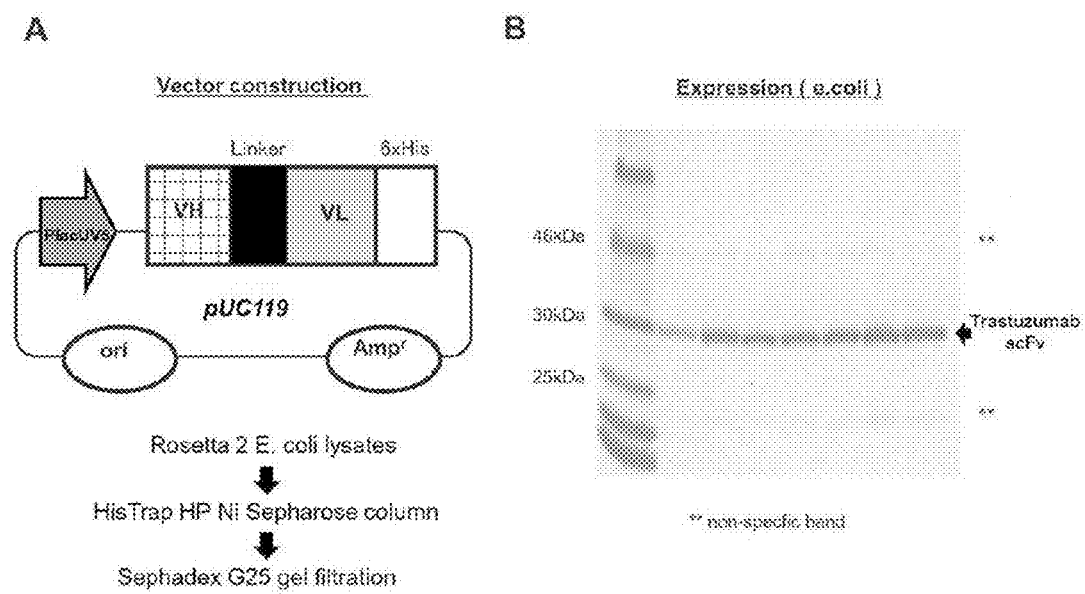

[Figure 11]
Measurement of affinity of Trastuzumab scFv with HER2 extracellular domain by Biacore X100
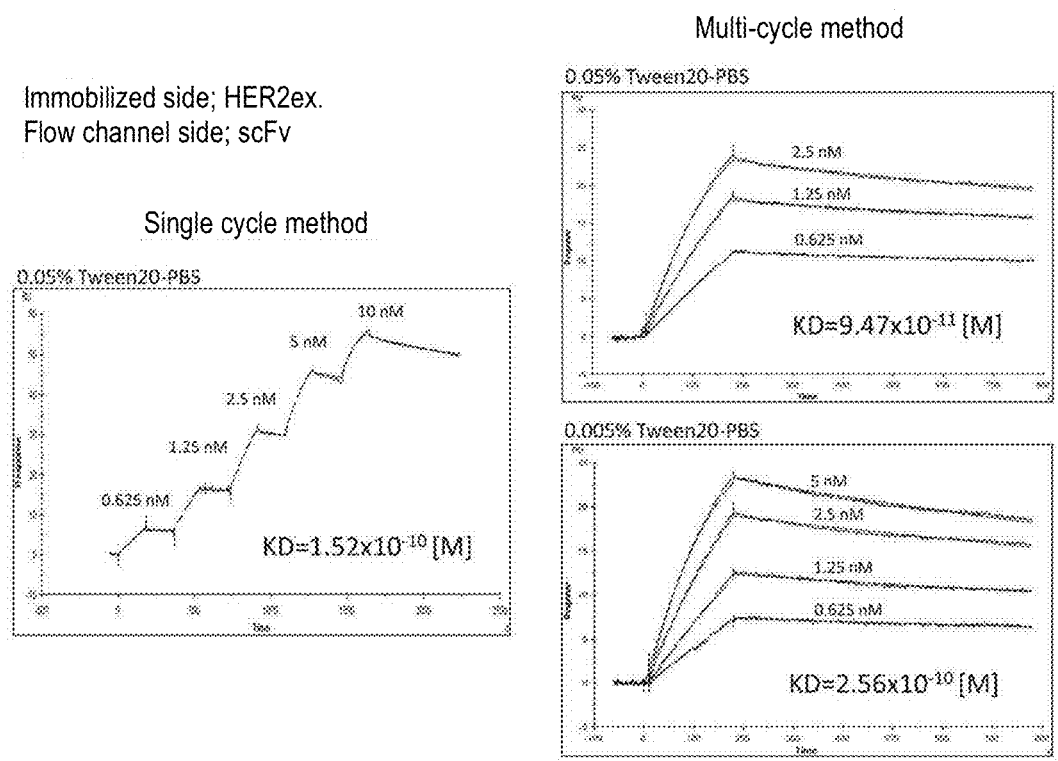

[Figure 12]
Measurement of affinity of Trastuzumab full-body antibody with HER2 extracellular domain by Biacore X100
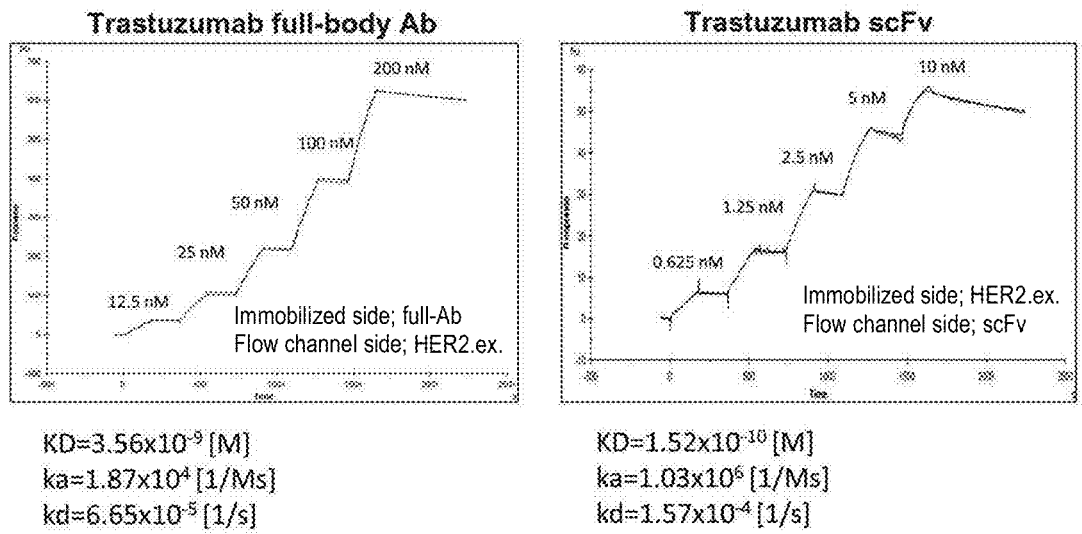
[Figure 13]
FACS analysis of binding ability of Trastuzumab scFv and Trastuzumab full-body antibody to human breast cancer cell lines
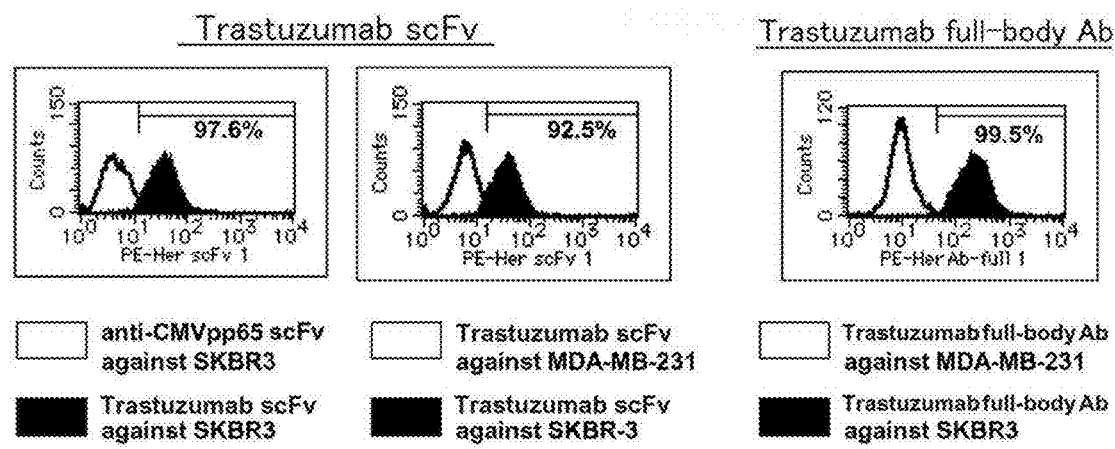

[Figure 14]
In vivo dynamic imaging of Cy5.5-labeled Trastuzumab scFv using
in vivo tumor models
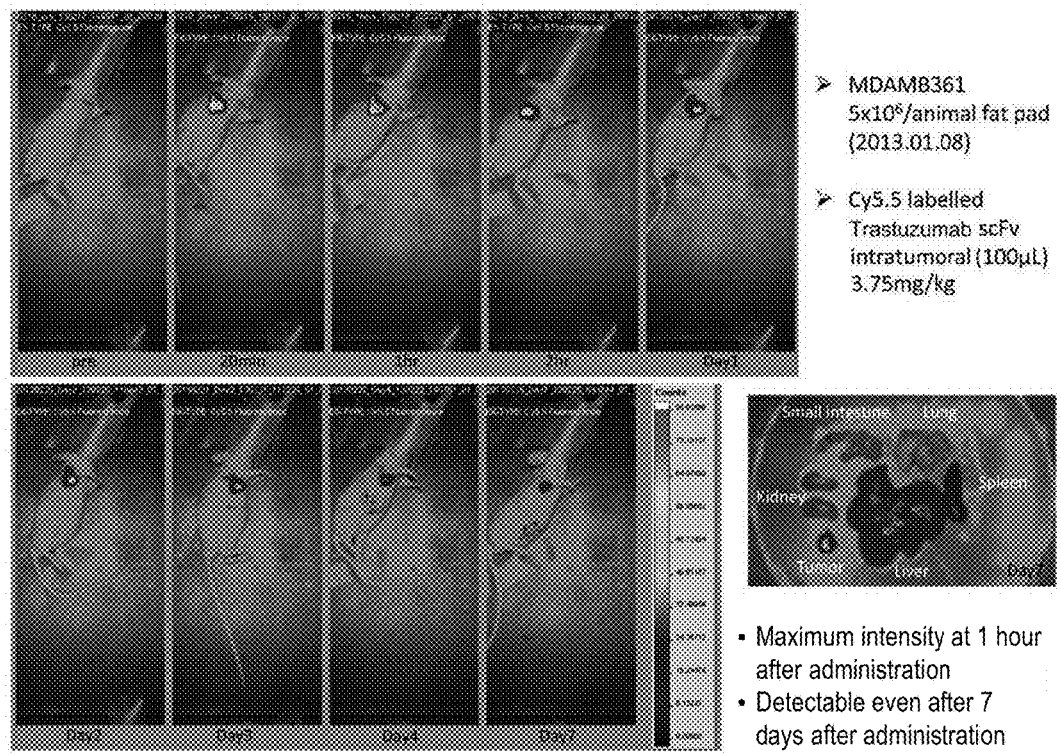

[Figure 15]

In vivo dynamic imaging of Cy5.5-labeled Trastuzumab full-body Ab using in vivo tumor models

- Animals after transplantation of 4 x 10⁶ MDA-MB-361 used
- Intratumoral administration of Cy5.5-labeled Trastuzumab full-body antibody (in amount corresponding to 3.75 mg/kg) (Day 56)
- After administration, imaging over time until 20 min, 1 hr, 3 hr, Day 1, Day 2, and Day 5

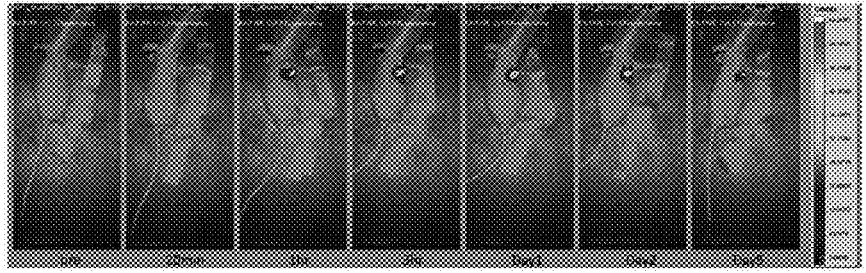

MDA-MB-361  0.1mL it

[Figure 16]

Inhibiting effect of Trastuzumab scFv on growth of orthotropic grafted tumor of human breast cancer MDA-MB-361 cells

MDA-MB-361 1x10⁶ cells (contain Matrigel)/mouse, female BALB/cA-*nu/nu* mice, fad pad (n=4-5)
Trastuzumab scFv 3.75mg/kg (injection volume 50μL/it) x 4 (Days 0, 2, 4, 7, 9)

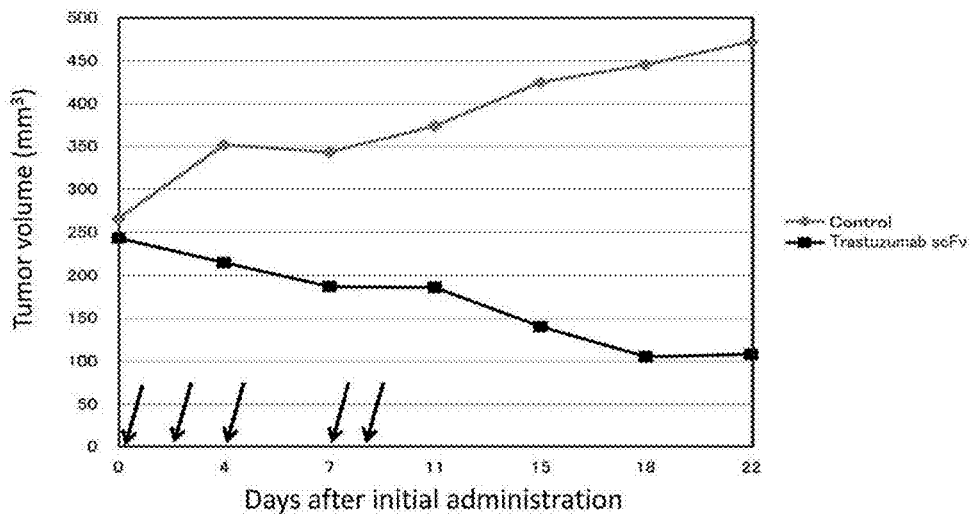

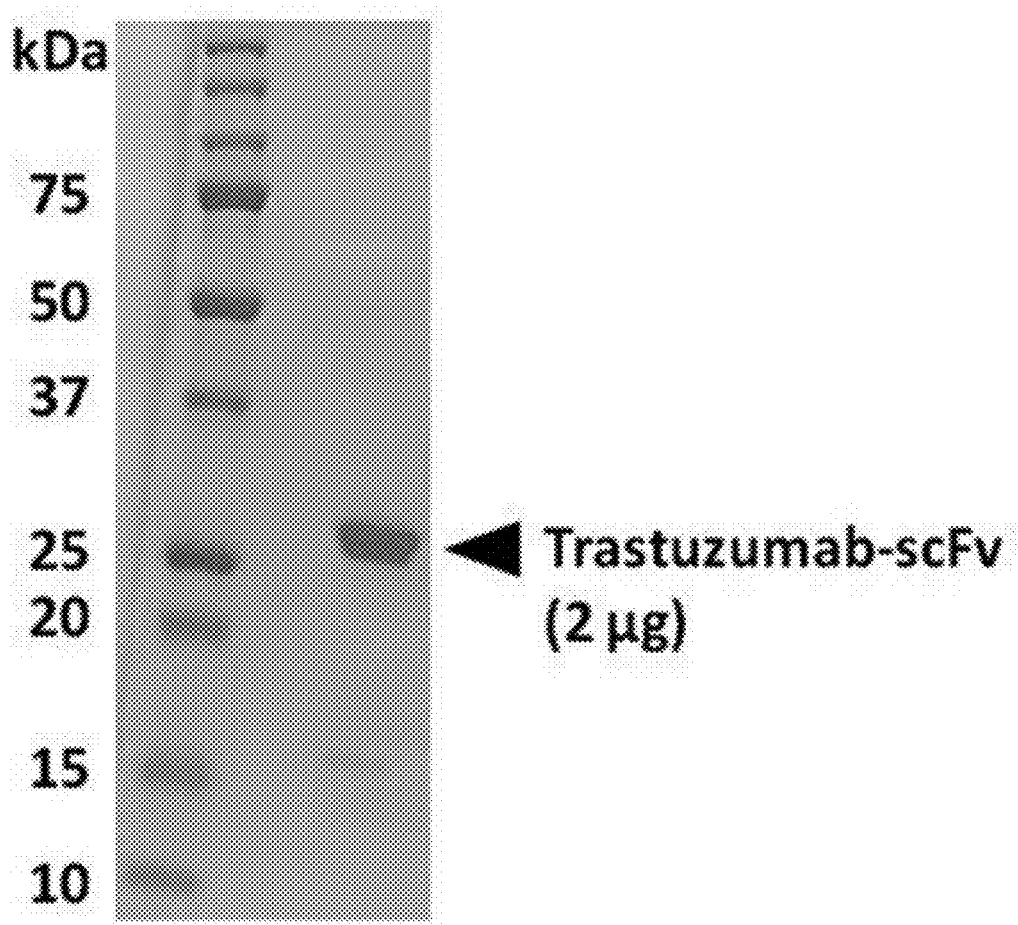
[Figure 17]

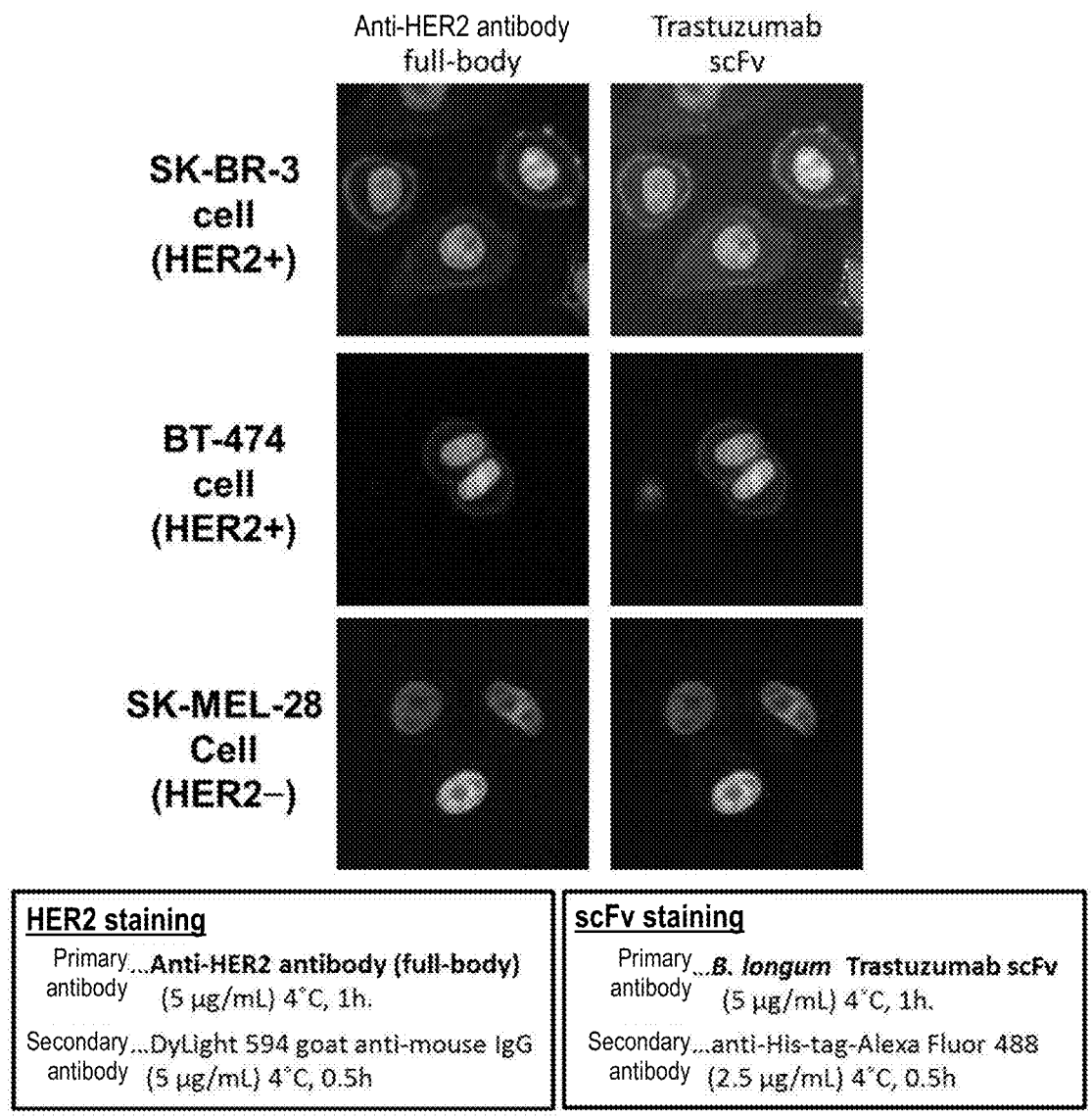
[Figure 18]

[Figure 19]
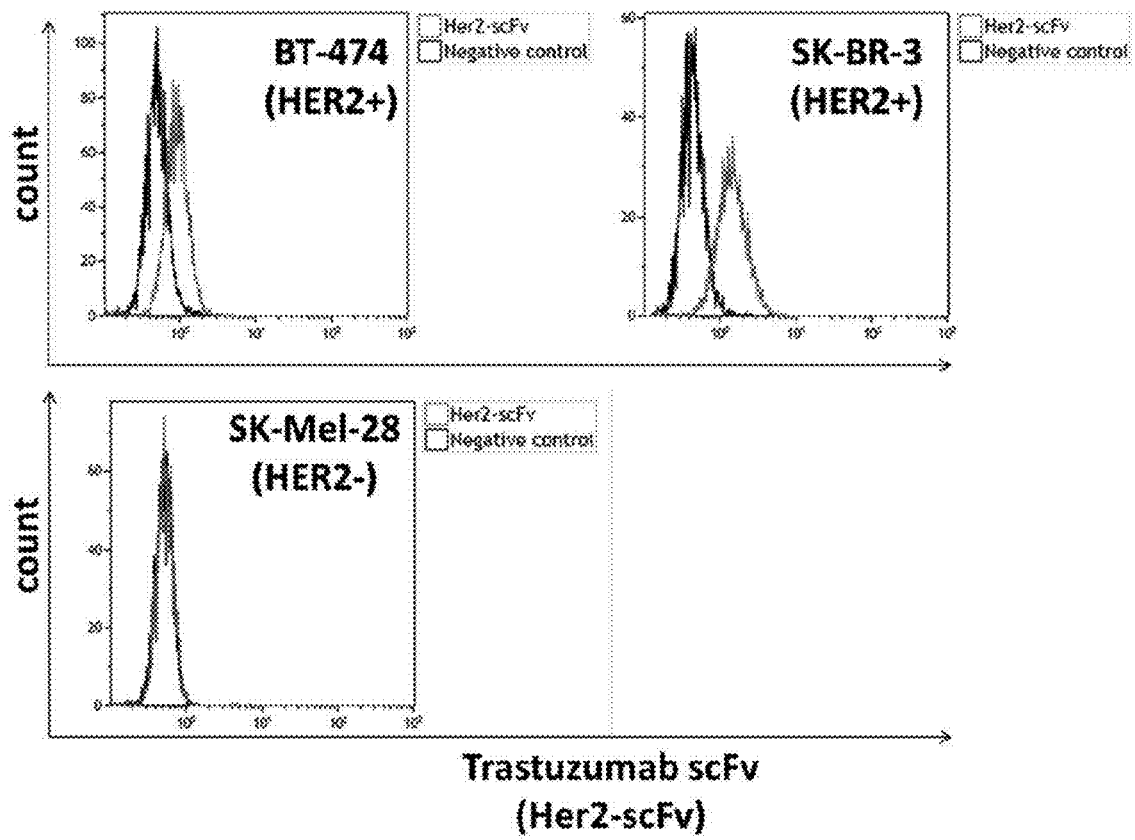
[Figure 20]
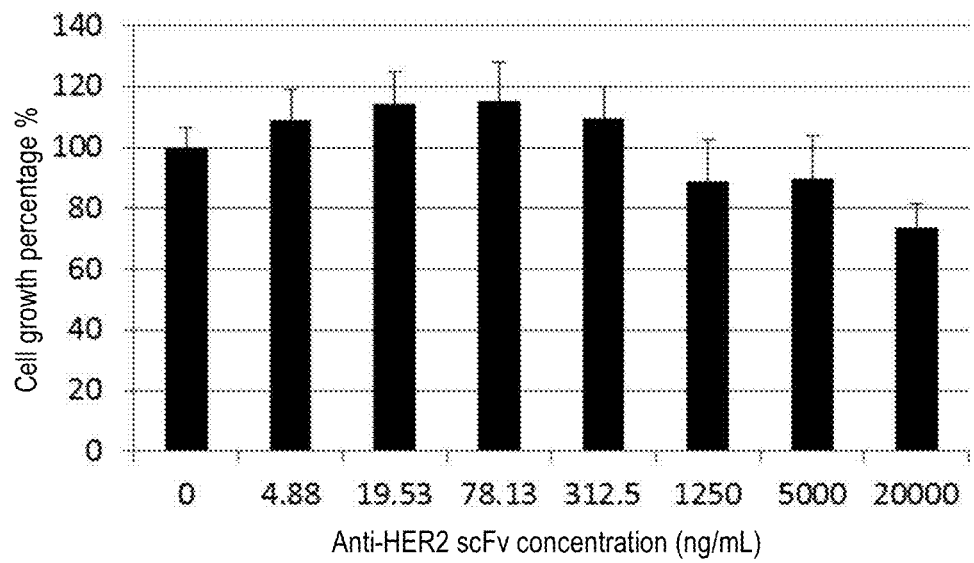

[Figure 21]
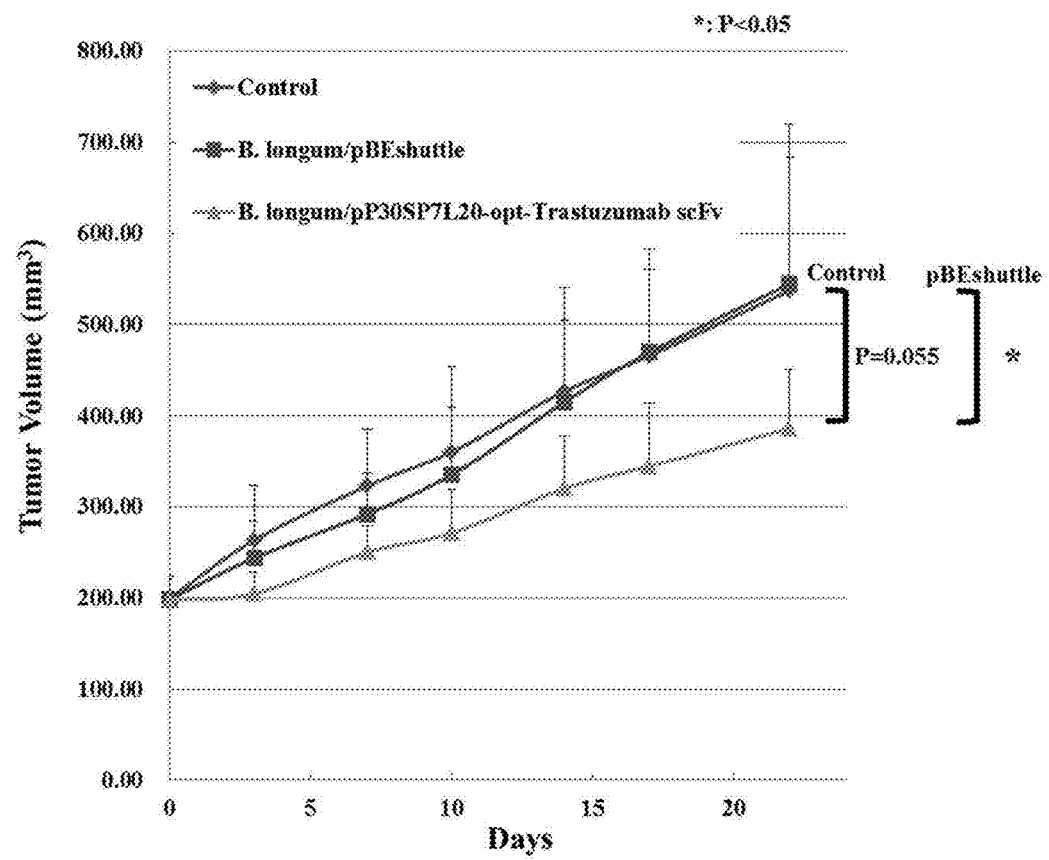
[Figure 22]
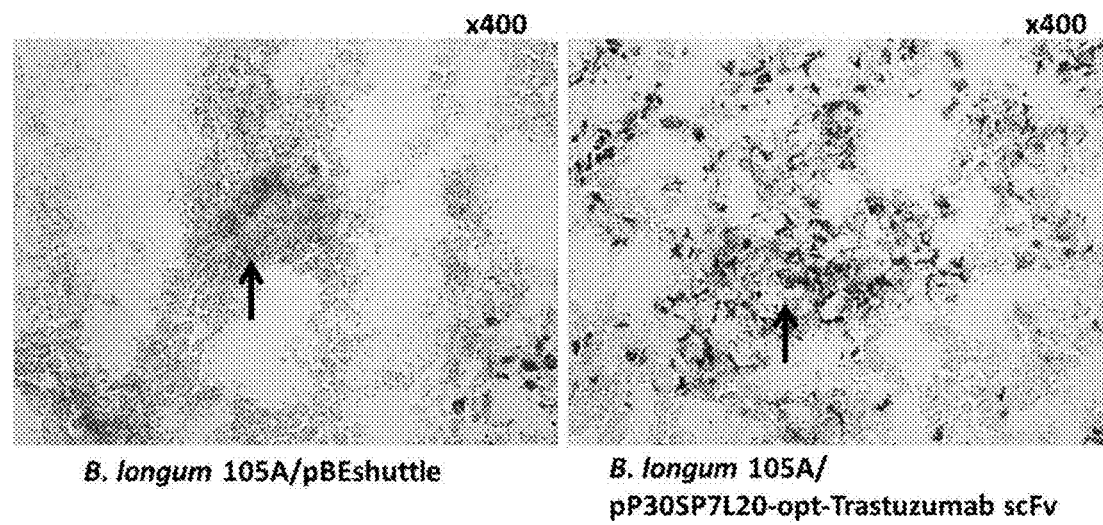
*B. longum* 105A/pBEshuttle
*B. longum* 105A/pP30SP7L20-opt-Trastuzumab scFv

[Figure 23]
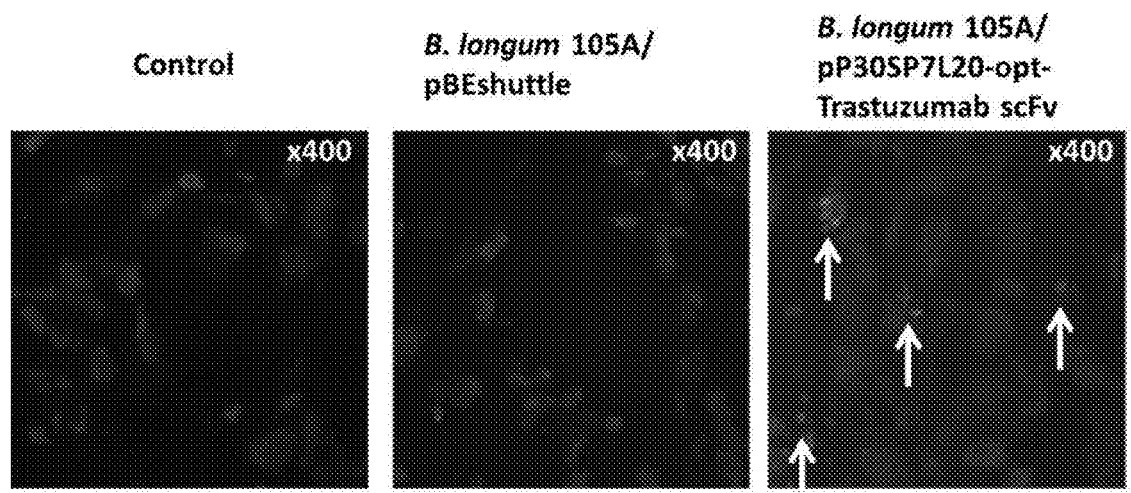

SEQUENCE LISTING

<160> NUMBER OF SEQ ID NOS: 120

<210> SEQ ID NO 1
<211> LENGTH: 52
<212> TYPE: PRT
<213> ORGANISM: Artificial
<220> FEATURE:
<223> OTHER INFORMATION: signal peptide 27
<220> FEATURE:
<221> NAME/KEY: misc_feature
<223> OTHER INFORMATION: Inventor: TANIGUCHI, Shun-ichiro; AKIYAMA,
      Yasuto; MASAKI Takeshi; SHIMIZU Hitomi

<400> SEQUENCE: 1

Met Asn Thr Ile Arg Arg Ile Val Glu Phe Ala Lys Val Lys Thr Phe
1               5                   10                  15

Ala Phe Lys Cys Ile Ala Ile Gly Ala Ala Leu Ala Leu Val Ala Ser
            20                  25                  30

Ala Cys Val Ile Gln Leu Ala Ser Thr Gln Leu Ile Gly Gly Arg Gln
        35                  40                  45

Thr Ala Gln Ala
    50

<210> SEQ ID NO 2
<211> LENGTH: 156
<212> TYPE: DNA
<213> ORGANISM: Artificial
<220> FEATURE:
<223> OTHER INFORMATION: SP27

<400> SEQUENCE: 2
atgaacacca ttcgtcgcat cgtagagttc gccaaggtca agaccttcgc gttcaaatgc      60
atcgccatcg gcgccgcatt ggcgttggtg gcgtcggcat gcgtgattca gctggcctcc     120
acccagctca tcggcggccg tcaaaccgca caagcg                               156

<210> SEQ ID NO 3
<211> LENGTH: 58
<212> TYPE: PRT
<213> ORGANISM: Artificial
<220> FEATURE:
<223> OTHER INFORMATION: signal peptide 27 Linker 6/SP27L6

<400> SEQUENCE: 3

Met Asn Thr Ile Arg Arg Ile Val Glu Phe Ala Lys Val Lys Thr Phe
1               5                   10                  15

Ala Phe Lys Cys Ile Ala Ile Gly Ala Ala Leu Ala Leu Val Ala Ser
            20                  25                  30

Ala Cys Val Ile Gln Leu Ala Ser Thr Gln Leu Ile Gly Gly Arg Gln
        35                  40                  45

Thr Ala Gln Ala Ala Thr Ala Asn Arg Thr
    50                  55

<210> SEQ ID NO 4
<211> LENGTH: 174
<212> TYPE: DNA
<213> ORGANISM: Artificial
<220> FEATURE:
<223> OTHER INFORMATION: SP27L6

<400> SEQUENCE: 4
atgaacacca ttcgtcgcat cgtagagttc gccaaggtca agaccttcgc gttcaaatgc      60
atcgccatcg gcgccgcatt ggcgttggtg gcgtcggcat gcgtgattca gctggcctcc     120
acccagctca tcggcggccg tcaaaccgca caagcggcca cggctaaccg cacc    174

<210> SEQ ID NO 5
<211> LENGTH: 750
<212> TYPE: DNA
<213> ORGANISM: Artificial
<220> FEATURE:
<223> OTHER INFORMATION: Trastuzumab-scFv-His

<400> SEQUENCE: 5
atggaagttc agctggttga aagcggtggc ggtctggttc agcctggtgg tagcctgcgt    60
ctgagctgtg cagcaagcgg ttttaacatt aaagatacct atattcattg ggtgcgtcag    120
gcaccgggta aggtctgga atgggttgca cgtatttatc cgaccaatgg ttataccgt    180
tatgccgata gcgttaaagg tcgttttacc attagcgcag ataccagcaa aaataccgca    240
tatctgcaga tgaatagcct gcgtgcagag gataccgcag tgtattattg tagccgttgg    300
ggtggtgatg gttttatgc aatggattat tggggtcagg gcaccctggt taccgttagc    360
agtggtggtg gtggtagcgg tggtgggggt tcaggtggtg gtggatccga tattcagatg    420
acccagagcc cgagcagcct gagcgcaagc gttggtgatc gtgttaccat tacctgtcgt    480
gcaagccagg atgttaatac cgcagttgca tggtatcagc agaaaccggg taaagcaccg    540
aaactgctga tttatagcgc aagctttctg tatagcggtg ttccgagccg ttttagcggt    600
agccgtagcg gcaccgattt taccctgacc attagcagcc tgcagccgga agattttgca    660
acctattatt gtcagcagca ttacaccacc cctccgacct ttggtcaggg caccaaagtt    720
gaaattaaac atcatcatca ccatcattaa    750

<210> SEQ ID NO 6
<211> LENGTH: 363
<212> TYPE: DNA
<213> ORGANISM: Artificial
<220> FEATURE:
<223> OTHER INFORMATION: Trastuzumab-scFv VH

<400> SEQUENCE: 6
atggaagttc agctggttga aagcggtggc ggtctggttc agcctggtgg tagcctgcgt    60
ctgagctgtg cagcaagcgg ttttaacatt aaagatacct atattcattg ggtgcgtcag    120
gcaccgggta aggtctgga atgggttgca cgtatttatc cgaccaatgg ttataccgt    180
tatgccgata gcgttaaagg tcgttttacc attagcgcag ataccagcaa aaataccgca    240
tatctgcaga tgaatagcct gcgtgcagag gataccgcag tgtattattg tagccgttgg    300
ggtggtgatg gttttatgc aatggattat tggggtcagg gcaccctggt taccgttagc    360
agt    363

<210> SEQ ID NO 7
<211> LENGTH: 40
<212> TYPE: DNA
<213> ORGANISM: Artificial
<220> FEATURE:
<223> OTHER INFORMATION: CDR3-1

<400> SEQUENCE: 7
agccgttggg gtggtgatgg ttttatgca atggattatt    40

<210> SEQ ID NO 8
<211> LENGTH: 45
<212> TYPE: DNA

<213> ORGANISM: Artificial
<220> FEATURE:
<223> OTHER INFORMATION: Trastuzumab-scFv linker

<400> SEQUENCE: 8

```
ggtggtggtg gtagcggtgg tgggggttca ggtggtggtg gatcc              45
```

<210> SEQ ID NO 9
<211> LENGTH: 321
<212> TYPE: DNA
<213> ORGANISM: Artificial
<220> FEATURE:
<223> OTHER INFORMATION: Trastuzumab-scFv VK

<400> SEQUENCE: 9

```
gatattcaga tgacccagag cccgagcagc ctgagcgcaa gcgttggtga tcgtgttacc      60
attacctgtc gtgcaagcca ggatgttaat accgcagttg catggtatca gcagaaaccg     120
ggtaaagcac cgaaactgct gatttatagc gcaagctttc tgtatagcgg tgttccgagc     180
cgttttagcg gtagccgtag cggcaccgat tttaccctga ccattagcag cctgcagccg     240
gaagattttg caacctatta ttgtcagcag cattacacca cccctccgac ctttggtcag     300
ggcaccaaag ttgaaattaa a                                                321
```

<210> SEQ ID NO 10
<211> LENGTH: 27
<212> TYPE: DNA
<213> ORGANISM: Artificial
<220> FEATURE:
<223> OTHER INFORMATION: CDR3-2

<400> SEQUENCE: 10

```
cagcagcatt acaccacccc tccgacc                                          27
```

<210> SEQ ID NO 11
<211> LENGTH: 18
<212> TYPE: DNA
<213> ORGANISM: Artificial
<220> FEATURE:
<223> OTHER INFORMATION: 6xHis-tag

<400> SEQUENCE: 11

```
catcatcatc accatcat                                                    18
```

<210> SEQ ID NO 12
<211> LENGTH: 21
<212> TYPE: DNA
<213> ORGANISM: Artificial
<220> FEATURE:
<223> OTHER INFORMATION: SP1_Vec_F3

<400> SEQUENCE: 12

```
ccttctgctc gtagcgatta c                                                21
```

<210> SEQ ID NO 13
<211> LENGTH: 17
<212> TYPE: DNA
<213> ORGANISM: Artificial
<220> FEATURE:
<223> OTHER INFORMATION: SP1_Vec_R2

<400> SEQUENCE: 13

```
ttccacgcgc tccttgg                                                     17
```

```
<210> SEQ ID NO 14
<211> LENGTH: 36
<212> TYPE: DNA
<213> ORGANISM: Artificial
<220> FEATURE:
<223> OTHER INFORMATION: Trastuzumab scFv_ins_INF_F3

<400> SEQUENCE: 14
aaggagcgcg tggaagaagt tcagctggtt gaaagc                          36

<210> SEQ ID NO 15
<211> LENGTH: 45
<212> TYPE: DNA
<213> ORGANISM: Artificial
<220> FEATURE:
<223> OTHER INFORMATION: Trastuzumab scFv_ins_INF_R2

<400> SEQUENCE: 15
gctacgagca aaggttaat gatggtgatg atgatgttta atttc                 45

<210> SEQ ID NO 16
<211> LENGTH: 4697
<212> TYPE: DNA
<213> ORGANISM: Artificial
<220> FEATURE:
<223> OTHER INFORMATION: SP1B-9 (pSP1B-9?j

<400> SEQUENCE: 16
ggatccgtct tcctgctggc ctatgcattg ggttccgcag tgcccactcc aggcggtctg    60
ggcggtgtgg aagcggcgct gacattcgcg ttcgtggcgg tcggagtgcc gcagggcgtg   120
gcgctttccg ccactttgct gcaccgcgtg gtgttctact ggctgcgcat tccgctgggc   180
gcggcggcca tgaagtggct tgacaagcat aatcttgtct gattcgtcta ttttcatacc   240
cccttcgggg aaatagatgt gaaaaccctt ataaaacgcg gttttcgca gaaacatgcg    300 ctagtatcat tgatgacaac atggactaag caaaagtgct tgtcccctga cccaagaagg   360
atgctttatg gcggaaaacta ccgttaagcc cacgaagctt gctgttattg gtgccggtgc   420
cgttggctcc accctcgcct cgccgctgc ccagcgtggc atcgctcgcg agatcgtgct    480
tgaagacatc gccaaggagc gcgtggaatc caagggcgag gagctgttca ccggcgtggt   540
gccgatcctg gtggagctgg acggcgacgt gaacggccac aagttctccg tgtccggcga   600
gggcgagggc gacgccacct acggcaagct gaccctgaag ttcatctgca ccaccggcaa   660
gctgccggtg ccgtggccga ccctggtgac caccttctcc tacggcgtgc agtgcttctc   720
ccgctacccg gaccacatga gcgccacga cttcttcaag tccgccatgc cggagggcta    780
cgtgcaggag cgcaccatct ccttcaagga cgacggcaac tacaagaccc gcgccgaggt   840
gaagttcgag ggcgacaccc tggtgaaccg catcgagctg aagggcatcg acttcaagga   900
agacggcaac atcctgggcc acaagctgga gtacaactac aactcccaca cgtgtacat    960 caccgccgac aagcagaaga acggcatcaa ggccaacttc aagatccgcc acaacatcga   1020
ggacggctcc gtgcagctgg ccgaccacta ccagcagaac accccgatcg gcgacggccc   1080
ggtgctgctg ccggacaacc actacctgtc cacccagtcc gccctgtcca aggacccgaa   1140
cgagaagcgc gaccacatgg tgctgctgga gttcgtgacc gccgccggca tcaccacgg   1200 catggacgag ctgtacaagt aaccttctgc tcgtagcgat tacttcgagc attactgacg   1260
acaaagaccc cgaccgagat ggtcgggtc ttttgttgt ggtgctgtga cgtgttgtcc     1320
aaccgtatta ttccggacta gtcctccagg acctcgtcta cgaggcgctg agcgaggaat   1380
```

```
ggcgcaaaag ggacggcgag atcagcgacc catgggccaa cgacgaggcg gacggatacc    1440
agccgccctc atacgagccg gtcaaccccg aacgcaggac tccccagacg ccctccgatg    1500
gcctgatctg acgtccgaaa aaaggcgctg tgcgcccttt ttaaatcttt tataaatctt    1560
tttacattct tttagcccct ccgcagcctt actctcccaa cgggtttcag ccgaaaccta    1620
caccaaaagg ggagcgaacc tacaccaaaa ggggagcgaa cctacaccaa aaggggagcg    1680
aacctcacac aaaaggggag ctatatacac cttttgttat ttaaggtgca agttgtgcta    1740
tgctgaggcc atgtccaatg agatcgtgaa gttcagcaac cagttcaaca acgtcgcgct    1800
gaagaagttc gacgccgtgc acctggacgt gctcatggcg atcgcctcaa gggtgaggga    1860
gaagggcacg gccacggtgg agttctcgtt cgaggagctg cgcggcctca tgcgattgag    1920
gaagaacctg accaacaagc agctggccga caagatcgtg cagacgaacg cgcgcctgct    1980
ggcgctgaac tacatgttcg aggattcggg caagatcatc cagttcgcgc tgttcacgaa    2040
gttcgtcacc gacccgcagg aggcgactct cgcggttggg gtcaacgagg agttcgcgtt    2100
cctgctcaac gacctgacca gccagttcac gcgcttcgag ctggccgagt tcgccgacct    2160
caagagcaag tacgccaagg agttctaccg cagggccaag cagtaccgca gctccggaat    2220
ctggaagatc ggccgcgacg agttctgccg actgcttggc gttccaccgt cggcaataac    2280
ccagacacga tatctgaatc agaaggttct tcagccaatt caggaggagt gtgggcctct    2340
ccttggcctg aagatcgagc gccagtacgt gaaacgcagg ctgtcgggct tcgtgttcac    2400
attcgcccgc gagacccctc cggtgatcga cgccaggccc gtggaggcga ggaagacgga    2460
cggcgacgga aagggccatt ggacgagcgt tgccgggtac ggcgaggtgt tcacgaccac    2520
ggcgttgttc gacgtgacgg ccgcccgggc tcacttcgac ggcaccgttg aagccgggga    2580
gtgccgtttc tgcgcgtttg acgcgcgcaa ccgcgaacat catgcgcgga acgccggaag    2640
gctgttctag cggccgtgtc cgcgcctctg gggcggttgc gcctgccatg ggtcgatctg    2700
ccgctgttcg gcctcacgct ggtctgtgcg ctgcctgatc tccctgagca ggtcggcctt    2760
ggtcctgggg gcgcttcgct cctcgaacgg gccgctctcc cccaggtcct cgggctcgct    2820
caggtccaac ggctcgtcac cggacggctc gggccggttc tctccctgtg ccgggttctc    2880
cgcctgtgcg cgttgttcgg ccatgcgcag tgcgagggcc ttcacctgtt cggggcttgt    2940
cgactcgatt tcgttcgtg aatacatgtt ataataacta taactaataa cgtaacgtga    3000
ctggcaagag atattttaa acaatgaat aggtttacac ttactttagt tttatggaaa    3060
tgaaagatca tatcatatat aatctagaat aaaattaact aaaataatta ttatctagat    3120
aaaaaattta gaagccaatg aaatctataa ataaactaaa ttaagtttat ttaattaaca    3180
actatggata taaataggt actaatcaaa atagtgagga ggatatattt gaatacatac    3240
gaacaaatta ataaagtgaa aaaaatactt cggaaacatt taaaaaataa ccttattggt    3300
acttacatgt ttggatcagg agttgagagt ggactaaaac caaatagtga tcttgacttt    3360
ttagtcgtcg tatctgaacc attgacagat caaagtaaag aaatacttat acaaaaaatt    3420
agacctattt caaaaaaaat aggagataaa agcaacttac gatatattga attaacaatt    3480
attattcagc aagaaatggt accgtggaat catcctccca aacaagaatt tatttatgga    3540
gaatggttac aagagcttta tgaacaagga tacattcctc agaaggaatt aaattcagat    3600
ttaaccataa tgctttacca agcaaaacga aaaaataaaa gaatatacgg aaattatgac    3660
ttagaggaat tactacctga tattccattt tctgatgtga aagagccat tatggattcg    3720
tcagaggaat taatagataa ttatcaggat gatgaaacca actctatatt aactttatgc    3780
```

```
cgtatgattt taactatgga cacgggtaaa atcataccaa aagatattgc gggaaatgca    3840
gtggctgaat cttctccatt agaacatagg gagagaattt tgttagcagt tcgtagttat    3900
cttggagaga atattgaatg gactaatgaa aatgtaaatt taactataaa ctatttaaat    3960
aacagattaa aaaattata aaaaaattga aaaaatggtg gaaacacttt ttcaatttt     4020 tttagatctt gagcaaaagg ccagcaaaag gccaggaacc gtaaaaaggc cgcgttgctg    4080
gcgtttttcc ataggctccg ccccctgac gagcatcaca aaaatcgacg ctcaagtcag    4140
aggtggcgaa acccgacagg actataaaga taccaggcgt ttccccctgg aagctccctc    4200
gtgcgctctc ctgttccgac cctgccgctt accggatacc tgtccgcctt ctcccttcg    4260 ggaagcgtgg cgctttctca tagctcacgc tgtaggtatc tcagttcggt gtaggtcgtt    4320
cgctccaagc tgggctgtgt gcacgaaccc cccgttcagc ccgaccgctg cgccttatcc    4380
ggtaactatc gtcttgagtc aacccggta agacacgact tatcgccact ggcagcagcc    4440
actggtaaca ggattagcag agcgaggtat gtaggcggtg ctacagagtt cttgaagtgg    4500
tggcctaact acggctacac tagaagaaca gtatttggta tctgcgctct gctgaagcca    4560
gttaccttcg gaaaaagagt tggtagctct tgatccggca acaaaccac cgctggtagc    4620 ggtggttttt tgtttgcaa gcagcagatt acgcgcagaa aaaaggatc tcaagaagat    4680 cctttgatct tttctac                                                  4697
```

<210> SEQ ID NO 17
<211> LENGTH: 23
<212> TYPE: DNA
<213> ORGANISM: Artificial
<220> FEATURE:
<223> OTHER INFORMATION: Hu-Trastuzumab_vec_F1

<400> SEQUENCE: 17
gaagttcagc tggttgaaag cgg                                             23

<210> SEQ ID NO 18
<211> LENGTH: 22
<212> TYPE: DNA
<213> ORGANISM: Artificial
<220> FEATURE:
<223> OTHER INFORMATION: Hu-Vec_R1

<400> SEQUENCE: 18
aaagcatcct tcttgggtca gg                                              22

<210> SEQ ID NO 19
<211> LENGTH: 35
<212> TYPE: DNA
<213> ORGANISM: Artificial
<220> FEATURE:
<223> OTHER INFORMATION: SP2B_ins_INF_F1

<400> SEQUENCE: 19
caagaaggat gctttgtggg tatgactgag aacgc                                35

<210> SEQ ID NO 20
<211> LENGTH: 31
<212> TYPE: DNA
<213> ORGANISM: Artificial
<220> FEATURE:
<223> OTHER INFORMATION: SP2B-Trastuzumab_ins_INF_R1

<400> SEQUENCE: 20
aaccagctga acttccaaaa acagcacgcg g           31

<210> SEQ ID NO 21
<211> LENGTH: 37
<212> TYPE: DNA
<213> ORGANISM: Artificial
<220> FEATURE:
<223> OTHER INFORMATION: SP3B_ins_INF_F1

<400> SEQUENCE: 21
caagaaggat gctttatgtt caataagcga cacatcg           37

<210> SEQ ID NO 22
<211> LENGTH: 32
<212> TYPE: DNA
<213> ORGANISM: Artificial
<220> FEATURE:
<223> OTHER INFORMATION: SP3B-Trastuzumab_ins_INF_R1

<400> SEQUENCE: 22
aaccagctga acttcggcga tggtcagctt gc           32

<210> SEQ ID NO 23
<211> LENGTH: 36
<212> TYPE: DNA
<213> ORGANISM: Artificial
<220> FEATURE:
<223> OTHER INFORMATION: SP4B_ins_INF_F1

<400> SEQUENCE: 23
caagaaggat gctttatgac cactcacaac agccag           36

<210> SEQ ID NO 24
<211> LENGTH: 30
<212> TYPE: DNA
<213> ORGANISM: Artificial
<220> FEATURE:
<223> OTHER INFORMATION: SP4B-Trastuzumab_ins_INF_R1

<400> SEQUENCE: 24
aaccagctga acttcgccga acagacgcgg           30

<210> SEQ ID NO 25
<211> LENGTH: 33
<212> TYPE: DNA
<213> ORGANISM: Artificial
<220> FEATURE:
<223> OTHER INFORMATION: SP5B_ins_INF_F1

<400> SEQUENCE: 25
caagaaggat gctttatgac cgcgattgac gag           33

<210> SEQ ID NO 26
<211> LENGTH: 34
<212> TYPE: DNA
<213> ORGANISM: Artificial
<220> FEATURE:
<223> OTHER INFORMATION: SP5B-Trastuzumab_ins_INF_R1

<400> SEQUENCE: 26
aaccagctga acttcttggt cgatgatggc cttg           34

<210> SEQ ID NO 27
<211> LENGTH: 34
<212> TYPE: DNA
<213> ORGANISM: Artificial

<220> FEATURE:
<223> OTHER INFORMATION: SP6B_ins_INF_F1

<400> SEQUENCE: 27
caagaaggat gctttatgaa gattgcggtt gcag      34

<210> SEQ ID NO 28
<211> LENGTH: 40
<212> TYPE: DNA
<213> ORGANISM: Artificial
<220> FEATURE:
<223> OTHER INFORMATION: SP6B-Trastuzumab_ins_INF_R1

<400> SEQUENCE: 28
aaccagctga acttcatcga caataggact tttcccattg      40

<210> SEQ ID NO 29
<211> LENGTH: 33
<212> TYPE: DNA
<213> ORGANISM: Artificial
<220> FEATURE:
<223> OTHER INFORMATION: SP7B_ins_INF_F1

<400> SEQUENCE: 29
caagaaggat gctttatgtt tgcgtgcgta gcc      33

<210> SEQ ID NO 30
<211> LENGTH: 32
<212> TYPE: DNA
<213> ORGANISM: Artificial
<220> FEATURE:
<223> OTHER INFORMATION: SP7B-Trastuzumab_ins_INF_R1

<400> SEQUENCE: 30
aaccagctga acttcggtgg aggtggattc gg      32

<210> SEQ ID NO 31
<211> LENGTH: 34
<212> TYPE: DNA
<213> ORGANISM: Artificial
<220> FEATURE:
<223> OTHER INFORMATION: SP8B_ins_INF_F1

<400> SEQUENCE: 31
caagaaggat gctttatggt tggtgacgac accg      34

<210> SEQ ID NO 32
<211> LENGTH: 30
<212> TYPE: DNA
<213> ORGANISM: Artificial
<220> FEATURE:
<223> OTHER INFORMATION: SP8B-Trastuzumab_ins_INF_R1

<400> SEQUENCE: 32
aaccagctga acttccatcg ttgcctcgcc      30

<210> SEQ ID NO 33
<211> LENGTH: 32
<212> TYPE: DNA
<213> ORGANISM: Artificial
<220> FEATURE:
<223> OTHER INFORMATION: SP9B_ins_INF_F1

<400> SEQUENCE: 33
caagaaggat gctttatggg caccatgatg cg      32

<210> SEQ ID NO 34
<211> LENGTH: 33
<212> TYPE: DNA
<213> ORGANISM: Artificial
<220> FEATURE:
<223> OTHER INFORMATION: SP9B-Trastuzumab_ins_INF_R1

<400> SEQUENCE: 34
aaccagctga acttcgacga tctgatgcgc cag        33

<210> SEQ ID NO 35
<211> LENGTH: 33
<212> TYPE: DNA
<213> ORGANISM: Artificial
<220> FEATURE:
<223> OTHER INFORMATION: SP10B_ins_INF_F1

<400> SEQUENCE: 35
aaccagctga acttctcgct gcttgagttt gcc        33

<210> SEQ ID NO 36
<211> LENGTH: 33
<212> TYPE: DNA
<213> ORGANISM: Artificial
<220> FEATURE:
<223> OTHER INFORMATION: SP10B-Trastuzumab_ins_INF_R1

<400> SEQUENCE: 36
aaccagctga acttctcgct gcttgagttt gcc        33

<210> SEQ ID NO 37
<211> LENGTH: 39
<212> TYPE: DNA
<213> ORGANISM: Artificial
<220> FEATURE:
<223> OTHER INFORMATION: SP12B_ins_INF_F1

<400> SEQUENCE: 37
caagaaggat gctttatggt gtctttcaat aaactgacc        39

<210> SEQ ID NO 38
<211> LENGTH: 33
<212> TYPE: DNA
<213> ORGANISM: Artificial
<220> FEATURE:
<223> OTHER INFORMATION: SP12B-Trastuzumab_ins_INF_R1

<400> SEQUENCE: 38
aaccagctga acttcggaac gggtccacag ggt        33

<210> SEQ ID NO 39
<211> LENGTH: 32
<212> TYPE: DNA
<213> ORGANISM: Artificial
<220> FEATURE:
<223> OTHER INFORMATION: SP13B_ins_INF_F1

<400> SEQUENCE: 39
caagaaggat gctttatggt cgccgtcctc ag        32

<210> SEQ ID NO 40
<211> LENGTH: 36
<212> TYPE: DNA
<213> ORGANISM: Artificial
<220> FEATURE:
<223> OTHER INFORMATION: SP13B-Trastuzumab_ins_INF_R1

```
<400> SEQUENCE: 40
aaccagctga acttcagact cgctagcaca gcacag                              36

<210> SEQ ID NO 41
<211> LENGTH: 35
<212> TYPE: DNA
<213> ORGANISM: Artificial
<220> FEATURE:
<223> OTHER INFORMATION: SP14B_ins_INF_F1

<400> SEQUENCE: 41
caagaaggat gcttttgcc gggacctata tgtcc                                35

<210> SEQ ID NO 42
<211> LENGTH: 37
<212> TYPE: DNA
<213> ORGANISM: Artificial
<220> FEATURE:
<223> OTHER INFORMATION: SP14B-Trastuzumab_ins_INF_R1

<400> SEQUENCE: 42
aaccagctga acttcttggg ccactattgt cttctcg                             37

<210> SEQ ID NO 43
<211> LENGTH: 40
<212> TYPE: DNA
<213> ORGANISM: Artificial
<220> FEATURE:
<223> OTHER INFORMATION: SP15B_ins_INF_F1

<400> SEQUENCE: 43
caagaaggat gctttatgaa acgtagcgat tatatgttgg                          40

<210> SEQ ID NO 44
<211> LENGTH: 37
<212> TYPE: DNA
<213> ORGANISM: Artificial
<220> FEATURE:
<223> OTHER INFORMATION: SP15B-Trastuzumab_ins_INF_R1

<400> SEQUENCE: 44
aaccagctga acttccttgc ctgaggcatc ttgaatc                             37

<210> SEQ ID NO 45
<211> LENGTH: 41
<212> TYPE: DNA
<213> ORGANISM: Artificial
<220> FEATURE:
<223> OTHER INFORMATION: SP16B_ins_INF_F1

<400> SEQUENCE: 45
caagaaggat gctttatgag caatagtgca tcatcgttta c                        41

<210> SEQ ID NO 46
<211> LENGTH: 33
<212> TYPE: DNA
<213> ORGANISM: Artificial
<220> FEATURE:
<223> OTHER INFORMATION: SP16B-Trastuzumab_ins_INF_R1

<400> SEQUENCE: 46
aaccagctga acttcggcca acggagtcgt ctc                                 33

<210> SEQ ID NO 47
```

<210> SEQ ID NO 47
<211> LENGTH: 34
<212> TYPE: DNA
<213> ORGANISM: Artificial
<220> FEATURE:
<223> OTHER INFORMATION: SP19B_ins_INF_F1

<400> SEQUENCE: 47
caagaaggat gcttttggc aagatgggtc actc         34

<210> SEQ ID NO 48
<211> LENGTH: 31
<212> TYPE: DNA
<213> ORGANISM: Artificial
<220> FEATURE:
<223> OTHER INFORMATION: SP19B-Trastuzumab_ins_INF_R1

<400> SEQUENCE: 48
aaccagctga acttcgccca tgaccggcat g         31

<210> SEQ ID NO 49
<211> LENGTH: 37
<212> TYPE: DNA
<213> ORGANISM: Artificial
<220> FEATURE:
<223> OTHER INFORMATION: SP21B_ins_INF_F1

<400> SEQUENCE: 49
caagaaggat gctttatggc attgactgat gaacagg         37

<210> SEQ ID NO 50
<211> LENGTH: 37
<212> TYPE: DNA
<213> ORGANISM: Artificial
<220> FEATURE:
<223> OTHER INFORMATION: SP21B-Trastuzumab_ins_INF_R1

<400> SEQUENCE: 50
aaccagctga acttcacgtg cagtggtatg gatgatt         37

<210> SEQ ID NO 51
<211> LENGTH: 37
<212> TYPE: DNA
<213> ORGANISM: Artificial
<220> FEATURE:
<223> OTHER INFORMATION: SP22B_ins_INF_F1

<400> SEQUENCE: 51
caagaaggat gcttttggt gtctatgaga agcccac         37

<210> SEQ ID NO 52
<211> LENGTH: 32
<212> TYPE: DNA
<213> ORGANISM: Artificial
<220> FEATURE:
<223> OTHER INFORMATION: SP22B-Trastuzumab_ins_INF_R1

<400> SEQUENCE: 52
aaccagctga acttcgatgc gctcacgctt gg         32

<210> SEQ ID NO 53
<211> LENGTH: 37
<212> TYPE: DNA
<213> ORGANISM: Artificial
<220> FEATURE:
<223> OTHER INFORMATION: SP23B_ins_INF_F1

<400> SEQUENCE: 53

```
caagaaggat gctttatgaa caagcgatgg aacaaac                                37
```

<210> SEQ ID NO 54
<211> LENGTH: 39
<212> TYPE: DNA
<213> ORGANISM: Artificial
<220> FEATURE:
<223> OTHER INFORMATION: SP23B-Trastuzumab_ins_INF_R1

<400> SEQUENCE: 54

```
aaccagctga acttcgatcg tcttgagaat cttcagacg                              39
```

<210> SEQ ID NO 55
<211> LENGTH: 30
<212> TYPE: DNA
<213> ORGANISM: Artificial
<220> FEATURE:
<223> OTHER INFORMATION: SP24B_ins_INF_F1

<400> SEQUENCE: 55

```
caagaaggat gctttatggt cggcatgcgc                                        30
```

<210> SEQ ID NO 56
<211> LENGTH: 31
<212> TYPE: DNA
<213> ORGANISM: Artificial
<220> FEATURE:
<223> OTHER INFORMATION: SP24B-Trastuzumab_ins_INF_R1

<400> SEQUENCE: 56

```
aaccagctga acttcgttgg tgcggttccg g                                      31
```

<210> SEQ ID NO 57
<211> LENGTH: 37
<212> TYPE: DNA
<213> ORGANISM: Artificial
<220> FEATURE:
<223> OTHER INFORMATION: SP25B_ins_INF_F1

<400> SEQUENCE: 57

```
caagaaggat gctttgtgat gttatccaca ccctcca                                37
```

<210> SEQ ID NO 58
<211> LENGTH: 33
<212> TYPE: DNA
<213> ORGANISM: Artificial
<220> FEATURE:
<223> OTHER INFORMATION: SP25B-Trastuzumab_ins_INF_R1

<400> SEQUENCE: 58

```
aaccagctga acttcctgct catgatcggc cca                                    33
```

<210> SEQ ID NO 59
<211> LENGTH: 40
<212> TYPE: DNA
<213> ORGANISM: Artificial
<220> FEATURE:
<223> OTHER INFORMATION: SP26_HU_ins_INF_F1

<400> SEQUENCE: 59

```
caagaaggat gctttatgaa gaagaaagct cttgctttcg                             40
```

<210> SEQ ID NO 60
<211> LENGTH: 33
<212> TYPE: DNA

```
<213> ORGANISM: Artificial
<220> FEATURE:
<223> OTHER INFORMATION: SP26_L0-Trastuzumab_ins_INF_R1

<400> SEQUENCE: 60
aaccagctga acttcagcgt tgctgttgga gcc                                    33

<210> SEQ ID NO 61
<211> LENGTH: 40
<212> TYPE: DNA
<213> ORGANISM: Artificial
<220> FEATURE:
<223> OTHER INFORMATION: SP26_HU_ins_INF_F1

<400> SEQUENCE: 61
caagaaggat gctttatgaa gaagaaagct cttgctttcg                             40

<210> SEQ ID NO 62
<211> LENGTH: 32
<212> TYPE: DNA
<213> ORGANISM: Artificial
<220> FEATURE:
<223> OTHER INFORMATION: SP26_L5-Trastuzumab_ins_INF_R1

<400> SEQUENCE: 62
aaccagctga acttcggtgt caccggaggc ag                                     32

<210> SEQ ID NO 63
<211> LENGTH: 36
<212> TYPE: DNA
<213> ORGANISM: Artificial
<220> FEATURE:
<223> OTHER INFORMATION: SP27_HU_ins_INF_F1

<400> SEQUENCE: 63
caagaaggat gctttatgaa caccattcgt cgcatc                                 36

<210> SEQ ID NO 64
<211> LENGTH: 32
<212> TYPE: DNA
<213> ORGANISM: Artificial
<220> FEATURE:
<223> OTHER INFORMATION: SP27_L0-Trastuzumab_ins_INF_R1

<400> SEQUENCE: 64
aaccagctga acttccgctt gtgcggtttg ac                                     32

<210> SEQ ID NO 65
<211> LENGTH: 36
<212> TYPE: DNA
<213> ORGANISM: Artificial
<220> FEATURE:
<223> OTHER INFORMATION: SP27_HU_ins_INF_F1

<400> SEQUENCE: 65
caagaaggat gctttatgaa caccattcgt cgcatc                                 36

<210> SEQ ID NO 66
<211> LENGTH: 31
<212> TYPE: DNA
<213> ORGANISM: Artificial
<220> FEATURE:
<223> OTHER INFORMATION: SP27_L6-Trastuzumab_ins_INF_R1

<400> SEQUENCE: 66
aaccagctga acttcggtgc ggttagccgt g                                      31
```

<210> SEQ ID NO 67
<211> LENGTH: 4730
<212> TYPE: DNA
<213> ORGANISM: Artificial
<220> FEATURE:
<223> OTHER INFORMATION: pHuSP1-Trastuzumab

<400> SEQUENCE: 67

```
ggatccgtct tcctgctggc ctatgcattg ggttccgcag tgcccactcc aggcggtctg      60
ggcggtgtgg aagcggcgct gacattcgcg ttcgtggcgg tcggagtgcc gcagggcgtg     120
gcgctttccg ccactttgct gcaccgcgtg gtgttctact ggctgcgcat tccgctgggc     180
gcggcggcca tgaagtggct tgacaagcat aatcttgtct gattcgtcta ttttcatacc     240
cccttcgggg aaatagatgt gaaaacccct ataaaacgcg gttttcgca gaaacatgcg      300
ctagtatcat tgatgacaac atggactaag caaaagtgct tgtcccctga cccaagaagg     360
atgctttatg gcggaaacta ccgttaagcc cacgaagctt gctgttattg gtgccggtgc     420
cgttggctcc accctcgcct tcgccgctgc ccagcgtggc atcgctcgcg agatcgtgct     480
tgaagacatc gccaaggagc gcgtggaaga agttcagctg gttgaaagcg gtggcggtct     540
ggttcagcct ggtggtagcc tgcgtctgag ctgtgcagca agcggtttta acattaaaga     600
tacctatatt cattgggtgc gtcaggcacc gggtaaaggt ctggaatggg ttgcacgtat     660
ttatccgacc aatggttata cccgttatgc cgatagcgtt aaaggtcgtt ttaccattag     720
cgcagatacc agcaaaaata ccgcatatct gcagatgaat agcctgcgtg cagaggatac     780
cgcagtgtat tattgtagcc gttggggtgg tgatggtttt tatgcaatgg attattgggg     840
tcagggcacc ctggttaccg ttagcagtgg tggtggtggt agcggtggtg ggggttcagg     900
tggtggtgga tccgatattc agatgaccca gagcccgagc agcctgagcg caagcgttgg     960
tgatcgtgtt accattacct gtcgtgcaag ccaggatgtt aataccgcag ttgcatggta    1020
tcagcagaaa ccgggtaaag caccgaaact gctgatttat agcgcaagct ttctgtatag    1080
cggtgttccg agccgtttta gcggtagccg tagcggcacc gatttaccc tgaccattag    1140
cagcctgcag ccggaagatt ttgcaaccta ttattgtcag cagcattaca ccacccctcc    1200
gacctttggt cagggcacca agttgaaat taaacatcat catcaccatc attaaccttc    1260
tgctcgtagc gattacttcg agcattactg acgacaaaga ccccgaccga gatggtcggg    1320
gtcttttttgt tgtggtgctg tgacgtgttg tccaaccgta ttattccgga ctagtcctcc    1380
aggacctcgt ctacgaggcg ctgagcgagg aatggcgcaa aagggacggc gagatcagcg    1440
acccatgggc caacgacgag gcggacggat accagccgcc ctcatacgag ccggtcaacc    1500
ccgaacgcag gactccccag acgccctccg atggcctgat ctgacgtccg aaaaaaggcg    1560
ctgtgcgccc tttttaaatc tttatataat cttttttacat tcttttagcc cctccgcagc    1620
cttactctcc caacgggttt cagccgaaac ctacaccaaa aggggagcga acctacacca    1680
aaggggagc gaacctacac caaaaggggga gcgaacctac accaaaaggg gagctatata    1740
cacctttgt tatttaaggt gcaagttgtg ctatgctgag gccatgtcca atgagatcgt    1800
gaagttcagc aaccagttca caacgtcgc gctgaagaag ttcgacgccg tgcacctgga    1860
cgtgctcatg gcgatcgcct caagggtgag ggagaagggc acggccacgg tggagttctc    1920
gttcgaggag ctgcgcggcc tcatgcgatt gaggaagaac ctgaccaaca gcagctggc    1980
cgacaagatc gtgcagacga acgcgcgcct gctggcgctg aactacatgt cgaggattc    2040
```

```
gggcaagatc atccagttcg cgctgttcac gaagttcgtc accgaccgc aggaggcgac    2100 tctcgcggtt ggggtcaacg aggagttcgc gttcctgctc aacgacctga ccagccagtt    2160
cacgcgcttc gagctggccg agttcgccga cctcaagagc aagtacgcca aggagttcta    2220
ccgcagggcc aagcagtacc gcagctccgg aatctggaag atcggccgcg acgagttctg    2280
ccgactgctt ggcgttccac cgtcggcaat aacccagaca cgatatctga atcagaaggt    2340
tcttcagcca attcaggagg agtgtgggcc tctccttggc ctgaagatcg agcgccagta    2400
cgtgaaacgc aggctgtcgg gcttcgtgtt cacattcgcc cgcgagaccc ctccggtgat    2460
cgacgccagg cccgtggagg cgaggaagac ggacggcgac ggcaagggcc attggacgag    2520
cgttgccggg tacggcgagg tgttcacgac cacggcgttg ttcgacgtga cggccgcccg    2580
ggctcacttc gacggcaccg ttgaagccgg ggagtgccgt ttctgcgcgt ttgacgcgcg    2640
caaccgcgaa catcatgcgc ggaacgccgg aaggctgttc tagcggccgt gtccgcgcct    2700
ctggggcggt tgcgcctgcc atgggtcgat ctgccgctgt tcggcctcac gctggtctgt    2760
gcgctgcctg atctccctga gcaggtcggc cttggtcctg ggggcgcttc gctcctcgaa    2820
cgggccgctc tccccaggt cctcgggctc gctcaggtcc aacggctcgt caccggacgg    2880
ctcgggccgg ttctctccct gtgccgggtt ctccgcctgt gcgcgttgtt cggccatgcg    2940
cagtgcgagg gccttcacct gttcggggct tgtcgactcg attttcgttc gtgaatacat    3000
gttataataa ctataactaa taacgtaacg tgactggcaa gagatatttt taaaacaatg    3060
aataggttta cacttacttt agttttatgg aaatgaaaga tcatatcata tataatctag    3120
aataaaatta actaaaataa ttattatcta gataaaaaat ttagaagcca atgaaatcta    3180
taaataaact aaattaagtt tatttaatta acaactatgg atataaaata ggtactaatc    3240
aaaatagtga ggaggatata tttgaataca tacgaacaaa ttaataaagt gaaaaaaata    3300
cttcggaaac atttaaaaaa taaccttatt ggtacttaca tgtttggatc aggagttgag    3360
agtggactaa aaccaaatag tgatcttgac tttttagtcg tcgtatctga accattgaca    3420
gatcaaagta aagaaatact tatacaaaaa attagaccta tttcaaaaaa aataggagat    3480
aaaagcaact tacgatatat tgaattaaca attattattc agcaagaaat ggtaccgtgg    3540
aatcatcctc ccaaacaaga atttatttat ggagaatggt tacaagagct ttatgaacaa    3600
ggatacattc ctcagaagga attaaattca gatttaacca taatgcttta ccaagcaaaa    3660
cgaaaaaata aaagaatata cggaaattat gacttagagg aattactacc tgatattcca    3720 tttctgatg tgagaagagc cattatggat tcgtcagagg aattaataga taattatcag    3780
gatgatgaaa ccaactctat attaacttta tgccgtatga ttttaactat ggacacgggt    3840
aaaatcatac caaagatat tgcgggaaat gcagtggctg aatcttctcc attagaacat    3900
agggagagaa ttttgttagc agttcgtagt tatcttggag agaatattga atggactaat    3960
gaaaatgtaa atttaactat aaactattta aataacagat taaaaaaatt ataaaaaaat    4020
tgaaaaaatg gtggaaacac ttttttcaat ttttttagat cttgagcaaa aggccagcaa    4080
aaggccagga accgtaaaaa ggccgcgttg ctggcgtttt tccataggct ccgcccccct    4140
gacgagcatc acaaaaatcg acgctcaagt cagaggtggc gaaacccgac aggactataa    4200
agataccagg cgtttccccc tggaagctcc ctcgtgcgct ctcctgttcc gaccctgccg    4260
cttaccggat acctgtccgc ctttctccct tgggaagcg tggcgctttc tcatagctca    4320
cgctgtaggt atctcagttc ggtgtaggtc gttcgctcca agctgggctg tgtgcacgaa    4380
ccccccgttc agcccgaccg ctgcgcctta tccggtaact atcgtcttga gtccaacccg    4440
```

```
gtaagacacg acttatcgcc actggcagca gccactggta acaggattag cagagcgagg    4500
tatgtaggcg gtgctacaga gttcttgaag tggtggccta actacggcta cactagaaga    4560
acagtatttg gtatctgcgc tctgctgaag ccagttacct tcggaaaaag agttggtagc    4620
tcttgatccg gcaaacaaac caccgctggt agcggtggtt ttttgtttg caagcagcag      4680 attacgcgca gaaaaaaagg atctcaagaa gatcctttga tctttctac               4730

<210> SEQ ID NO 68
<211> LENGTH: 156
<212> TYPE: DNA
<213> ORGANISM: Artificial
<220> FEATURE:
<223> OTHER INFORMATION: SP2B-3

<400> SEQUENCE: 68
gtgggtatga ctgagaacgc cgtaaatact gccgtgactt ccacctcctc tcccgcaatt     60
cccgccgaga cttccgccgt ctcccccgca actcgcgcag ccaaccgccc gctgggcaca   120
ccgctgggca agcaccccac ccgcgtgctg tttttg                              156

<210> SEQ ID NO 69
<211> LENGTH: 165
<212> TYPE: DNA
<213> ORGANISM: Artificial
<220> FEATURE:
<223> OTHER INFORMATION: SP3B-4

<400> SEQUENCE: 69
atgttcaata agcgacacat cgtccgtacc attgcggcca ccgccagcat cctggctctg     60
tcgttcaccg cagcctgcgg ttccggccag tccaccgcat ccaattccac cgattcggac   120
gacatcaccc agcagacgta caagccgggc aagctgacca tcgcc                    165

<210> SEQ ID NO 70
<211> LENGTH: 195
<212> TYPE: DNA
<213> ORGANISM: Artificial
<220> FEATURE:
<223> OTHER INFORMATION: SP4B-1

<400> SEQUENCE: 70
atgaccactc acaacagcca gtattccgcc gaaaccgccc atcccgacaa gcaggaaagc     60
agcccggcgc cgaccgccgc cggcaccacg gccagtaacg tctccacaac tggcaacgca   120
accacgccgg acgccagcat cgccctcaac gccgacgcca ctccggtagc cgacgttccc   180
ccgcgtctgt tcggc                                                    195

<210> SEQ ID NO 71
<211> LENGTH: 177
<212> TYPE: DNA
<213> ORGANISM: Artificial
<220> FEATURE:
<223> OTHER INFORMATION: SP5B-2

<400> SEQUENCE: 71
atgaccgcga ttgacgagac cgaccagcgc atcctcacca tgctggaggc cgacggccgc     60
gccacgctcg cgcaactggc ccaggcgacc ggactgtccg tctccgccgc ccagtcgcgc   120
gtgcagaagc tggagaagcg cggcatcatc aagggataca aggccatcat cgaccaa      177

<210> SEQ ID NO 72
```

<211> LENGTH: 141
<212> TYPE: DNA
<213> ORGANISM: Artificial
<220> FEATURE:
<223> OTHER INFORMATION: SP6B-1

<400> SEQUENCE: 72

```
atgaagattg cggttgcagg gactggctac gttggattgt ctgtcgcttt gctgctcgct     60
cagcacaatg aagttcatgc actcgacatc attcccgaga agtcgagca gttaaacaat    120
gggaaaagtc ctattgtcga t                                             141
```

<210> SEQ ID NO 73
<211> LENGTH: 126
<212> TYPE: DNA
<213> ORGANISM: Artificial
<220> FEATURE:
<223> OTHER INFORMATION: SP7B-1

<400> SEQUENCE: 73

```
atgtttgcgt gcgtagcccc gtttgcctct gccgattccg cgcagacgag tgctgtggtg     60
tcctcacgtt ctttcccgaa ggcgagttcg gtgaagaaga atttgttcgc cgaatccacc    120
tccacc                                                              126
```

<210> SEQ ID NO 74
<211> LENGTH: 204
<212> TYPE: DNA
<213> ORGANISM: Artificial
<220> FEATURE:
<223> OTHER INFORMATION: SP8B-1

<400> SEQUENCE: 74

```
atggttggtg acgacaccgt gacgatatgg tcgattgacg aatcccgaca gccgattcgc     60
cgcgttcgtc tgagtcgatt ccccgctggg gcgcgaatat gccttatcat gggttgcatg    120
acacccgcag agcgtgcgag cgcagtcgca tttgcactca agaactgcgc actggaagcg    180
atgacgccgg gcgaggcaac gatg                                          204
```

<210> SEQ ID NO 75
<211> LENGTH: 126
<212> TYPE: DNA
<213> ORGANISM: Artificial
<220> FEATURE:
<223> OTHER INFORMATION: SP9B-1

<400> SEQUENCE: 75

```
atgggcacca tgatgcgaat aggactgacc ggcggcatcg ccgcgggcaa aagtacggtg     60
gcggcgcaac tcaagcaact cggcgcgttg catatcgact acgatgcgct ggcgcatcag    120
atcgtc                                                              126
```

<210> SEQ ID NO 76
<211> LENGTH: 153
<212> TYPE: DNA
<213> ORGANISM: Artificial
<220> FEATURE:
<223> OTHER INFORMATION: SP10B-1

<400> SEQUENCE: 76

```
atgatgactg gtgcacaggc cgctcactgt ggttctgtat ccgcaatttc gctgggactg     60
cccgtttcca cggcgattcc cgaagccaaa ggctcactgc cgaaagcctt gttcgtaggc    120
aaagcgccga tttccggcaa actcaagcag cga                                153
```

<210> SEQ ID NO 77
<211> LENGTH: 171
<212> TYPE: DNA
<213> ORGANISM: Artificial
<220> FEATURE:
<223> OTHER INFORMATION: SP12B-2

<400> SEQUENCE: 77

```
atggtgtctt tcaataaact gacccgtact cttgctggca tcgctgccgc cgcgttgatc      60
gttccgctgg ccgcctgtgg tggctccggc aatggtggca ctgccaccgc cgaaggtatc     120
ccggccaagg gcaccgacga tggtaccgag atcaccctgt ggacccgttc c              171
```

<210> SEQ ID NO 78
<211> LENGTH: 138
<212> TYPE: DNA
<213> ORGANISM: Artificial
<220> FEATURE:
<223> OTHER INFORMATION: SP13B-1

<400> SEQUENCE: 78

```
atggtcgccg tcctcaggtt cggctgtctg ccatcatgct cggtcttgac tcattattta      60
tccgtgcatg ctgtaggcaa tcggcctgtg gtcggtctcc tcccgcaact tatattgctg     120
tgctgtgcta gcgagtct                                                   138
```

<210> SEQ ID NO 79
<211> LENGTH: 186
<212> TYPE: DNA
<213> ORGANISM: Artificial
<220> FEATURE:
<223> OTHER INFORMATION: SP14B-3

<400> SEQUENCE: 79

```
ttgccgggac ctatatgtcc ccggcaacaa cagccgtata tacgctaccg atcagtgctg      60
ccctcatcat ccttggcacc tgccgtggcg gcctcagtct ccttggcgtt ccacccggcg     120
acggcattcc aaccactcca tccgatgacc actagcaagc acagcgagaa gacaatagtg     180
gcccaa                                                                186
```

<210> SEQ ID NO 80
<211> LENGTH: 150
<212> TYPE: DNA
<213> ORGANISM: Artificial
<220> FEATURE:
<223> OTHER INFORMATION: SP15B-2

<400> SEQUENCE: 80

```
atgaaacgta gcgattatat gttggcggca ctcgcctcag ccgtcctgcc gaatctgggg      60
gtggccggcg tacgcgagaa cgtgcaggcc agcgcaaccg acgaggccaa aggcatcgat     120
cagaccgtga ttcaagatgc ctcaggcaag                                      150
```

<210> SEQ ID NO 81
<211> LENGTH: 135
<212> TYPE: DNA
<213> ORGANISM: Artificial
<220> FEATURE:
<223> OTHER INFORMATION: SP16B-2

<400> SEQUENCE: 81

```
atgagcaata gtgcatcatc gtttaccggc gtgtccagcg gttataccgc cgggactccg      60
```

```
gttccagccg attcacccat ccgtgacaat atcgccgatg ccgttcgccg cgtacgcgag    120
acgactccgt tggcc                                                    135

<210> SEQ ID NO 82
<211> LENGTH: 195
<212> TYPE: DNA
<213> ORGANISM: Artificial
<220> FEATURE:
<223> OTHER INFORMATION: SP19B-4

<400> SEQUENCE: 82
ttggcaagat gggtcactcg gagcgttccg gcaacggcct gtacgtcaac gtgcccggca    60
acaagtacca gccgatcttc gaggccggcg tggaatactt caccgcctga taatcggcgc   120
gtatcgcgtc tgatacggca cacagggaag gaactctcgg gttccttccc ttttttgttc   180
atgccggtca tgggc                                                    195

<210> SEQ ID NO 83
<211> LENGTH: 240
<212> TYPE: DNA
<213> ORGANISM: Artificial
<220> FEATURE:
<223> OTHER INFORMATION: SP21B-1

<400> SEQUENCE: 83
atggcattga ctgatgaaca ggtggagcgg tacgcgcgcc atctgatttt gaagggtgtg    60
ggggtcaaag ggcaaaagcg gttgctggcc tccagcgtgc tcatcatcgg agcgggcggt   120
cttggttctc cggccgccct gtatctggcg gcggccggcg tcggccatat cggactggtg   180
gacggcgatg tggtggatat gagcaatctg caacgccaaa tcatccatac cactgcacgt   240

<210> SEQ ID NO 84
<211> LENGTH: 240
<212> TYPE: DNA
<213> ORGANISM: Artificial
<220> FEATURE:
<223> OTHER INFORMATION: SP22B-2

<400> SEQUENCE: 84
ttggtgtcta tgagaagccc acgcgaggat tttgaggcgg caggcaagcg actgccttgg    60
gatgctgctg ctcgcagtgc agcgctgtcc gccaccgcgc cagtctctga cgtcaaggca   120
tccgccaatg gtgccgacaa tgccagcaac gctgaacatt ccgatgacat gcccaccgtg   180
ccgattcccg cacgcaaggc tgccacgacg ttcgacaccc cctccaagcg tgagcgcatc   240

<210> SEQ ID NO 85
<211> LENGTH: 180
<212> TYPE: DNA
<213> ORGANISM: Artificial
<220> FEATURE:
<223> OTHER INFORMATION: SP23 B

<400> SEQUENCE: 85
atgaacaagc gatggaacaa actgtgtgtg tccgccctcg cctgcatggc gttggtcgtg    60
ccgttgaccg cctgtgaagg ccaactgccg acgccggctg ctgatacctc caccaaggtt   120
gcgccggatt tgaccgaggc gcaggagaag aagattcgtc tgaagattct caagacgatc   180

<210> SEQ ID NO 86
<211> LENGTH: 180
<212> TYPE: DNA
<213> ORGANISM: Artificial
```

```
<220> FEATURE:
<223> OTHER INFORMATION: SP24B-4

<400> SEQUENCE: 86
atggtcggca tgcgcgacgt agccaaagcg gcaggggtgt ccttaagcac cgtttcgttg      60
gtggtcaaca acaccggcta cgtctcggcc gatatgcgtg ccaaagtcga gtccgcgatg     120
cgccagctca actacattcc caacgagctg ccccgcaacc tctaccggaa ccgcaccaac     180

<210> SEQ ID NO 87
<211> LENGTH: 180
<212> TYPE: DNA
<213> ORGANISM: Artificial
<220> FEATURE:
<223> OTHER INFORMATION: SP25B-3

<400> SEQUENCE: 87
gtgatgttat ccacaccctc cactacgttg ttttgcctcg cgctgggcag ccccacttca      60
gcaagagatt gcacagcttg cgttagggtg gagaacatga ctatcacagt atccacagac     120
ggttccgcat tagggaatcc aaacgggcca atgggctggg cctgggccga tcatgagcag     180

<210> SEQ ID NO 88
<211> LENGTH: 87
<212> TYPE: DNA
<213> ORGANISM: Artificial
<220> FEATURE:
<223> OTHER INFORMATION: SP26-1

<400> SEQUENCE: 88
atgaagaaga aagctcttgc tttcgctgcc atggcttgct ccgtggccat gctgctgagc      60
gcctgcggcg gctccaacag caacgct                                         87

<210> SEQ ID NO 89
<211> LENGTH: 102
<212> TYPE: DNA
<213> ORGANISM: Artificial
<220> FEATURE:
<223> OTHER INFORMATION: SP26-2

<400> SEQUENCE: 89
atgaagaaga aagctcttgc tttcgctgcc atggcttgct ccgtggccat gctgctgagc      60
gcctgcggcg gctccaacag caacgctgcc tccggtgaca cc                        102

<210> SEQ ID NO 90
<211> LENGTH: 156
<212> TYPE: DNA
<213> ORGANISM: Artificial
<220> FEATURE:
<223> OTHER INFORMATION: SP27-3

<400> SEQUENCE: 90
atgaacacca ttcgtcgcat cgtagagttc gccaaggtca agaccttcgc gttcaaatgc      60
atcgccatcg gcgccgcatt ggcgttggtg gcgtcggcat gcgtgattca gctggcctcc     120
acccagctca tcggcggccg tcaaaccgca caagcg                               156

<210> SEQ ID NO 91
<211> LENGTH: 174
<212> TYPE: DNA
<213> ORGANISM: Artificial
<220> FEATURE:
<223> OTHER INFORMATION: SP27-4
```

<400> SEQUENCE: 91

| | |
|---|---|
| atgaacacca ttcgtcgcat cgtagagttc gccaaggtca agaccttcgc gttcaaatgc | 60 |
| atcgccatcg gcgccgcatt ggcgttggtg gcgtcggcat gcgtgattca gctggcctcc | 120 |
| acccagctca tcggcggccg tcaaaccgca caagcggcca cggctaaccg cacc | 174 |

<210> SEQ ID NO 92
<211> LENGTH: 750
<212> TYPE: DNA
<213> ORGANISM: Artificial
<220> FEATURE:
<223> OTHER INFORMATION: opt-Trastuzumab scFv

<400> SEQUENCE: 92

| | |
|---|---|
| atggaagtgc agctggtcga atcgggcggc ggcctggtgc agccgggcgg ctccctgcgt | 60 |
| ctgtcgtgcg ccgcctcggg cttcaacatc aaggatacct acatccactg ggtgcgccag | 120 |
| gccccgggca agggcctgga atgggtggcc cgtatctacc cgaccaacgg ctacacccgc | 180 |
| tacgccgatt ccgtgaaggg ccgcttcacc atctccgccg ataccagcaa gaacaccgcc | 240 |
| tacctgcaga tgaactccct gcgcgccgaa gataccgccg tgtactactg ctcgcgctgg | 300 |
| ggcggcgacg gcttctacgc catggactac tggggccagg gcaccctggt gaccgtgtcc | 360 |
| agcggcggcg gcggctccgg cggcggcggc tcgggcggcg gcggctccga catccagatg | 420 |
| acccagtccc cgtcgtccct gagcgcctcg gtgggcgatc gcgtgaccat cacctgccgc | 480 |
| gcctcccagg atgtgaacac cgccgtggcc tggtaccagc agaagccggg caaggccccg | 540 |
| aagctgctga tctactcggc ctccttcctg tactccggcg tgccgtcccg tttctccggc | 600 |
| tcccgctcgg gcaccgactt caccctgacc atctcgtccc tgcagccgga agacttcgcc | 660 |
| acctactact gccagcagca ttacaccacc ccgccgacct cggccagggg caccaaggtg | 720 |
| gaaatcaagc atcatcatca tcatcactga | 750 |

<210> SEQ ID NO 93
<211> LENGTH: 4745
<212> TYPE: DNA
<213> ORGANISM: Artificial
<220> FEATURE:
<223> OTHER INFORMATION: pHuSP27L0-Trastuzumab scFv

<400> SEQUENCE: 93

| | |
|---|---|
| ggatccgtct tcctgctggc ctatgcattg ggttccgcag tgcccactcc aggcggtctg | 60 |
| ggcggtgtgg aagcggcgct gacattcgcg ttcgtggcgg tcggagtgcc gcagggcgtg | 120 |
| gcgctttccg ccactttgct gcaccgcgtg gtgttctact ggctgcgcat tccgctgggc | 180 |
| gcggcggcca tgaagtggct tgacaagcat aatcttgtct gattcgtcta ttttcatacc | 240 |
| cccttcgggg aaatagatgt gaaaaccctt ataaaacgcg gttttcgca gaaacatgcg | 300 |
| ctagtatcat tgatgacaac atggactaag caaaagtgct tgtcccctga cccaagaagg | 360 |
| atgctttatg aacaccattc gtcgcatcgt agagttcgcc aaggtcaaga ccttcgcgtt | 420 |
| caaatgcatc gccatcggcg ccgcattggc gttggtggcg tcggcatgcg tgattcagct | 480 |
| ggcctccacc cagctcatcg gcggccgtca aaccgcacaa gcggaagttc agctggttga | 540 |
| aagcggtggc ggtctggttc agcctggtgg tagcctgcgt ctgagctgtg cagcaagcgg | 600 |
| ttttaacatt aaagatacct atattcattg ggtgcgtcag gcaccgggta aaggtctgga | 660 |
| atgggttgca cgtatttatc cgaccaatgg ttatacccgt tatgccgata gcgttaaagg | 720 |
| tcgttttacc attagcgcag ataccagcaa aaataccgca tatctgcaga tgaatagcct | 780 |

```
gcgtgcagag gataccgcag tgtattattg tagccgttgg ggtggtgatg gtttttatgc      840
aatggattat tggggtcagg gcaccctggt taccgttagc agtggtggtg gtggtagcgg      900 tggtggggt  tcaggtggtg gtggatccga tattcagatg acccagagcc cgagcagcct      960
gagcgcaagc gttggtgatc gtgttaccat tacctgtcgt gcaagccagg atgttaatac     1020
cgcagttgca tggtatcagc agaaaccggg taaagcaccg aaactgctga tttatagcgc     1080
aagctttctg tatagcggtg ttccgagccg ttttagcggt agccgtagcg gcaccgattt     1140
taccctgacc attagcagcc tgcagccgga agattttgca acctattatt gtcagcagca     1200
ttacaccacc cctccgacct tggtcaggg  caccaaagtt gaaattaaac atcatcatca     1260
ccatcattaa ccttctgctc gtagcgatta cttcgagcat tactgacgac aaagaccccg     1320
accgagatgg tcggggtctt tttgttgtgg tgctgtgacg tgttgtccaa ccgtattatt     1380
ccggactagt cctccaggac ctcgtctacg aggcgctgag cgaggaatgg cgcaaaaggg     1440
acggcgagat cagcgaccca tgggccaacg acgaggcgga cggataccag ccgccctcat     1500
acgagccggt caaccccgaa cgcaggactc cccagacgcc ctccgatggc ctgatctgac     1560
gtccgaaaaa aggcgctgtg cgcccttttt aaatctttta taaatctttt tacattcttt     1620
tagcccctcc gcagccttac tctcccaacg ggtttcagcc gaaacctaca ccaaaagggg     1680
agcgaaccta caccaaaagg ggagcgaacc tacaccaaaa ggggagcgaa cctacaccaa     1740
aaggggagct atatacacct tttgttattt aaggtgcaag ttgtgctatg ctgaggccat     1800
gtccaatgag atcgtgaagt tcagcaacca gttcaacaac gtcgcgctga agaagttcga     1860
cgccgtgcac ctggacgtgc tcatggcgat cgcctcaagg gtgagggaga agggcacggc     1920
cacggtggag ttctcgttcg aggagctgcg cggcctcatg cgattgagga gaacctgac      1980 caacaagcag ctggccgaca gatcgtgca  gacgaacgcg cgcctgctgg cgctgaacta     2040
catgttcgag gattcgggca agatcatcca gttcgcgctg ttcacgaagt tcgtcaccga     2100
cccgcaggag gcgactctcg cggttggggt caacgaggag ttcgcgttcc tgctcaacga     2160
cctgaccagc cagttcacgc gcttcgagct ggccgagttc gccgacctca agagcaagta     2220
cgccaaggag ttctaccgca gggccaagca gtaccgcagc tccggaatct ggaagatcgg     2280
ccgcgacgag ttctgccgac tgcttggcgt tccaccgtcg gcaataaccc agacacgata     2340
tctgaatcag aaggttcttc agccaattca ggaggagtgt gggcctctcc ttggcctgaa     2400
gatcgagcgc cagtacgtga acgcaggct  gtcgggcttc gtgttcacat tcgcccgcga     2460
gacccctccg gtgatcgacg ccaggcccgt ggaggcgagg aagacggacg gcgacggcaa     2520
gggccattgg acgagcgttg ccgggtacgg cgaggtgttc acgaccacgg cgttgttcga     2580
cgtgacggcc gccgggctc  acttcgacgg caccgttgaa gccggggagt gccgtttctg     2640
cgcgtttgac gcgcgcaacc gcgaacatca tgcgcggaac gccggaaggc tgttctagcg     2700
gccgtgtccg cgcctctggg gcggttgcgc ctgccatggg tcgatctgcc gctgttcggc     2760
ctcacgctgg tctgtgcgct gcctgatctc cctgagcagg tcggccttgg tcctgggggc     2820
gcttcgctcc tcgaacgggc cgctctcccc caggtcctcg ggctcgctca ggtccaacgg     2880
ctcgtcaccg gacggctcgg gccggttctc tccctgtgcc gggttctccg cctgtgcgcg     2940
ttgttcggcc atgcgcagtg cgagggcctt cacctgttcg ggcttgtcg  actcgatttt     3000 cgttcgtgaa tacatgttat aataactata actaataacg taacgtgact ggcaagagat     3060
atttttaaaa caatgaatag gtttacactt actttagttt tatggaaatg aaagatcata     3120
```

```
tcatatataa tctagaataa aattaactaa aataattatt atctagataa aaaatttaga      3180
agccaatgaa atctataaat aaactaaatt aagtttattt aattaacaac tatggatata      3240
aaataggtac taatcaaaat agtgaggagg atatatttga atacatacga acaaattaat      3300
aaagtgaaaa aaatacttcg gaaacattta aaaaataacc ttattggtac ttacatgttt      3360
ggatcaggag ttgagagtgg actaaaacca aatagtgatc ttgacttttt agtcgtcgta      3420
tctgaaccat tgacagatca aagtaaagaa atacttatac aaaaaattag acctatttca      3480
aaaaaaatag gagataaaag caacttacga tatattgaat taacaattat tattcagcaa      3540
gaaatggtac cgtggaatca tcctcccaaa caagaattta tttatggaga atggttacaa      3600
gagctttatg aacaaggata cattcctcag aaggaattaa attcagattt aaccataatg      3660
ctttaccaag caaacgaaa aataaaaga atatacggaa attatgactt agaggaatta      3720
ctacctgata ttccattttc tgatgtgaga agagccatta tggattcgtc agaggaatta      3780
atagataatt atcaggatga tgaaaccaac tctatattaa ctttatgccg tatgatttta      3840
actatggaca cgggtaaaat cataccaaaa gatattgcgg gaaatgcagt ggctgaatct      3900
tctccattag aacatagga gagaattttg ttagcagttc gtagttatct tggagagaat      3960
attgaatgga ctaatgaaaa tgtaaattta actataaact atttaaataa cagattaaaa      4020
aaattataaa aaaattgaaa aaatggtgga aacacttttt tcaattttt tagatcttga      4080 gcaaaaggcc agcaaaaggc caggaaccgt aaaaaggccg cgttgctggc gttttttcat      4140
aggctccgcc cccctgacga gcatcacaaa aatcgacgct caagtcagag gtggcgaaac      4200
ccgacaggac tataaagata ccaggcgttt ccccctggaa gctccctcgt gcgctctcct      4260
gttccgaccc tgccgcttac cggatacctg tccgccttc tcccttcggg aagcgtggcg      4320
cttctctata gctcacgctg taggtatctc agttcggtgt aggtcgttcg ctccaagctg      4380
ggctgtgtgc acgaaccccc cgttcagccc gaccgctgcg ccttatccgg taactatcgt      4440
cttgagtcca acccggtaag acacgactta tcgccactgg cagcagccac tggtaacagg      4500
attagcagag cgaggtatgt aggcggtgct acagagttct tgaagtggtg gcctaactac      4560
ggctacacta agaagaacagt atttggtatc tgcgctctgc tgaagccagt taccttcgga      4620
aaaagagttg gtagctcttg atccggcaaa caaaccaccg ctggtagcgg tggtttttt      4680 gtttgcaagc agcagattac gcgcagaaaa aaaggatctc aagaagatcc tttgatcttt      4740
tctac                                                                 4745
```

<210> SEQ ID NO 94
<211> LENGTH: 4748
<212> TYPE: DNA
<213> ORGANISM: Artificial
<220> FEATURE:
<223> OTHER INFORMATION: pHuSP7L20-opt-Trastuzumab scFv

<400> SEQUENCE: 94

```
ggatccgtct tcctgctggc ctatgcattg ggttccgcag tgcccactcc aggcggtctg       60
ggcggtgtgg aagcggcgct gacattcgcg ttcgtggcgg tcggagtgcc gcagggcgtg      120
gcgctttccg ccactttgct gcaccgcgtg gtgttctact ggctgcgcat tccgctgggc      180
gcggcggcca tgaagtggct tgacaagcat aatcttgtct gattcgtcta ttttcatacc      240
cccttcgggg aaatagatgt gaaaacccct ataaaacgcg gttttcgca gaaacatgcg      300 ctagtatcat tgatgacaac atggactaag caaaagtgct tgtcccctga cccaagaagg      360
atgctttatg gcgttgatga tgagcgttaa gactattatt tccacatcag tggcgattat      420
```

```
cgccacgggt gccatgtttg cgtgcgtagc cccgtttgcc tctgccgatt ccgcgcagac     480
gagtgctgtg gtgtcctcac gttctttccc gaaggcgagt tcggtggaag tgcagctggt     540
cgaatcgggc ggcggcctgg tgcagccggg cggctccctg cgtctgtcgt gcgccgcctc     600
gggcttcaac atcaaggata cctacatcca ctgggtgcgc caggccccgg gcaagggcct     660
ggaatgggtg gcccgtatct acccgaccaa cggctacacc cgctacgccg attccgtgaa     720
gggccgcttc accatctccg ccgataccag caagaacacc gcctacctgc agatgaactc     780
cctgcgcgcc gaagataccg ccgtgtacta ctgctcgcgc tggggcggcg acggcttcta     840
cgccatggac tactgggggcc agggcaccct ggtgaccgtg tccagcggcg gcggcggctc     900
cggcggcggc ggctcgggcg gcggcggctc cgacatccag atgacccagt ccccgtcgtc     960
cctgagcgcc tcggtgggcg atcgcgtgac catcacctgc cgcgcctccc aggatgtgaa    1020
caccgccgtg gcctggtacc agcagaagcc gggcaaggcc ccgaagctgc tgatctactc    1080
ggcctccttc ctgtactccg gcgtgccgtc ccgtttctcc ggctcccgct cgggcaccga    1140
cttcaccctg accatctcgt ccctgcagcc ggaagacttc gccacctact actgccagca    1200
gcattacacc ccccgccga ccttcggcca gggcaccaag gtggaaatca gcatcatca    1260 tcatcatcac tgaccttctg ctcgtagcga ttacttcgag cattactgac gacaaagacc    1320
ccgaccgaga tggtcggggt cttttttgttg tggtgctgtg acgtgttgtc caaccgtatt    1380
attccggact agtcctccag gacctcgtct acgaggcgct gagcgaggaa tggcgcaaaa    1440
gggacggcga gatcagcgac ccatgggcca acgacgaggc ggacggatac cagccgccct    1500
catacgagcc ggtcaacccc gaacgcagga ctccccagac gccctccgat ggcctgatct    1560
gacgtccgaa aaaggcgct gtgcgccctt tttaaatctt ttataaatct ttttacattc    1620
ttttagcccc tccgcagcct tactctccca acgggtttca gccgaaacct acaccaaaag    1680
gggagcgaac ctacaccaaa aggggagcga acctacacca aaggggagc gaacctacac    1740 caaaagggga gctatataca cctttttgtta tttaaggtgc aagttgtgct atgctgaggc    1800
catgtccaat gagatcgtga agttcagcaa ccagttcaac aacgtcgcgc tgaagaagtt    1860
cgacgccgtg cacctggacg tgctcatggc gatcgcctca agggtgaggg agaagggcac    1920
ggccacggtg gagttctcgt tcgaggagct gcgcggcctc atgcgattga ggaagaacct    1980
gaccaacaag cagctggccg acaagatcgt gcagacgaac gcgcgcctgc tggcgctgaa    2040
ctacatgttc gaggattcgg gcaagatcat ccagttcgcg ctgttcacga agttcgtcac    2100
cgaccccgca gaggcgactc tcgcggttgg ggtcaacgag gagttcgcgt tcctgctcaa    2160
cgacctgacc agccagttca cgcgcttcga gctggccgag ttcgccgacc tcaagagcaa    2220
gtacgccaag gagttctacc gcaggccaa gcagtaccgc agctccggaa tctggaagat    2280
cggccgcgac gagttctgcc gactgcttgg cgttccaccg tcggcaataa cccagacacg    2340
atatctgaat cagaaggttc ttcagccaat tcaggaggag tgtgggcctc tccttggcct    2400
gaagatcgag cgccagtacg tgaaacgcag gctgtcgggc ttcgtgttca cattcgcccg    2460
cgagacccct ccggtgatcg acgccaggcc cgtggaggcg aggaagacgg acggcgacgg    2520
caagggccat tggacgagcg ttgccgggta cggcgaggtt ttcacgacca cggcgttgtt    2580
cgacgtgacg gccgcccggg ctcacttcga cggcaccgtt gaagccgggg agtgccgttt    2640
ctgcgcgttt gacgcgcgca accgcgaaca tcatgcgcgg aacgccggaa ggctgttcta    2700
gcggccgtgt ccgcgcctct ggggcggttg cgcctgccat gggtcgatct gccgctgttc    2760
```

```
ggcctcacgc tggtctgtgc gctgcctgat ctccctgagc aggtcggcct tggtcctggg   2820
ggcgcttcgc tcctcgaacg ggccgctctc cccaggtcc tcgggctcgc tcaggtccaa    2880
cggctcgtca ccggacggct cgggccggtt ctctccctgt gccgggttct ccgcctgtgc   2940
gcgttgttcg gccatgcgca gtgcgagggc cttcacctgt tcggggcttg tcgactcgat   3000
tttcgttcgt gaatacatgt tataataact ataactaata cgtaacgtg actggcaaga    3060 gatattttta aaacaatgaa taggtttaca cttactttag ttttatggaa atgaaagatc   3120
atatcatata taatctagaa taaaattaac taaaataatt attatctaga taaaaaattt   3180
agaagccaat gaaatctata aataaactaa attaagttta tttaattaac aactatggat   3240
ataaaatagg tactaatcaa aatagtgagg aggatatatt tgaatacata cgaacaaatt   3300
aataaagtga aaaaaatact tcggaaacat ttaaaaaata accttattgg tacttacatg   3360
tttggatcag gagttgagag tggactaaaa ccaaatagtg atcttgactt tttagtcgtc   3420
gtatctgaac cattgacaga tcaaagtaaa gaaatactta tacaaaaaat tagacctatt   3480
tcaaaaaaaa taggagataa aagcaactta cgatatattg aattaacaat tattattcag   3540
caagaaatgg taccgtggaa tcatcctccc aaacaagaat ttatttatgg agaatggtta   3600
caagagcttt atgaacaagg atacattcct cagaaggaat taaattcaga tttaaccata   3660
atgctttacc aagcaaaacg aaaaaataaa agaatatacg gaattatga cttagaggaa    3720 ttactacctg atattccatt ttctgatgtg agaagagcca ttatggattc gtcagaggaa   3780
ttaatagata attatcagga tgatgaaacc aactctatat taactttatg ccgtatgatt   3840
ttaactatgg acacgggtaa aatcatacca aaagatattg cgggaaatgc agtggctgaa   3900
tcttctccat tagaacatag ggagagaatt tgttagcag ttcgtagtta tcttggagag    3960
aatattgaat ggactaatga aaatgtaaat ttaactataa actatttaaa taacagatta   4020
aaaaaattat aaaaaaattg aaaaaatggt ggaaacactt ttttcaattt ttttagatct   4080
tgagcaaaag gccagcaaaa ggccaggaac cgtaaaaagg ccgcgttgct ggcgtttttc   4140
cataggctcc gccccctga cgagcatcac aaaaatcgac gctcaagtca gaggtggcga    4200
aacccgacag gactataaag ataccaggcg tttccccctg gaagctccct cgtgcgctct   4260
cctgttccga ccctgccgct taccggatac ctgtccgcct ttctcccttc gggaagcgtg   4320
gcgctttctc atagctcacg ctgtaggtat ctcagttcgg tgtaggtcgt tcgctccaag   4380
ctgggctgtg tgcacgaacc ccccgttcag cccgaccgct gcgccttatc cggtaactat   4440
cgtcttgagt ccaacccggt aagacacgac ttatcgccac tggcagcagc cactggtaac   4500
aggattagca gagcgaggta tgtaggcggt gctacagagt tcttgaagtg gtggcctaac   4560
tacggctaca ctagaagaac agtatttggt atctgcgctc tgctgaagcc agttaccttc   4620
ggaaaaagag ttggtagctc ttgatccggc aaacaaacca ccgctggtag cggtggtttt   4680
tttgtttgca agcagcagat tacgcgcaga aaaaaggat ctcaagaaga tcctttgatc     4740
ttttctac                                                            4748
```

<210> SEQ ID NO 95
<211> LENGTH: 4616
<212> TYPE: DNA
<213> ORGANISM: Artificial
<220> FEATURE:
<223> OTHER INFORMATION: pP30SP7L20-opt-Trastuzumab scFv

<400> SEQUENCE: 95

```
tagccggcat tttcgcgata cattccccgg aatgttgcgc aacggggaac gcgcaccaca     60
```

```
ccgcaaccac agtgcgccac gcccagtccg gccctgtgcg ctataatagg tcagttattc      120
gcgcgcgcgt ggcgccctct acaccccgag ccgcgaggac acgtggattc cggacggcca      180
tgccccacat ggcaaaccga gaacccgcac acctagcatt acaaggagag ccattatggc      240
gttgatgatg agcgttaaga ctattatttc cacatcagtg gcgattatcg ccacgggtgc      300
catgtttgcg tgcgtagccc cgtttgcctc tgccgattcc gcgcagacga gtgctgtggt      360
gtcctcacgt tctttcccga aggcgagttc ggtggaagtg cagctggtcg aatcgggcgg      420
cggcctggtg cagccgggcg gctccctgcg tctgtcgtgc gccgcctcgg gcttcaacat      480
caaggatacc tacatccact gggtgcgcca ggccccgggc aagggcctgg aatgggtggc      540
ccgtatctac ccgaccaacg gctacacccg ctacgccgat tccgtgaagg gccgcttcac      600
catctccgcc gataccagca agaacaccgc ctacctgcag atgaactccc tgcgcgccga      660
agataccgcc gtgtactact gctcgcgctg gggcggcgac ggcttctacg ccatggacta      720
ctggggccag ggcaccctgg tgaccgtgtc cagcggcggc ggcggctccg gcggcggcgg      780
ctcgggcggc ggcggctccg acatccagat gacccagtcc ccgtcgtccc tgagcgcctc      840
ggtgggcgat cgcgtgacca tcacctgccg cgcctcccag gatgtgaaca ccgccgtggc      900
ctggtaccag cagaagccgg gcaaggcccc gaagctgctg atctactcgg cctccttcct      960
gtactccggc gtgccgtccc gtttctccgg ctcccgctcg gcaccgact tcaccctgac     1020 catctcgtcc ctgcagccgg aagacttcgc cacctactac tgccagcagc attacaccac     1080
cccgccgacc ttcggccagg gcaccaaggt ggaaatcaag catcatcatc atcatcactg     1140
accttctgct cgtagcgatt acttcgagca ttactgacga caaagacccc gaccgagatg     1200 gtcgggtct ttttgttgtg gtgctgtgac gtgttgtcca accgtattat tccggactag     1260
tcctccagga cctcgtctac gaggcgctga gcgaggaatg gcgcaaaagg gacggcgaga     1320
tcagcgaccc atgggccaac gacgaggcgg acggatacca gccgccctca tacgagccgg     1380
tcaaccccga acgcaggact ccccagacgc cctccgatgg cctgatctga cgtccgaaaa     1440
aaggcgctgt gcgccctttt taaatctttt ataaatcttt ttacattctt ttagcccctc     1500
cgcagcctta ctctcccaac gggtttcagc cgaaacctac accaaaaggg gagcgaacct     1560
acaccaaaag gggagcgaac ctacaccaaa aggggagcga acctacacca aaaggggagc     1620
tatatacacc ttttgttatt taaggtgcaa gttgtgctat gctgaggcca tgtccaatga     1680
gatcgtgaag ttcagcaacc agttcaacaa cgtcgcgctg aagaagttcg acgccgtgca     1740
cctggacgtg ctcatggcga tcgcctcaag ggtgaggag aagggcacgg ccacggtgga     1800
gttctcgttc gaggagctgc gcggcctcat gcgattgagg aagaacctga ccaacaagca     1860
gctggccgac aagatcgtgc agacgaacgc gcgcctgctg cgctgaact acatgttcga     1920 ggattcgggc aagatcatcc agttcgcgct gttcacgaag ttcgtcaccg acccgcagga     1980
ggcgactctc gcggttgggg tcaacgagga gttcgcgttc ctgctcaacg acctgaccag     2040
ccagttcacg cgcttcgagc tggccgagtt cgccgacctc aagagcaagt acgccaagga     2100
gttctaccgc agggcaagc agtaccgcag ctccggaatc tggaagatcg ccgcgacga     2160 gttctgccga ctgcttggcg ttccaccgtc ggcaataacc cagacacgat atctgaatca     2220
gaaggttctt cagccaattc aggaggagtg tgggcctctc cttggcctga agatcgagcg     2280
ccagtacgtg aaacgcaggc tgtcgggctt cgtgttcaca ttcgccgcg agacccctcc     2340 ggtgatcgac gccaggcccg tggaggcgag gaagacggac ggcgacggca agggccattg     2400
```

```
gacgagcgtt gccgggtacg gcgaggtgtt cacgaccacg gcgttgttcg acgtgacggc    2460
cgcccgggct cacttcgacg gcaccgttga agccggggag tgccgtttct gcgcgtttga    2520
cgcgcgcaac cgcgaacatc atgcgcggaa cgccggaagg ctgttctagc ggccgtgtcc    2580
gcgcctctgg ggcggttgcg cctgccatgg gtcgatctgc cgctgttcgg cctcacgctg    2640
gtctgtgcgc tgcctgatct ccctgagcag gtcggccttg gtcctggggg cgcttcgctc    2700
ctcgaacggg ccgctctccc ccaggtcctc gggctcgctc aggtccaacg gctcgtcacc    2760
ggacggctcg ggccggttct ctccctgtgc cgggttctcc gcctgtgcgc gttgttcggc    2820
catgcgcagt gcgagggcct tcacctgttc ggggcttgtc gactcgattt tcgttcgtga    2880
atacatgtta taataactat aactaataac gtaacgtgac tggcaagaga tatttttaaa    2940
acaatgaata ggtttacact tactttagtt ttatggaaat gaaagatcat atcatatata    3000
atctagaata aaattaacta aataattat tatctagata aaaaatttag aagccaatga    3060
aatctataaa taaactaaat taagtttatt taattaacaa ctatggatat aaaataggta    3120
ctaatcaaaa tagtgaggag gatatatttg aatacatacg aacaaattaa taaagtgaaa    3180
aaaatacttc ggaaacattt aaaaaataac cttattggta cttacatgtt tggatcagga    3240
gttgagagtg gactaaaacc aaatagtgat cttgactttt tagtcgtcgt atctgaacca    3300
ttgacagatc aaagtaaaga aatacttata caaaaaatta gacctatttc aaaaaaaata    3360
ggagataaaa gcaacttacg atatattgaa ttaacaatta ttattcagca agaaatggta    3420
ccgtggaatc atcctcccaa acaagaattt atttatggag aatggttaca agagctttat    3480
gaacaaggat acattcctca gaaggaatta aattcagatt taaccataat gctttaccaa    3540
gcaaaacgaa aaaataaaag aatatacgga aattatgact tagaggaatt actacctgat    3600
attccatttt ctgatgtgag aagagccatt atggattcgt cagaggaatt aatagataat    3660
tatcaggatg atgaaaccaa ctctatatta actttatgcc gtatgatttt aactatggac    3720
acgggtaaaa tcataccaaa agatattgcg ggaaatgcag tggctgaatc ttctccatta    3780
gaacataggg agagaatttt gttagcagtt cgtagttatc ttggagagaa tattgaatgg    3840
actaatgaaa atgtaaattt aactataaac tatttaaata acagattaaa aaaattataa    3900
aaaaattgaa aaaatggtgg aaacactttt ttcaattttt ttagatcttg agcaaaaggc    3960
cagcaaaagg ccaggaaccg taaaaaggcc gcgttgctgg cgttttttcca taggctccgc    4020 cccccctgacg agcatcacaa aaatcgacgc tcaagtcaga ggtggcgaaa cccgacagga    4080
ctataaagat accaggcgtt tcccctgga agctccctcg tgcgctctcc tgttccgacc    4140
ctgccgctta ccggatacct gtccgccttt ctcccttcgg gaagcgtggc gctttctcat    4200
agctcacgct gtaggtatct cagttcggtg taggtcgttc gctccaagct gggctgtgtg    4260
cacgaacccc ccgttcagcc cgaccgctgc gccttatccg gtaactatcg tcttgagtcc    4320
aacccggtaa gacacgactt atcgccactg gcagcagcca ctggtaacag gattagcaga    4380
gcgaggtatg taggcggtgc tacagagttc ttgaagtggt ggcctaacta cggctacact    4440
agaagaacag tatttggtat ctgcgctctg ctgaagccag ttaccttcgg aaaaagagtt    4500
ggtagctctt gatccggcaa acaaaccacc gctggtagcg gtggtttttt tgtttgcaag    4560
cagcagatta cgcgcagaaa aaaaggatct caagaagatc ctttgatctt ttctac    4616
```

<210> SEQ ID NO 96
<211> LENGTH: 36
<212> TYPE: DNA
<213> ORGANISM: Artificial

```
<220> FEATURE:
<223> OTHER INFORMATION: opt-Trastuzumab scFv_ins_INF_F1 primer

<400> SEQUENCE: 96
caaaccgcac aagcggaagt gcagctggtc gaatcg                               36

<210> SEQ ID NO 97
<211> LENGTH: 41
<212> TYPE: DNA
<213> ORGANISM: Artificial
<220> FEATURE:
<223> OTHER INFORMATION: opt-Trastuzumab scFv_ins_INF_R1 primer

<400> SEQUENCE: 97
gctacgagca aaggtcagt gatgatgatg atgatgcttg a                          41

<210> SEQ ID NO 98
<211> LENGTH: 25
<212> TYPE: DNA
<213> ORGANISM: Artificial
<220> FEATURE:
<223> OTHER INFORMATION: SP1_Vec_F1 primer

<400> SEQUENCE: 98
ccttctgctc gtagcgatta cttcg                                           25

<210> SEQ ID NO 99
<211> LENGTH: 16
<212> TYPE: DNA
<213> ORGANISM: Artificial
<220> FEATURE:
<223> OTHER INFORMATION: d0018_0aa_Vec_R3 primer

<400> SEQUENCE: 99
cgcttgtgcg gtttga                                                     16

<210> SEQ ID NO 100
<211> LENGTH: 34
<212> TYPE: DNA
<213> ORGANISM: Artificial
<220> FEATURE:
<223> OTHER INFORMATION: SP7L20-opt-Trastuzumab scFv_ins_INF_F1 primer

<400> SEQUENCE: 100
caagaaggat gctttatggc gttgatgatg agcg                                 34

<210> SEQ ID NO 101
<211> LENGTH: 32
<212> TYPE: DNA
<213> ORGANISM: Artificial
<220> FEATURE:
<223> OTHER INFORMATION: SP7L20-opt-Trastuzumab scFv_ins_INF_R1 primer

<400> SEQUENCE: 101
gaccagctgc acttccaccg aactcgcctt cg                                   32

<210> SEQ ID NO 102
<211> LENGTH: 21
<212> TYPE: DNA
<213> ORGANISM: Artificial
<220> FEATURE:
<223> OTHER INFORMATION: Hu-opt-Trastuzumab_vec_F1 primer

<400> SEQUENCE: 102
gaagtgcagc tggtcgaatc g                                               21
```

<210> SEQ ID NO 103
<211> LENGTH: 32
<212> TYPE: DNA
<213> ORGANISM: Artificial
<220> FEATURE:
<223> OTHER INFORMATION: P30_ins_F1 primer

<400> SEQUENCE: 103
tttgatcttt tctactagcc ggcattttcg cg                          32

<210> SEQ ID NO 104
<211> LENGTH: 39
<212> TYPE: DNA
<213> ORGANISM: Artificial
<220> FEATURE:
<223> OTHER INFORMATION: P30_SP7_ins_R1 primer

<400> SEQUENCE: 104
catcatcaac gccataatgg ctctccttgt aatgctagg                   39

<210> SEQ ID NO 105
<211> LENGTH: 19
<212> TYPE: DNA
<213> ORGANISM: Artificial
<220> FEATURE:
<223> OTHER INFORMATION: SP7_Vec_F1 primer

<400> SEQUENCE: 105
atggcgttga tgatgagcg                                         19

<210> SEQ ID NO 106
<211> LENGTH: 31
<212> TYPE: DNA
<213> ORGANISM: Artificial
<220> FEATURE:
<223> OTHER INFORMATION: pUC_ori_Vec_R2 primer

<400> SEQUENCE: 106
gtagaaaaga tcaaaggatc ttcttgagat c                           31

<210> SEQ ID NO 107
<211> LENGTH: 33
<212> TYPE: PRT
<213> ORGANISM: Artificial
<220> FEATURE:
<223> OTHER INFORMATION: signal peptide 7

<400> SEQUENCE: 107

Met Ala Leu Met Met Ser Val Lys Thr Ile Ile Ser Thr Ser Val Ala
1               5                   10                  15

Ile Ile Ala Thr Gly Ala Met Phe Ala Cys Val Ala Pro Phe Ala Ser
            20                  25                  30

Ala

<210> SEQ ID NO 108
<211> LENGTH: 99
<212> TYPE: DNA
<213> ORGANISM: Artificial
<220> FEATURE:
<223> OTHER INFORMATION: SP7

<400> SEQUENCE: 108
atggcgttga tgatgagcgt taagactatt atttccacat cagtggcgat tatcgccacg   60
ggtgccatgt ttgcgtgcgt agccccgttt gcctctgcc                         99

<210> SEQ ID NO 109
<211> LENGTH: 53
<212> TYPE: PRT
<213> ORGANISM: Artificial
<220> FEATURE:
<223> OTHER INFORMATION: signal peptide 7 Linker 20/SP7L20

<400> SEQUENCE: 109

Met Ala Leu Met Met Ser Val Lys Thr Ile Ile Ser Thr Ser Val Ala
1               5                   10                  15

Ile Ile Ala Thr Gly Ala Met Phe Ala Cys Val Ala Pro Phe Ala Ser
            20                  25                  30

Ala Asp Ser Ala Gln Thr Ser Ala Val Val Ser Ser Arg Ser Phe Pro
        35                  40                  45

Lys Ala Ser Ser Val
    50

<210> SEQ ID NO 110
<211> LENGTH: 159
<212> TYPE: DNA
<213> ORGANISM: Artificial
<220> FEATURE:
<223> OTHER INFORMATION: SP7L20

<400> SEQUENCE: 110
atggcgttga tgatgagcgt taagactatt atttccacat cagtggcgat tatcgccacg      60
ggtgccatgt ttgcgtgcgt agccccgttt gcctctgccg attccgcgca gacgagtgct     120
gtggtgtcct cacgttcttt cccgaaggcg agttcggtg                            159

<210> SEQ ID NO 111
<211> LENGTH: 306
<212> TYPE: PRT
<213> ORGANISM: Artificial
<220> FEATURE:
<223> OTHER INFORMATION: SP27L6-Trastuzumab scFv

<400> SEQUENCE: 111

Met Asn Thr Ile Arg Arg Ile Val Glu Phe Ala Lys Val Lys Thr Phe
1               5                   10                  15

Ala Phe Lys Cys Ile Ala Ile Gly Ala Ala Leu Ala Leu Val Ala Ser
            20                  25                  30

Ala Cys Val Ile Gln Leu Ala Ser Thr Gln Leu Ile Gly Gly Arg Gln
        35                  40                  45

Thr Ala Gln Ala Ala Thr Ala Asn Arg Thr Glu Val Gln Leu Val Glu
    50                  55                  60

Ser Gly Gly Gly Leu Val Gln Pro Gly Gly Ser Leu Arg Leu Ser Cys
65                  70                  75                  80

Ala Ala Ser Gly Phe Asn Ile Lys Asp Thr Tyr Ile His Trp Val Arg
                85                  90                  95

Gln Ala Pro Gly Lys Gly Leu Glu Trp Val Ala Arg Ile Tyr Pro Thr
            100                 105                 110

Asn Gly Tyr Thr Arg Tyr Ala Asp Ser Val Lys Gly Arg Phe Thr Ile
        115                 120                 125

Ser Ala Asp Thr Ser Lys Asn Thr Ala Tyr Leu Gln Met Asn Ser Leu
    130                 135                 140

Arg Ala Glu Asp Thr Ala Val Tyr Tyr Cys Ser Arg Trp Gly Gly Asp
145                 150                 155                 160

```
Gly Phe Tyr Ala Met Asp Tyr Trp Gly Gln Gly Thr Leu Val Thr Val
                165                 170                 175

Ser Ser Gly Gly Gly Gly Ser Gly Gly Gly Gly Ser Gly Gly Gly Gly
            180                 185                 190

Ser Asp Ile Gln Met Thr Gln Ser Pro Ser Ser Leu Ser Ala Ser Val
            195                 200                 205

Gly Asp Arg Val Thr Ile Thr Cys Arg Ala Ser Gln Asp Val Asn Thr
        210                 215                 220

Ala Val Ala Trp Tyr Gln Gln Lys Pro Gly Lys Ala Pro Lys Leu Leu
225                 230                 235                 240

Ile Tyr Ser Ala Ser Phe Leu Tyr Ser Gly Val Pro Ser Arg Phe Ser
                245                 250                 255

Gly Ser Arg Ser Gly Thr Asp Phe Thr Leu Thr Ile Ser Ser Leu Gln
            260                 265                 270

Pro Glu Asp Phe Ala Thr Tyr Tyr Cys Gln Gln His Tyr Thr Thr Pro
        275                 280                 285

Pro Thr Phe Gly Gln Gly Thr Lys Val Glu Ile Lys His His His His
    290                 295                 300

His His
305

<210> SEQ ID NO 112
<211> LENGTH: 300
<212> TYPE: PRT
<213> ORGANISM: Artificial
<220> FEATURE:
<223> OTHER INFORMATION: SP27L0-Trastuzumab scFv

<400> SEQUENCE: 112

Met Asn Thr Ile Arg Arg Ile Val Glu Phe Ala Lys Val Lys Thr Phe
1               5                   10                  15

Ala Phe Lys Cys Ile Ala Ile Gly Ala Ala Leu Ala Leu Val Ala Ser
                20                  25                  30

Ala Cys Val Ile Gln Leu Ala Ser Thr Gln Leu Ile Gly Gly Arg Gln
            35                  40                  45

Thr Ala Gln Ala Glu Val Gln Leu Val Glu Ser Gly Gly Gly Leu Val
        50                  55                  60

Gln Pro Gly Gly Ser Leu Arg Leu Ser Cys Ala Ala Ser Gly Phe Asn
65                  70                  75                  80

Ile Lys Asp Thr Tyr Ile His Trp Val Arg Gln Ala Pro Gly Lys Gly
                85                  90                  95

Leu Glu Trp Val Ala Arg Ile Tyr Pro Thr Asn Gly Tyr Thr Arg Tyr
                100                 105                 110

Ala Asp Ser Val Lys Gly Arg Phe Thr Ile Ser Ala Asp Thr Ser Lys
            115                 120                 125

Asn Thr Ala Tyr Leu Gln Met Asn Ser Leu Arg Ala Glu Asp Thr Ala
        130                 135                 140

Val Tyr Tyr Cys Ser Arg Trp Gly Gly Asp Gly Phe Tyr Ala Met Asp
145                 150                 155                 160

Tyr Trp Gly Gln Gly Thr Leu Val Thr Val Ser Ser Gly Gly Gly Gly
                165                 170                 175

Ser Gly Gly Gly Gly Ser Gly Gly Gly Gly Ser Asp Ile Gln Met Thr
            180                 185                 190

Gln Ser Pro Ser Ser Leu Ser Ala Ser Val Gly Asp Arg Val Thr Ile
        195                 200                 205
```

Thr Cys Arg Ala Ser Gln Asp Val Asn Thr Ala Val Ala Trp Tyr Gln
    210                 215                 220

Gln Lys Pro Gly Lys Ala Pro Lys Leu Leu Ile Tyr Ser Ala Ser Phe
225                 230                 235                 240

Leu Tyr Ser Gly Val Pro Ser Arg Phe Ser Gly Ser Arg Ser Gly Thr
                245                 250                 255

Asp Phe Thr Leu Thr Ile Ser Ser Leu Gln Pro Glu Asp Phe Ala Thr
            260                 265                 270

Tyr Tyr Cys Gln Gln His Tyr Thr Thr Pro Pro Thr Phe Gly Gln Gly
            275                 280                 285

Thr Lys Val Glu Ile Lys His His His His His His
290                 295                 300

<210> SEQ ID NO 113
<211> LENGTH: 303
<212> TYPE: PRT
<213> ORGANISM: Artificial
<220> FEATURE:
<223> OTHER INFORMATION: SP3L22-Trastuzumab scFv

<400> SEQUENCE: 113

Met Phe Asn Lys Arg His Ile Val Arg Thr Ile Ala Ala Thr Ala Ser
1               5                   10                  15

Ile Leu Ala Leu Ser Phe Thr Ala Ala Cys Gly Ser Gly Gln Ser Thr
            20                  25                  30

Ala Ser Asn Ser Thr Asp Ser Asp Ile Thr Gln Gln Thr Tyr Lys
        35                  40                  45

Pro Gly Lys Leu Thr Ile Ala Glu Val Gln Leu Val Glu Ser Gly Gly
50                  55                  60

Gly Leu Val Gln Pro Gly Gly Ser Leu Arg Leu Ser Cys Ala Ala Ser
65                  70                  75                  80

Gly Phe Asn Ile Lys Asp Thr Tyr Ile His Trp Val Arg Gln Ala Pro
                85                  90                  95

Gly Lys Gly Leu Glu Trp Val Ala Arg Ile Tyr Pro Thr Asn Gly Tyr
            100                 105                 110

Thr Arg Tyr Ala Asp Ser Val Lys Gly Arg Phe Thr Ile Ser Ala Asp
            115                 120                 125

Thr Ser Lys Asn Thr Ala Tyr Leu Gln Met Asn Ser Leu Arg Ala Glu
    130                 135                 140

Asp Thr Ala Val Tyr Tyr Cys Ser Arg Trp Gly Gly Asp Gly Phe Tyr
145                 150                 155                 160

Ala Met Asp Tyr Trp Gly Gln Gly Thr Leu Val Thr Val Ser Ser Gly
                165                 170                 175

Gly Gly Gly Ser Gly Gly Gly Gly Ser Gly Gly Gly Gly Ser Asp Ile
            180                 185                 190

Gln Met Thr Gln Ser Pro Ser Ser Leu Ser Ala Ser Val Gly Asp Arg
        195                 200                 205

Val Thr Ile Thr Cys Arg Ala Ser Gln Asp Val Asn Thr Ala Val Ala
    210                 215                 220

Trp Tyr Gln Gln Lys Pro Gly Lys Ala Pro Lys Leu Leu Ile Tyr Ser
225                 230                 235                 240

Ala Ser Phe Leu Tyr Ser Gly Val Pro Ser Arg Phe Ser Gly Ser Arg
                245                 250                 255

Ser Gly Thr Asp Phe Thr Leu Thr Ile Ser Ser Leu Gln Pro Glu Asp
            260                 265                 270

```
Phe Ala Thr Tyr Tyr Cys Gln Gln His Tyr Thr Thr Pro Pro Thr Phe
            275                 280                 285

Gly Gln Gly Thr Lys Val Glu Ile Lys His His His His His His
    290                 295                 300

<210> SEQ ID NO 114
<211> LENGTH: 20
<212> TYPE: PRT
<213> ORGANISM: Artificial
<220> FEATURE:
<223> OTHER INFORMATION: peptide fragment 1

<400> SEQUENCE: 114

Thr Glu Val Gln Leu Val Glu Ser Gly Gly Gly Leu Val Gln Pro Gly
1               5                   10                  15

Gly Ser Leu Arg
            20

<210> SEQ ID NO 115
<211> LENGTH: 19
<212> TYPE: PRT
<213> ORGANISM: Artificial
<220> FEATURE:
<223> OTHER INFORMATION: peptide fragment 2

<400> SEQUENCE: 115

Leu Ser Cys Ala Ala Ser Gly Phe Asn Ile Lys Asp Thr Tyr Ile His
1               5                   10                  15

Trp Val Arg

<210> SEQ ID NO 116
<211> LENGTH: 16
<212> TYPE: PRT
<213> ORGANISM: Artificial
<220> FEATURE:
<223> OTHER INFORMATION: peptide fragment 3

<400> SEQUENCE: 116

Gly Leu Glu Trp Val Ala Arg Ile Tyr Pro Thr Asn Gly Tyr Thr Arg
1               5                   10                  15

<210> SEQ ID NO 117
<211> LENGTH: 11
<212> TYPE: PRT
<213> ORGANISM: Artificial
<220> FEATURE:
<223> OTHER INFORMATION: peptide fragment 4

<400> SEQUENCE: 117

Asn Thr Ala Tyr Leu Gln Met Asn Ser Leu Arg
1               5                   10

<210> SEQ ID NO 118
<211> LENGTH: 55
<212> TYPE: PRT
<213> ORGANISM: Artificial
<220> FEATURE:
<223> OTHER INFORMATION: peptide fragment 5

<400> SEQUENCE: 118

Trp Gly Gly Asp Gly Phe Tyr Ala Met Asp Tyr Trp Gly Gln Gly Thr
1               5                   10                  15

Leu Val Thr Val Ser Ser Gly Gly Gly Gly Ser Gly Gly Gly Gly Ser
            20                  25                  30
```

```
Gly Gly Gly Gly Ser Asp Ile Gln Met Thr Gln Ser Pro Ser Ser Leu
        35                  40                  45

Ser Ala Ser Val Gly Asp Arg
    50                  55

<210> SEQ ID NO 119
<211> LENGTH: 24
<212> TYPE: PRT
<213> ORGANISM: Artificial
<220> FEATURE:
<223> OTHER INFORMATION: peptide fragment 6

<400> SEQUENCE: 119

Val Thr Ile Thr Cys Arg Ala Ser Gln Asp Val Asn Thr Ala Val Ala
1               5                   10                  15

Trp Tyr Gln Gln Lys Pro Gly Lys
            20

<210> SEQ ID NO 120
<211> LENGTH: 16
<212> TYPE: PRT
<213> ORGANISM: Artificial
<220> FEATURE:
<223> OTHER INFORMATION: peptide fragment 7

<400> SEQUENCE: 120

Leu Leu Ile Tyr Ser Ala Ser Phe Leu Tyr Ser Gly Val Pro Ser Arg
1               5                   10                  15
```

ANTIBODY GENE EXPRESSION-SECRETION SYSTEM

CROSS REFERENCE TO RELATED APPLICATIONS

This application is a National Phase under 35 USC 371 of International Application No. PCT/JP2015/002133 filed on Apr. 17, 2015, which claims priority to Japanese Application No. 2014-095440 filed May 2, 2014, the contents of which are hereby incorporated by reference in their entirety.

TECHNICAL FIELD

Sequence Listing

The present application contains a Sequence Listing that has been submitted in ASCII format via EFS-Web and is hereby incorporated by reference into the present specification in its entirety. The .txt file was created on Jan. 26, 2017; is named 7F003-002_SL.txt; and is 58 KB in size.

The present invention relates to a system for expressing an antibody gene and/or secretion, and more specifically to a DNA encoding a specific signal peptide used for secretion of antibodies such as Trastuzumab or a signal peptide-linker conjugate, a DNA insert comprising an antibody gene linked to the DNA, a vector having the DNA insert inserted thereinto, intestinal bacteria such as microorganisms of genus *Bifidobacterium* (bifidobacteria), which are transformed with the vector, etc.

BACKGROUND ART

Signal peptide is a sequence peptide, which comprises, dominantly, short hydrophobic amino acids (approximately 3 to 60 amino acids) in protein molecules and instructs secretion (transportation of the protein to endoplasmic reticulum). Such a signal peptide is also referred to as a "signal sequence," "localization signal," "transport (transfer) signal," etc.

As signal sequences of bifidobacteria, the signal sequences of secretory proteins, such as amylase of *Bifidobacterium adolescentis*, or Sec1, Sec2 and Sec3 of *Bifidobacterium breve*, have been reported, for example. In addition, the present inventors have proposed a signal sequence that can be applied to a plasmid for transformation of bifidobacteria (see, for example, Patent Documents 1 and 2).

Other than these, the genomic analysis of *Bifidobacterium longum* has also been reported (see, for example, Patent Document 3).

Moreover, there have been proposed: a method which comprises screening for an antibody gene expressed in cancer patient-derived B cells from a cancer antigen library derived from cultured cancer cells, so as to identify a more universal novel antibody gene against cancer antigens, without limitation of a source for collecting B cells (see, for example, Patent Document 4); a method of providing a gene library consisting of combinations of immunoglobulin light-chain variable region genes and heavy-chain variable region genes (see, for example, Patent Document 5); and a method of producing an antibody, which is capable of efficiently preparing a highly-versatile monoclonal antibody in a short time (see, for example, Patent Document 6), etc.

PRIOR ART DOCUMENTS

Patent Documents

Patent Document 1: WO 2011/093465
Patent Document 2: WO 2011/093467
Patent Document 3: EP1227152A1
Patent Document 4: Japanese unexamined Patent Application Publication No. 2010-35472
Patent Document 5: Japanese unexamined Patent Application Publication No. 2011-87586
Patent Document 6: Japanese unexamined Patent Application Publication No. 2006-180708

SUMMARY OF THE INVENTION

Object to be Solved by the Invention

It is an object of the present invention to provide signal sequence information capable of secreting an antibody to the outside of cells in generation of the antibody by bifidobacteria, an antibody expression vector capable of secreting an antibody to the outside of cells by utilizing the signal sequence information, and bifidobacteria which are transformed with the antibody expression vector and are capable of secreting an antibody.

Means to Solve the Object

It has been well known that a HER2 gene product (a cell division-stimulating receptor HER2 that is present on a cell surface) is overproduced by gene amplification in breast cancer, stomach cancer, prostate cancer and the like, and thus that such overproduction becomes a cancer exacerbation factor. In antibody therapy, and particularly, in antibody therapy for cancer, it is important to allow an antibody to locally express and/or secrete in cancer. Thus, the present inventors have used a plasmid for transformation of bifidobacteria having the signal sequence disclosed in the aforementioned Patent Document 1 or 2, with regard to a signal sequence that can be applied to a plasmid vector for transformation of bifidobacteria. As a result, it was found that secretion of antibodies is not sufficient. Hence, the inventors have studied novel signal sequences, and have found that *Bifidobacterium longum* transformed with a vector having inserted thereinto a DNA insert comprising a Trastuzumab single-chain antibody (scFv) gene linked to the 3'-terminus of a DNA encoding signal sequences named as SP27 and SP7 or of a signal peptide-linker conjugate having a linker sequence linked to such a signal sequence, efficiently secretes Trastuzumab to the outside of the cells, thereby completing the present invention.

Specifically, the present invention relates to the following:
[1] A DNA encoding a signal peptide consisting of an amino acid sequence described in the following a) or b):
a) an amino acid sequence shown in SEQ ID NO: 1 (SP27) or SEQ ID NO: 107 (SP7); or
b) an amino acid sequence comprising a deletion, substitution or addition of one or several amino acids, with respect to the amino acid sequence shown in SEQ ID NO: 1 or SEQ ID NO: 107, wherein a peptide consisting of the amino acid sequence functions as a signal peptide in *Bifidobacterium longum*,
[2] The DNA according to the above [1], consisting of a nucleotide sequence shown in SEQ ID NO: 2 (DNA encoding SP27) or SEQ ID NO: 108 (DNA encoding SP7),
[3] A DNA encoding a signal peptide-linker conjugate having a linker consisting of an amino acid sequence linked to the C-terminus of a signal peptide consisting of an amino acid sequence described in the following a) or b):

a) an amino acid sequence shown in SEQ ID NO: 1 or SEQ ID NO: 107; or
b) an amino acid sequence comprising a deletion, substitution or addition of one or two amino acids, with respect to the amino acid sequence shown in SEQ ID NO: 1 or SEQ ID NO: 107, wherein a peptide consisting of the amino acid sequence functions as a signal peptide in *Bifidobacterium longum*,

[4] The DNA according to the above [3], wherein the signal peptide-linker conjugate consists of an amino acid sequence shown in SEQ ID NO: 3 (SP27L6) or SEQ ID NO: 109 (SP7L20),

[5] The DNA according to the above [4], consisting of a nucleotide sequence shown in SEQ ID NO: 4 (DNA encoding SP27L6) or SEQ ID NO: 110 (DNA encoding SL7L20),

[6] A DNA insert, wherein the 5'-terminus of an antibody gene is linked to the 3'-terminus of the DNA according to any one of the above [1] to [5],

[7] The DNA insert according to the above [6], wherein the antibody gene is the gene of an antibody having an anticancer activity,

[8] The DNA insert according to the above [7], wherein the antibody having an anticancer activity is Trastuzumab,

[9] The DNA insert according to the above [8], wherein the Trastuzumab is a Trastuzumab single-chain antibody,

[10] A vector having the DNA insert according to any one of the above [6] to [9] inserted thereinto,

[11] An intestinal bacterium transformed with the vector according to the above [10],

[12] The intestinal bacterium according to the above [11], wherein the bacterium is a microorganism belonging to genus *Bifidobacterium*,

[13] The intestinal bacterium according to the above [12], wherein the microorganism belonging to genus *Bifidobacterium* is *Bifidobacterium longum*,

[14] An antibody drug composition comprising, as an active ingredient, the intestinal bacterium according to any one of the above [10] to [13], and

[15] The antibody drug composition according to the above [14], which is an anticancer agent composition.

Effect of the Invention

According to the present invention, by utilizing a DNA encoding a signal peptide or a signal peptide-linker conjugate, which is excellent in secretion of antibodies, bifidobacteria capable of efficiently secreting antibodies to the outside of the cells can be obtained. When the above described antibody is an antibody having an anticancer activity, such as Trastuzumab, such bifidobacteria is useful as an anticancer agent.

BRIEF DESCRIPTION OF DRAWINGS

FIG. 1 shows the structure of a Trastuzumab scFv secretion plasmid. Trastuzumab scFv-coding sequence was inserted into a shuttle plasmid for protein expression to produce recombinant bifidobacteria. For use in secretion, a secretion signal and a linker sequence were fused with the head of Trastuzumab scFv, and for use in detection of a Trastuzumab scFv protein, a histidine tag was fused with the C-terminus thereof. The structure of the plasmid is shown in FIG. 1. Using such a plasmid, bifidobacteria, *Bifidobacterium longum* 105A strain, was transformed.

FIG. 2 shows the whole nucleotide sequence of a Trastuzumab scFv antibody.

FIG. 3 shows the structure of a plasmid pSP1B-9.

FIG. 4 shows the structure of a PCR product by using a plasmid pHuSP1-Trastuzumab scFv as a template.

FIG. 5 shows the structure of Trastuzumab scFv in recombinant bifidobacteria detected by Western blot analysis. Using a culture supernatant of recombinant bifidobacteria, Western blot analysis was carried out. Detection was carried out using a histidine tag as an indicator. Bands were detected in three types of recombinant bifidobacteria (plasmid names: HuSP27L0-Trastuzumab scFv, HuSP27L6-Trastuzumab scFv, and HuSP3L22-Trastuzumab scFv).

FIG. 6 shows the results of analysis of the expression of Trastuzumab scFv in two types of bifidobacteria (HuSP27L6-Trastuzumab scFv and HuSP3L22-Trastuzumab scFv) by Western blotting.

FIG. 7 shows the results of SDS-PAGE for His tag-purified proteins. The above described three strains of recombinant bifidobacteria were cultured, and proteins were purified from culture supernatants, using a histidine tag-fused protein purification kit (TALON Metal Affinity Resin, manufactured by TAKARA BIO INC.). The purified proteins were electrophoresed in 4% to 20% polyacrylamide gel and were then stained, and bands were then cut out.

FIG. 8 shows the results of analysis of His tag-purified proteins by LC-MS/MS. The cut gel was destained, and was then subjected to cystine reduction by DTT, an alkylation treatment and a trypsin treatment, so that a peptide fragment was extracted from the gel. Using this peptide fragment solution, an LC-MS/MS analysis was carried out. The detected peptide was checked against database (the Trastuzumab scFv-coding sequence of the above described plasmid had previously been registered). Some peptide fragments matched with the amino acid sequence of Trastuzumab scFv were detected.

FIG. 9 shows peptide fragments matched with the amino acid sequence of Trastuzumab scFv as a result of the LC-MS/MS analysis.

FIG. 10 shows the construction of a Trastuzumab scFv secretion vector and the expression thereof in *E. coli*.

FIG. 11 shows the results of measurement of the affinity of Trastuzumab scFv with a HER2 extracellular domain by Biacore X100.

FIG. 12 shows the results of measuring the affinity of a Trastuzumab full-body antibody with a HER2 extracellular domain by Biacore X100.

FIG. 13 shows the results of a FACS analysis of the binding ability of Trastuzumab scFv and Trastuzumab full-body antibodies to human breast cancer cell lines.

FIG. 14 shows the in vivo dynamics of Cy5.5-labeled Trastuzumab scFv.

FIG. 15 shows the in vivo dynamics of a Cy5.5-labeled Trastuzumab full-body antibody.

FIG. 16 shows the antiproliferative effect of Trastuzumab scFv on an orthotropic grafted tumor of human breast cancer MDA-MB-361 cells.

FIG. 17 shows the results of an SDS-PAGE analysis of the expression of Trastuzumab scFv in bifidobacteria, *B. longum* 105A/pHuSP7L20-opt-Trastuzumab scFv.

FIG. 18 shows the binding of Trastuzumab scFv purified from *B. longum* 105A/pHuSP7L20-opt-Trastuzumab scFv to human breast cancer cell lines (HER2-positive line: SK-BR-3; and BT-474/HER2-negative line: SK-MEL-28) by immunostaining.

FIG. 19 shows the binding of Trastuzumab scFv purified from *B. longum* 105A/pHuSP7L20-opt-Trastuzumab scFv to human breast cancer cell lines (HER2-positive line:

SK-BR-3; and BT-474/HER2-negative line: SK-MEL-28) by a flow cytometric method.

FIG. 20 shows that Trastuzumab scFv purified from *B. longum* 105A/pP30SP7L20-opt-Trastuzumab scFv has a dose-dependent antiproliferative activity on BT474 breast cancer cells.

FIG. 21 shows the antitumor effect of B. longum 105A/pP30SP7L20-opt-Trastuzumab scFv on an orthotropic grafted tumor of a human stomach cancer cell line NCI-N87.

FIG. 22 shows localization of bacteria of genus *Bifidobacterium* in an orthotropic grafted tumor of a human stomach cancer cell line NCI-N87 by Gram staining.

FIG. 23 shows localization of Trastuzumab scFv in an orthotropic grafted tumor of a human stomach cancer cell line NCI-N87 by immunohistostaining using an anti-His-tag antibody.

MODE OF CARRYING OUT THE INVENTION

The signal peptide of the present invention is not particularly limited, as long as it is a signal peptide consisting of a) an amino acid sequence shown in SEQ ID NO: 1 (SP27) or SEQ ID NO: 107 (SP7), or a signal peptide (mutant signal peptide) consisting of b) an amino acid sequence comprising a deletion, substitution or addition of one or several amino acids, with respect to the amino acid sequence shown in SEQ ID NO: 1 or SEQ ID NO: 107, wherein a peptide consisting of the amino acid sequence functions as a signal peptide in *Bifidobacterium longum*. The above described "amino acid sequence comprising a deletion, substitution or addition of one or several amino acids" means an amino acid sequence in which, for example, 1 to 5, preferably 1 to 3, more preferably 1 or 2, and even more preferably one or any given number of amino acids are deleted, substituted or added. The above described mutant signal peptide has sequence identity of 90% or more, preferably 95% or more, and more preferably 98% or more with the amino acid sequence shown in SEQ ID NO: 1 or SEQ ID NO: 107.

The DNA of the present invention encoding the above described signal peptide consisting of a) an amino acid sequence shown in SEQ ID NO: 1 (SP27) or SEQ ID NO: 107 (SP7) is not particularly limited, as long as it is a DNA having a nucleotide sequence corresponding to the above described amino acid sequence. Thus, the DNA of the present invention also includes a DNA that is different due to degeneracy of a codon. A specific example of the present DNA is a DNA consisting of a nucleotide sequence shown in SEQ ID NO: 2 (DNA encoding SP27) or SEQ ID NO: 108 (DNA encoding SP7). These DNAs can be produced by any given method known to a person skilled in the art, such as chemical synthesis or a genetic engineering method.

The DNA of the present invention encoding the mutant signal peptide described in the above b) (mutant DNA) can also be produced by any given method known to a person skilled in the art, such as chemical synthesis, a genetic engineering method, or mutagenesis. Specifically, such mutant DNA can be obtained by introducing a mutation into a DNA consisting of the nucleotide sequence shown in SEQ ID NO: 2 (DNA encoding SP27) or SEQ ID NO: 108 (DNA encoding SP7) according to a method of allowing an agent serving as a mutagen to come into contact with the DNA, so that the drug is allowed to act on the DNA, or a method of irradiating the DNA with ultraviolet ray, or a genetic engineering method, etc. A genetic engineering method, site-directed mutagenesis, is useful because this is a method capable of introducing a specific mutation into a specific site, and the site-directed mutagenesis can be carried out according to the method described in Molecular Cloning: A laboratory Mannual, 2nd Ed., Cold Spring Harbor Laboratory, Cold Spring Harbor, N.Y., 1989. (hereinafter abbreviated as "Molecular Cloning 2nd Edition"), Current Protocols in Molecular Biology, Supplement 1 to 38, John Wiley & Sons (1987-1997), etc.

A linker (peptide) is preferably linked to the C-terminus of the signal peptide of the present invention. A linker that constitutes a signal peptide-linker conjugate having the linker linked to the C-terminus of the signal peptide means a peptide consisting of an amino acid sequence linking between the C-terminus of the above described signal peptide and the N-terminus of an antibody as a target protein. Such a linker can be appropriately selected from, for example, peptides existing in the C-terminus of the signal peptide. Moreover, a linker consisting of 0 to 30, preferably 3 to 25, and more preferably 5 to 15 amino acid residues is preferable. A linker consisting of an amino acid sequence shown in SEQ ID NO: 3 (SP27L6) or SEQ ID NO: 109 (SP7L20) is particularly preferable.

The DNA encoding the signal peptide-linker conjugate of the present invention is not particularly limited, as long as it is DNA having a nucleotide sequence corresponding to the amino acid sequence of the signal peptide-linker conjugate. Thus, it also includes a DNA that is different due to degeneracy of a codon. A specific example is a DNA consisting of a nucleotide sequence shown in SEQ ID NO: 4 (DNA encoding SP27L6) or SEQ ID NO: 110 (DNA encoding SP7L20). These DNAs can be produced by any given method known to a person skilled in the art, such as chemical synthesis, a genetic engineering method, or mutagenesis.

The DNA insert of the present invention is not particularly limited, as long as it is a DNA, wherein the 5'-terminus of an antibody gene is linked to the 3'-terminus of a DNA encoding the above described signal peptide of the present invention or a DNA encoding a signal peptide-linker conjugate. Such a DNA insert is inserted into an expression plasmid vector. A preferred example of the above described antibody gene is a DNA encoding a chimeric antibody-, humanized antibody-, or completely humanized antibody-type full-body antibody, Fc, Fab, Fab', F(ab')$_2$, a single-chain antibody (scFv), a disulfide stabilized antibody (dsFv), or the like. Such an antibody gene can be produced by a known method such as chemical synthesis or a genetic engineering method, based on its amino acid sequence information or nucleotide sequence information (see, for example, Patent Documents 4 to 6).

Among the above described antibody genes, the gene of an antibody having an anticancer activity is preferable. Herein, examples of the antibody having an anticancer activity include monoclonal antibodies produced against a molecule called a tumor-related antigen, which is expressed on a cancer cell membrane, receptors of various types of growth factors, molecules of a cluster of differentiation of leukocytes (CD), or the like. As a main mechanism of antitumor action, the reinforcement of the cancer-killing ability of NK cells by the enhancement of ADCC (antibody-dependent cytotoxicity) cellular activity caused by an antibody-antigen bond has been known. Specific examples of the antibody having an anticancer activity include: an anti-human CD20 human-mouse chimeric monoclonal antibody, rituximab; an anti-HER2 humanized monoclonal antibody, Trastuzumab; an anti-human CD52 humanized monoclonal antibody, alemtuzumab; an anti-human epithelial growth factor receptor (EGFR) chimeric monoclonal antibody, cetuximab; and an anti-human vascular endothelial growth factor (VEGF) humanized monoclonal antibody, bevacizumab. The single-chain antibodies of these antibodies, and in particular, a Trastuzumab single-chain antibody is preferable.

The vector of the present invention is not particularly limited, as long as it is an expression plasmid vector suitable for host cells, having the above described DNA insert of the present invention inserted thereinto. Intestinal bacteria, preferably microorganisms belonging to genus *Bifidobacterium*, and among others, *Bifidobacterium longum*, which is able to express the DNA insert of the present invention, is preferable. Moreover, a shuttle vector autonomously replicating in two or more different types of organism hosts is preferable. More preferred examples of such a shuttle vector include: a shuttle vector pBLES100 constructed from pTB6 of *Bifidobacterium longum* BK51 disclosed in the publication of Matsumura et al. [Matsumura et al., Biosci. Biotechnol. Biochem., 61, 1211-1212 (1997)] and pBR322 of *E. coli*; shuttle vectors pAV001 and pBRASTA101 disclosed in the publication of Tanaka et al. [Tanaka et al., Biosci Biotechnol Biochem.; 69(2): 422-425 (2005, February)]; and a pBE-S DNA shuttle vector (manufactured by TAKARA BIO INC.), which is constructed from *E. coli* and *B. subtilis* used in a BIC method (Brevibacillus In vivo Cloning method) and which is capable of expressing in Gram-positive bacteria a secretory protein derived from a eukaryote, having an S—S bond in molecules. Furthermore, the above described expression plasmid vector optionally comprises a promoter, a terminator, and a drug resistance gene as a marker gene.

In addition, utilizing a screening system for a signal peptide used for a target antibody high secretion-expression system, the above described expression plasmid vector can be selected and/or evaluated as follows. A vector, which comprises a promoter su ch as a *Bifidobacterium longum* hup promoter (Hu promoter) or a *Bifidobacterium longum* 105A P30 promoter (P30 promoter), and also comprises a DNA encoding a secretion signal peptide, a multicloning site (MCS) and a His tag sequence downstream of the promoter, and into the MCS of which a target antibody gene is inserted, and which is thereafter cleaved with restriction enzyme to be linearized, and the In-Fusion cloning system of Clontech, etc. are used, and the amount of an antibody secreted from bifidobacteria transformed with a vector, into which the DNA of the present invention encoding a secretion signal peptide suitable for the target antibody, etc. has been inserted, is measured, so that an available expression plasmid vector can be selected.

The intestinal bacteria of the present invention are not particularly limited, as long as they are intestinal bacteria transformed with the above described vector of the present invention. The intestinal bacteria as host cells are normal bacteria mainly comprising obligate anaerobic bacteria living in the intestinal portions of humans or animals. Specific examples of the intestinal bacteria include Gram-positive lactic acid bacteria such as bacterium of the genus *Lactobacillus* or bacterium of the genus *Bifidobacterium*, and Gram-negative bacteria such as bacterium of the genus Clostridium, *E. coli*, or bacterium of the genus Bacteroides. Among others, bifidobacteria are preferable.

Specific examples of the above described bifidobacteria include *Bifidobacterium longum*, *B. breve*, *B. adolescentis*, *B. bifidum*, *B. pseudolongum*, *B. thermophirum*, *B. infantis*, *B. animalis*, *B. angulatum*, *B. asteroides*, *B. boum*, *B. catenulatum*, *B. choerinum*, *B. coryneforme*, *B. cuniculi*, *B. denticolens*, *B. dentium*, *B. gallicum*, *B. gallinarum*, *B. globosum*, *B. indicum*, *B. inopinatum*, *B. lactis*, *B. lactentis*, *B. magnum*, *B. merycicum*, *B. minimum*, *B. Mongolia Enns*, *B. parvulorum*, *B. pseudocatenulatum*, *B. psychraerophilum*, *B. pullorum*, *B. ruminale*, *B. ruminantium*, *B. saeculare*, *B. scardovii*, *B. subtile*, *B. suis*, and *B. thermacidophilum*. Among others, *Bifidobacterium longum*, *Bifidobacterium breve*, *Bifidobacterium adolescentis*, *Bifidobacterium bifidum*, and *Bifidobacterium infantis*, which have been known to normally exist in human intestine, regardless of age, are preferably used as host cells, and further, *Bifidobacterium longum* is more preferably used. All of these bacteria are commercially available, or can be easily obtained from depositary institutions. For example, *Bifidobacterium longum* ATCC-15707, *Bifidobacterium bifidum* ATCC-11863, and *Bifidobacterium infantis* ATCC-15697 can be used.

Moreover, the strains of such bifidobacteria are not particularly limited, either. Preferred examples of the *Bifidobacterium longum* strain include *Bifidobacterium longum* 105A, *Bifidobacterium longum* aE-194b, *Bifidobacterium longum* bs-601, and *Bifidobacterium longum* M101-2. Among these strains, *Bifidobacterium longum* 105A is preferable. Examples of the *Bifidobacterium breve* strain include a *Bifidobacterium breve* standard strain (JCM1192), *Bifidobacterium breve* aS-1, and *Bifidobacterium breve* I-53-8W. Among these strains, the *Bifidobacterium breve* standard strain and *Bifidobacterium breve* aS-1 are preferable. Examples of the *Bifidobacterium infantis* strain include a *Bifidobacterium infantis* standard strain (JCM1222) and *Bifidobacterium infantis* I-10-5. Among these strains, the *Bifidobacterium infantis* standard strain and *Bifidobacterium infantis* I-10-5 are preferable. An example of the *Bifidobacterium lactentis* strain is a *Bifidobacterium lactentis* standard strain (JCM1210).

Examples of the method of introducing a vector into intestinal bacteria in the present invention include an electroporation method, an In-Fusion cloning system (Clontech), a liposome method, a lipofection method, a microinjection method, a DEAE-dextran method, and a calcium phosphate method. Among these methods, the electroporation method is preferable. Moreover, methods of using commercially available transfection reagents, such as Lipofectin Reagent (registered trademark), Lipofectamine (registered trademark), Lipofectamine (registered trademark) 2000 Reagent (manufactured by Invitrogen), SuperFect (registered trademark) Transfection Reagent (manufactured by QIAGEN), FuGENE (registered trademark) HD Transfection Reagent (manufactured by Roche Diagnostics), and FuGENE (registered trademark) 6 Transfection Reagent (manufactured by Roche Diagnostics), which have been widely applied in the art, can be applied.

The above described intestinal bacteria of the present invention can be used as an antibody drug, and the intestinal bacteria of the present invention transformed with a DNA insert comprising the gene of an antibody having an anticancer activity can be used as an anticancer agent. Accordingly, the antibody drug composition of the present invention is not particularly limited, as long as it comprises, as an active ingredient, the above described intestinal bacteria of the present invention that is capable of secreting an antibody, and preferably, an antibody having an anticancer activity. The present antibody drug composition optionally comprises any given components, such as a pharmacologically acceptable carrier, an excipient, and a diluent, unless these components impair the action and/or effect of a secreted antibody.

The dosage form of the antibody drug composition of the present invention includes a liquid agent or a solid preparation. Such a liquid agent can be produced by purifying a culture solution of the intestinal bacteria of the present invention, then adding, as necessary, a suitable physiological saline or fluid replacement, or pharmaceutical additives, and then filling an ampule or vial bottle, etc. with the obtained mixture. On the other hand, such a solid preparation can be produced by adding a suitable protective agent to the liquid agent, then filling an ampule or vial bottle, etc. with the obtained mixture, and then freeze-drying it, or adding a suitable protective agent to the liquid agent, then freeze-drying it, and then filling an ampule or vial bottle, etc. with the resultant. As a method of administering the antibody drug composition of the present invention to a subject, both oral administration and parenteral administration are applicable. Of these, parenteral administration is preferable, and examples of the parenteral administration include intravenous injection, subcutaneous injection, local injection, and intraventricular administration. Among these, intravenous injection is most preferable.

The dose of the antibody drug composition of the present invention is not particularly limited, as long as it is an amount sufficient for growth in diseased site and the expression of an effective therapeutic amount of active antibody. The dose of the present antibody drug composition is selected, as appropriate, depending on the degree of disease, and the body weight, age and sex of a patient, and the dose can be increased or decreased, as appropriate, depending on the degree of amelioration. From the viewpoint of economic efficiency and from the viewpoint of prevention of side effects as much as possible, the applied dose of the present antibody drug composition is preferably as low as possible within a range in which necessary therapeutic effects can be obtained.

For example, in particular, since intravenous administration is required to reduce the risk of embolism caused by cell masses, etc., it is preferable that a possible lowest concentration of injection preparation be dispensed dividedly over several administrations, or that the injection be diluted with a suitable fluid replacement and the thus diluted solution be continuously injected. In the case of an adult for example, the cells of the intestinal bacteria of the present invention, which are in an amount of $10^6$ to $10^{12}$ cfu per kg of body weight, are administered once a day, or dividedly over several administrations a day, for one to several days, continuously or at appropriate intervals. More specifically, 1 to 1000 mL of a preparation comprising the cells of the microorganisms of genus *Bifidobacterium* of the present invention at a concentration of $10^4$ to $10^{10}$ cfu/mL is administered to an adult, directly or by being diluted with a suitable fluid replacement, once a day or divided over several administrations a day, continuously for one to several days.

Moreover, in the case of local administration in which the intestinal bacteria are directly administered to diseased tissues, it is required for the bacteria to engraft to the entire diseased tissues as much as possible and to grow there. Thus, it is desired to administer a high concentration of injection to several sites in diseased tissues. In the case of an adult for example, the cells of the microorganisms of genus *Bifidobacterium* of the present invention are administered at a dose of $10^6$ to $10^{12}$ cfu per kg of body weight once or several times a day, as necessary for one to several days, continuously or at appropriate intervals. More specifically, 1 to 1000 mL of a preparation comprising the cells of the bifidobacteria of the present invention at a concentration of $10^4$ to $10^{10}$ cfu/mL is directly administered to an adult, several times a day, as necessary, continuously for one to several days.

When the antibody drug composition of the present invention is an anticancer agent composition, it can be applied, for example, to large bowel cancer, brain tumor, head and neck cancer, breast cancer, lung cancer, esophageal cancer, stomach cancer, liver cancer, gallbladder cancer, bile duct cancer, pancreatic cancer, islet cell carcinoma, choriocarcinoma, colon cancer, renal cell carcinoma, adrenal cortex cancer, bladder cancer, testicular cancer, prostate cancer, testicular tumor, ovary cancer, uterine cancer, choriocarcinoma, thyroid cancer, malignant carcinoid tumor, skin cancer, malignant melanoma, osteosarcoma, soft tissue sarcoma, neuroblastoma, Wilms' tumor, retinoblastoma, melanoma, squamous cell carcinoma, etc.

EXAMPLES

Hereinafter, the present invention will be more specifically described in the following examples. However, these examples are not intended to limit the technical scope of the present invention.

Example 1

1. Construction of Secretory Trastuzumab scFv Expression Plasmid (pHuSPx-Trastuzumab scFv)

A plasmid for expressing secretory Trastuzumab scFv (anti-HER2 low molecular weight single-chain antibody [scFv]) in a histone-like promoter (Hu promoter) of bifidobacteria was constructed. First, a plasmid pHuSP1-Trastuzumab scFv was produced by linking Trastuzumab scFv to a signal peptide 1 (SP1), and thereafter, pHuSPx-Trastuzumab scFv was produced by the replacement of the signal peptide portion. A summary of the production of the plasmid is shown in FIG. 1. The details are as follows.

2. Preparation of Insert in Production of pHuSP1-Trastuzumab scFv

A Trastuzumab scFv insert was prepared as follows. First, the amino acid sequence of a Trastuzumab full-body antibody was downloaded from RCSB Protein data bank (PDB) (http://www.pdb.org/pdb/home/home.do) (PDB 1N8Z). The DNAs of VH, VL and a linker sequence were determined based on the cDNA sequences registered in the PDB database (FIG. 2) (SEQ ID NOS: 5 to 11). Using, as a template, a plasmid pOZ Trastuzumab scFv-His prepared by inserting this Trastuzumab scFv-coding sequence (comprising a His-tag sequence at the terminus thereof) into a pOZ1 vector, PCR was carried out. As primers, Trastuzumab scFv_ins_F3 primer (SEQ ID NO: 14) and Trastuzumab scFv_ins_R2 primer (SEQ ID NO: 15) (Table 1; 15 nucleotides on the 5'-terminal side of each primer have a sequence homologous to a vector as shown below) were used, and a Trastuzumab scFv-coding region was amplified to obtain a 777-bp insert PCR product. Using 2.0% agarose gel (1×TEB buffer, containing ethidium bromide), the insert PCR product, together with a DNA concentration marker, was subjected to electrophoresis, so that the concentration was estimated.

TABLE 1

| SEQ ID NO: | | Name of primer | Sequence (5' → 3') | Template plasmid |
|---|---|---|---|---|
| 12 | Primers for preparation of vector | SP1_Vec_F3 | CCTTCTGCTCGTAGCGATTAC | SP1B-9 (SEQ ID NO: 16) |
| 13 | | SP1_Vec_R2 | TTCCACGCGCTCCTTGG | |
| 14 | Primers for preparation of Trastuzumab insert (In-Fusion) | Trastuzumab scFv_ins_INF_F3 | aaggagcgcgtggaaGAAGTTCAGCTGGTTGAAAGC | pOZ Trastuzumab scFv-His |
| 15 | | Trastuzumab scFv_ins_INF_R2 | gctacgagcagaaggTTAATGATGGTGATGATGATGTTTAATTTC | |

Small letters indicate 15-nucleotide sequence complementary to vector 5'-terminus added to target gene amplification primer for In-Fusion cloning 3. Preparation of Vector in Production of pHuSP1-Trastuzumab scFv A vector was prepared as follows. Using, as a template, a plasmid pSP1B-9 (comprising a GFPuv gene, a replication origin of E. coli, a replication origin of bifidobacteria, and a spectinomycin resistance gene (FIG. 3) (SEQ ID NO: 16)), PCR was carried out. Using, as primers, SP1_Vec_F3 primer (SEQ ID NO: 12) and SP1_Vec_R2 primer (SEQ ID NO: 13) (Table 1), a region, from which the GFPuv gene was excluded, was amplified to obtain a 3983-bp vector PCR product (PrimeSTAR; registered trademark: HS Premix, manufactured by TAKARA BIO INC.). Using 0.8% agarose gel (1×TEB buffer, containing ethidium bromide), the vector PCR product, together with a DNA concentration marker, was subjected to electrophoresis, so that the concentration was estimated.

4. Fusing of Insert to Vector by In-Fusion Reaction in Production of pHuSP1-Trastuzumab scFv Using In-Fusion (registered trademark) HD Cloning Kit with Cloning Enhancer (manufactured by Clontech), the insert PCR product was fused to the vector PCR product. First, referring to the website of Clontech, In-Fusion (registered trademark) Molar Ratio Calculator (http://bioinfo.clontech.com/infusion/molarRatio.do), necessary amounts of the insert and the vector were calculated. Two μL of 5× In-Fusion HD Enzymes premix, 1 μL of Cloning Enhancer, and necessary amounts of the insert and the vector were mixed with one another, and sterilized water was then added to the obtained mixture, so that a total amount of the reaction system was adjusted to 10 μL. After completion of a reaction at 37° C. for 15 minutes, the reaction product was treated at 50° C. for 15 minutes and was then left at rest at 4° C.

5. Transformation of E. coli, Plasmid Extraction and Sequencing in Production of pHuSP1-Trastuzumab scFv Using 2 μL of In-Fusion reaction solution, E. coli TOP10 chemically Competent Cell (manufactured by Invitrogen) was transformed, and the resultant was then transferred onto an LB (75 μg/mL, containing spectinomycin) plate, followed by performing a culture at 37° C. overnight. Conditions for the transformation were as described in the product instruction. The transformed E. coli colonies were cultured in an LB (75 μg/mL, containing spectinomycin) liquid medium at 37° C. overnight, and a plasmid was then extracted from the culture (QIAprep Spin Miniprep Kit, manufactured by QIAGEN). It was confirmed that the whole nucleotide sequence of this plasmid was as designed, and the plasmid was designated as a plasmid pHuSP1-Trastuzumab scFv.

6. Preparation of Inserts (SP2 to SP10, SP12 to SP16, SP19, and SP21 to SP27) in production of pHuSPx-Trastuzumab scFv (x=2 to 10, 12 to 16, 19, and 21 to 27), involving replacement of signal peptide PCR was carried out using, as a template, a plasmid comprising each signal peptide, so as to prepare an insert. Using the primers (wherein 15 nucleotides on the 5'-terminal side of each primer have a sequence homologous to a vector as shown below) and the templates shown in Table 2, PCR was carried out to obtain each insert PCR product. Using 2.0% agarose gel, the insert PCR product, together with a DNA concentration marker, was subjected to electrophoresis, so that the concentration was estimated.

TABLE 2

| SEQ ID NO: | | Name of primer | Sequence (5'→3') | Template plasmid |
|---|---|---|---|---|
| 17 | Primers for preparation of vector | Hu-Trastuzumab_vec_F1 | GAAGTTCAGCTGGTTGAAAGCGG | pHuSF1-Trastuzumab (SEQ ID NO: 67) |
| 18 | | Hu-Vec_R1 | AAAGCATCCTTCTTGGGTCAGG | |
| 19 | Primers for preparation of SP insert (In-Fusion) | SP2B_ins_INF_F1 | caagaaggatgctttGTGGGTATGACTGAGAACGC | SP2B-3 (SEQ ID NO: 68) |
| 20 | | SP2B-Trastuzumab_ins_INF_R1 | aaccagctgaacttcCAAAAACAGCACGCGG | |
| 21 | | SP313_ins_INF_F1 | caagaaggatgctttATGTTCAATAAGCGACACATCG | SP3B-4 (SEQ ID NO: 69) |
| 22 | | SP3B-Trastuzumab_ins_INF_R1 | aaccagctgaacttcGGCGATGGTCAGCTTGC | |
| 23 | | SP413_ins_INF_F1 | caagaaggatgattATGACCACTCACAAGAGCCAG | SP4B-1 (SEQ ID NO: 70) |
| 24 | | SP4B-Trastuzumab_ins_INF_R1 | aaccagctgaacttcGCCGAACAGACGCGG | |
| 25 | | SP5B_ins_INF_F1 | caagaaggatgctttATGACCGCGATTGACGAG | SP58-2 (SEQ ID NO: 71) |
| 26 | | SP5B-Trastuzumab_ins_INF_R1 | aaccagctgaacttcTTGGTCGATGATGGCCTTG | |
| 27 | | SP6B_ins_INF_F1 | caagaaggatgctttATGAAGATTGCGGTTGCAG | SP6B-1 (SEQ ID NO: 72) |
| 28 | | SP6B-Trastuzumab_ins_INF_R1 | aaccagctgaacttcATCGACAATAGGACTTTTCCCATTG | |
| 29 | | SP7B_ins_INF_F1 | caagaaggatgctttATGTTTGCGTGCGTAGCC | SP7B-1 (SEQ ID NO: 73) |
| 30 | | SP7B-Trastuzumab_ins_INF_R1 | aaccagctgaacttcGGTGGAGGTGGATTCGG | |
| 31 | | SP8B_ins_INF_F1 | caagaaggatgctttATGGTTGGTGACGACACCG | SP8B-1 (SEQ ID NO: 74) |
| 32 | | SP8B-Trastuzumab_ins_INF_R1 | aaccagctgaacttcCATCGTTGCCTCGCC | |

TABLE 2 -continued

| SEQ ID NO: | Name of primer | Sequence (5'→3') | Template plasmid |
|---|---|---|---|
| 33 | SP9B_ins_INF_F1 | caagaaggatgctttATGGGCACCATGATGCG | SP9B-1 |
| 34 | SP9B-Trastuzumab_ins_INF_R1 | aaccagctgaacttcGACGATCTGATGCGCCAG | (SEQ ID NO: 75) |
| 35 | SP10B_ins_INF_F1 | caagaaggatgctttATGATGACTGGTGCACAGGC | SP10B-1 |
| 36 | SP10B-Trastuzumab_ins_INF_R1 | aaccagctgaacttcTCGCTGCTTGAGTTTGCC | (SEQ ID NO: 76) |
| 37 | SP12B_ins_INF_F1 | caagaaggatgctttATGGTGTCTTTCAATAAACTGACC | SP12B-2 |
| 38 | SP12B-Trastuzumab_ins_INF_R1 | aaccagctgaacttcGGAACGGGTCCACAGGGT | (SEQ ID NO: 77) |
| 39 | SP13B_ins_INF_F1 | caagaaggatgctttATGGTCGCCGTCCTCAG | SP13B-1 |
| 40 | SP13B-Trastuzumabins_INF_R1 | aaccagctgaacttcAGACTCGCTAGCACAGCACAG | (SEQ ID NO: 75) |
| 41 | SP14B_ins_INF_F1 | caagaaggatgctttTTGCCGGGACCTATATGTCC | SP14B-3 |
| 42 | SP14B-Trastuzumab_ins_INF_R1 | aaccagctgaacttc TTGGGCCACTATTGTCTTCTG | (SEQ ID NO: 78) |
| 43 | SR15B_ins_INF_F1 | caagaaggatgctttATGAAACGTAGCGATTATATGTTGG | SP15B-2 |
| 44 | SP15B-Trastuzumab_ins_INF_R1 | aaccagctgaacttcCTTGCCTGAGGCATCTTGAATC | (SEQ ID NO: 80) |
| 45 | SP16B_ins_INF_F1 | caagaaggatgattATGAGCAATAGTGCATCATCGTTTAC | SP16B-2 |
| 46 | SP16B-Trastuzumab_ins_INF_R1 | aaccagctgaacttcGGCCAACGGAGTCGTCTC | (SEQ ID NO: 81) |
| 47 | SP19B_ins_INF_F1 | caagaaggatgctttTTGGCAAGATGGGTCACTC | SP19B-4 |
| 48 | SP19B-Trastuzumab_ins_INF_R1 | aaccagctgaacttcGCCCATGACCGGCATG | (SEQ ID NO: 82) |
| 49 | SP21B_ins_INF_F1 | caagaaggatgctttATGGCATTGACTGGTGAACAGG | SP21B-1 |
| 50 | SP21B-Trastuzumab_ins_INF_R1 | aaccagctgaacttcACGTGCAGTGGTATGGATGATT | (SEQ ID NO: 83) |
| 51 | SP22B_ins_INF_F1 | caagaaggatgctttTTGGTGTCTATGAGAAGCCCAC | SP22B-2 |
| 59 | SP22B-Trastuzumab_ins_INF_R1 | aaccagstgaacttsGATGCGCTCACGCTTGG | (SEQ ID NO: 84) |
| 53 | SP23B_ins_INF_F1 | caagaaggatgctttATGAACAAGCGATGGAACAAAC | SP23B |
| 54 | SP23B-Trastuzumab_ins_INF_R1 | aaccagctgaacttcGATCGTCTTGAGAATCTTCAGACG | (SEQ ID NO: 85) |
| 55 | SP24B_ins_INF_F1 | caagaaggatgctttATGGTCGGCATGCGC | SP24B-4 |
| 56 | SP24B-Trastuzumab_ins_INF_R1 | aaccagctgaacttcGTTGGTGCGGTTCCGG | (SEQ ID NO: 86) |
| 57 | SP25B_ins_INF_F1 | caagaaggatgctttGTGATGTTATCCACACCCTCCA | SP25B-3 |
| 58 | SP25B-Trastuzumab_ins_INF_R1 | aaccagctgaacttcCTGCTCATGATCGGCCCA | (SEQ ID NO: 67) |
| 59 | SP26_HU_ins_INF_F1 | caagaaggatgctttATGAAGAAGAAAGCTCTTGCTTTCG | SP26-1 |
| 60 | SP26_L0-Trastuzumab_ins_INF_R1 | aaccagctgaacttcAGCGTTGCTGTTGGAGCC | (SEQ ID NO: 88) |
| 61 | SP26_HU_ins_INF_F1 | caagaaggatgctttATGAAGAAGAAAGCTCTTGCTTTCG | SP26-2 |
| 62 | SP26_L5-Trastuzumab_ins_INF_R1 | aaccagctgaacttcGGTGTCACCGGAGGCAG | (SEQ ID NO: 89) |
| 63 | SP27_HU_ins_INF_F1 | aaccagctgaacttcATGAACACCATTCGTCGCATC | SP27-3 |
| 64 | 5P27_L0-Trastuzumab_ins_INF_R1 | aaccagctgaacttcCGCTTGTGCGGTTTGAC | (SEQ ID NO: 90) |
| 65 | SP27_HU_ins_INF_F1 | caagaaggatgctttATGAACACCATTCGTCGCATC | SP27-4 |
| 66 | 5P27_L6-Trastuzumab_ins_INF_R1 | aaccagctgaacttcGGTGCGGTTAGCCGTG | (SEQ ID NO: 91) |

Small letters indicate 15-nucleotide sequence complementary to vector 5'-terminus added to target gene amplification primer for In-Fusion cloning 7. Preparation of Vectors (SP2 to SP10, SP12 to SP16, SP19, and SP21 to SP27) in Production of pHuSPx-Trastuzumab scFv (x=2 to 10, 12 to 16, 19, and 21 to 27), Involving Replacement of Signal Peptide PCR was carried out using the plasmid pHuSP1-Trastuzumab scFv as a template, so as to prepare a vector. Using, as primers, Hu-Trastuzumab_vec_F1 primer (SEQ ID NO: 17) and Hu-vec_R1 primer (SEQ ID NO: 18) (Table 2), a region, from which the signal peptide portion (SP1) was excluded, was amplified to obtain a 4589-bp vector PCR product (FIG. 4; comprising a Trastuzumab scFv gene, a replication origin of E. coli, a replication origin of bifidobacteria, and a spectinomycin resistance gene). Using 0.8% agarose gel, the vector PCR product, together with a DNA concentration marker, was subjected to electrophoresis, so that the concentration was estimated.

8. Linking of Inserts to Vectors by In-Fusion Reaction (SP2 to SP10, SP12 to SP16, SP19, and SP21 to SP27) in Production of pHuSPx-Trastuzumab scFv (x=2 to 10, 12 to 16, 19, and 21 to 27), Involving Replacement of Signal Peptide Using In-Fusion (registered trademark) HD Cloning Kit with Cloning Enhancer (manufactured by Clontech) in the same manner as that described above, the insert PCR products were linked to the vector PCR products.

9. Transformation of E. coli, Plasmid Extraction and Sequencing (SP2 to SP10, SP12 to SP16, SP19, and SP21 to SP27) in Production of pHuSPx-Trastuzumab scFv (x=2 to 10, 12 to 16, 19, and 21 to 27), involving replacement of signal peptide Using 1 μL of In-Fusion reaction solution, E. coli TOP10 chemically Competent Cell (manufactured by Invitrogen) was transformed, and the resultant was then transferred onto an LB (75 μg/mL, containing spectinomycin) plate, followed by performing a culture at 37° C. overnight. Conditions for the transformation were as described in the product instruction. The transformed E. coli colonies were cultured in an LB (75 μg/mL, containing spectinomycin) liquid medium at 37° C. overnight, and a plasmid was then extracted from the culture (QIAprep Spin Miniprep Kit, manufactured by QIAGEN). It was confirmed that the nucleotide sequence of this plasmid ranging from the vicinity of a Hu promoter to the vicinity of a terminator was as designed. The produced plasmids are shown in Table 3.

TABLE 3

Produced plasmids

| No. | Plasmid *[1] | Cleavage site by Signal P *[2] |
|---|---|---|
| 1 | pHuSP1-Trastuzumab scFv | Non |
| 2 | pHuSP2-Trastuzumab scFv | Non |
| 3 | pHuSP3L22-Trastuzumab scFv | 33/34 |
| 4 | pHuSP4-Trastuzumab scFv | Non |
| 5 | pHuSP5-Trastuzumab scFv | Non |
| 6 | pHuSP6-Trastuzumab scFv | Non |
| 7 | pHuSP7-Trastuzumab scFv | Non |
| 8 | pHuSP8-Trastuzumab scFv | Non |
| 9 | pHuSP9-Trastuzumab scFv | Non |
| 10 | pHuSP10-Trastuzumab scFv | Non |
| 11 | pHuSP12L20-Trastuzumab scFv | 37/38 |
| 12 | pHuSP13-Trastuzumab scFv | Non |

TABLE 3-continued

Produced plasmids

| No. | Plasmid *1 | Cleavage site by Signal P *2 |
|---|---|---|
| 13 | pHuSP14L20-Trastuzumab scFv | 42/43 |
| 14 | pHuSP15L20-Trastuzumab scFv | 30/31 |
| 15 | pHuSP16-Trastuzumab scFv | Non |
| 16 | pHuSP19L43-Trastuzumab scFv | 22/23 |
| 17 | pHuSP21-Trastuzumab scFv | Non |
| 18 | pHuSP22-Trastuzumab scFv | Non |
| 19 | pHuSP23L27-Trastuzumab scFv | 33/34 |
| 20 | pHuSP24-Trastuzumab scFv | Non |
| 21 | pHuSP25-Trastuzumab scFv | Non |
| 22 | pHuSP26L0-Trastuzumab scFv | 21/22 |
| 23 | pHuSP26L5-Trastuzumab scFv | 21/22 |
| 24 | pHuSP27L0-Trastuzumab scFv | 52/53 |
| 25 | pHuSP27L6-Trastuzumab scFv | 52/53 |

*1 Regarding names of plasmids e.g.) pHuSP3L22-Trastuzumab scFv
p indicates p of plasmid
Hu indicates Hu promoter
SP indicates signal peptide, having original serial number
L indicates the number of linkers, namely, the number of amino acids between signal peptide cleavage prediction site and target protein (in this case, there are 22 amino acids between cleavage prediction site and Trastuzumab scFv)
Finally, name of target protein (in this case, Trastuzumab scFv)
*2 Cleavage prediction site analyzed with secretion signal cleavage site prediction software SignalP Ver4.0
When there are no cleavage prediction sites, plasmid name does not include Lxx because the number of linkers cannot be determined 10. Transformation of Bifidobacteria (SP2 to SP10, SP12 to SP16, SP19, and SP21 to SP27) in Production of pHuSPx-Trastuzumab scFv (x=2 to 10, 12 to 16, 19, and 21 to 27), Involving Replacement of Signal Peptide Using 1.5 to 3 µL of plasmid DNA extracted from the transformed *E. coli* (Table 3), bifidobacteria, *Bifidobacterium longum* 105A, was transformed according to an electroporation system (Gene Pulser II, manufactured by Bio-Rad Laboratories). After completion of the electric shock, a mixed solution of 800 µL of IMR liquid medium and 50 µL of vitamin C-added solution was immediately added to a cuvette, and it was then recovered into a 2-mL sterilized microtube. The same operations as described above were carried out on each tube, and the cap of each 2-mL tube was then loosened. The resulting solution, together with AneroPack, was placed in a hermetically sealed vessel, it was then placed in an incubator that had been set at 37° C., and it was then incubated for 3 hours. After completion of the incubation, each suspension was fully mixed, and 100 µL of the mixed suspension was taken and was then each applied to one IMR agar medium (containing 75 µg/mL SPCM). Such an agar medium, together with a deoxidant/carbon dioxide generator (AneroPack-Kenki, manufactured by Mitsubishi Gas Chemical Company), was placed in a hermetically sealed vessel, and was then cultured in an incubator that had been set at 37° C. for 2 to 3 days. The colonies growing on the plate were picked up with a disposable stick, and were then streaked on a BL-bS agar medium (containing 75 µg/mL SPCM). The medium, together with a deoxidant/carbon dioxide generator (AneroPack-Kenki, manufactured by Mitsubishi Gas Chemical Company), was placed in a hermetically sealed vessel, and was then cultured in an incubator that had been set at 37° C. for 1 day, so as to obtain a streaked culture.

11. Western Blot Analysis of Culture Supernatant and Intracellular Protein

The above-obtained streaked culture of recombinant bifidobacteria (*Bifidobacterium longum* 105A/pHuSPx-Trastuzumab scFv (x=2 to 10, 12 to 16, 19, and 21 to 27)) was inoculated into an APS-2S-2.5SE (75 µg/mL, spectinomycin) liquid medium, and it was then subjected to an anaerobic culture at 37° C. for 24 hours (activated culture solution). Subsequently, 0.5% activated culture solution was inoculated in a medium prepared by adding spectinomycin to a DMEM (low glucose, pyruvic acid, and HEPES) culture medium for cell culture (manufactured by Life Technologies cat #12320-032): APS-2S-2.5SE (=9:1) to a concentration of 75 µg/mL. The thus obtained mixture was subjected to an anaerobic culture at 37° C. for 15 hours. Using this culture solution, a culture supernatant and an intracellular protein were prepared as follows. After the culture solution had been centrifuged, a culture supernatant was recovered. The protein in this culture supernatant was precipitated with trichloroacetic acid (TCA), was then washed with acetone, and was then dissolved in an electrophoretic buffer, so that the protein in the culture supernatant was concentrated. Separately, an intracellular protein was extracted as follows. 1 mL of the culture solution was mixed with 4 mL of PBS, and the mixed solution was then centrifuged at 12,000 rpm for 5 minutes at 4° C., and a supernatant was then removed. 5 mL of PBS was added to suspend this precipitate, and the obtained mixture was then centrifuged to remove a supernatant. This operation was carried out twice. PBS was added to the cells after completion of washing, to a total amount of 1 mL, and thereafter, the cells were disrupted by an ultrasonic treatment. After the disrupted cells had been centrifuged, a supernatant was recovered. The supernatant was designated as an intracellular extract. The above described culture supernatant concentrate (corresponding to 1 mL of the intracellular protein extract culture solution) was electrophoresed with Mini-PROTEAN TGX GEL 4-20% (manufactured by Bio-Rad). The resultant was transferred on a PVDF membrane (manufactured by Invitrogen, iBlot Transfer Stacks), using iBlot Transfer Device (manufactured by Invitrogen). After completion of blotting, the membrane was blocked, and it was then treated with Anti-His antibody (manufactured by GE Healthcare) used as a primary antibody and then with anti-mouse Ab-HRP (manufactured by GE Healthcare) used as a secondary antibody. Thereafter, luminescence was produced using Western Lightning Ultra (manufactured by Perkin Elmer). This resultant was analyzed using an imaging analyzer (Fluor S Max, manufactured by Bio-Rad). As a result, secretion was observed in three types of bacteria (*B. longum* 105A/pHuSP3L22-Trastuzumab scFv; *B. longum* 105A/pHuSP27L0-Trastuzumab scFv; and *B. longum* 105A/pHuSP27L6-Trastuzumab scFv) (FIG. 5). The results of Western blotting on *B. longum* 105A/pHuSP27L6-Trastuzumab scFv and *B. longum* 105A/pHuSP3L22-Trastuzumab scFv are shown in FIG. 6. A band was detected around the size of Trastuzumab scFv (approximately 25 kDa).

12. SDS-PAGE of Product Purified from Bifidobacteria Culture Supernatant

A streaked culture of recombinant bifidobacteria (*Bifidobacterium longum* 105A) that express secretory Trastuzumab scFv was inoculated into an APS-2S-2.5SE (75 µg/mL, spectinomycin) liquid medium, and it was then subjected to an anaerobic culture at 37° C. for 24 hours (activated culture solution). Subsequently, 0.5% activated culture solution was inoculated in a medium prepared by adding spectinomycin to a DMEM (low glucose, pyruvic acid, and HEPES) culture medium for cell culture (manufactured by Life Technologies cat #12320-032): APS-2S-2.5SE (=9:1) to a concentration of 75 µg/mL. The thus obtained mixture was subjected to an anaerobic culture at 37° C. for 16 hours. After the culture solution had been centrifuged, ammonium sulfate (for enzyme purification, manufactured by Wako Pure Chemical Industries, Ltd.) was added to the culture supernatant, resulting in 80% saturated solution, and the solution was then stirred at 4° C. overnight. After the reaction solution had been centrifuged, 1×PBS buffer (pH 7.4) was added to the precipitate to dissolve it in the buffer. The thus obtained solution was purified using a histidine tag protein purification kit (TALON Metal Affinity Resin, manufactured by TAKARA BIO INC.). The purified solution was concentrated by ultrafiltration (Amicon Ultra 10K, manufactured by Merck Millipore). Into the concentrated protein solution, an equal amount of 2×SDS sample buffer was mixed, and the obtained mixture was then heated at 95° C. for 3 minutes. This reaction mixture was defined as a sample for SDS-PAGE. The above described sample was electrophoresed in 1×SDS buffer, using Mini-PROTEAN TGX GEL (4%-20%, manufactured by BIO-RAD). After completion of the electrophoresis, the gel was washed with water, was then stained with a staining solution (SimplyBlue™ SafeStain), and was then destained with water. The results are shown in FIG. 7. In SP27L0 having no linkers, a band was not detected around the size of Trastuzumab scFv (approximately 25 kDa) (the arrow in the upper case in the figure), but in SP27L6 and SP3L22 into which a linker has been incorporated, a band with the estimated size of Trastuzumab scFv was detected (FIG. 7).

13. Analysis of Purified Protein by LC-MS/MS

Recombinant bifidobacteria, B. longum 105A/pHuSP27L6-scFv, was cultured, and a culture supernatant was then purified using a histidine tag-fused protein purification kit (TALON Metal Affinity Resin, manufactured by TAKARA BIO INC.). The purified protein was electrophoresed on 4%-20% polyacrylamide gel (Mini-PROTEAN TGX GEL, manufactured by Bio-Rad) and was then stained with Simply Blue Stain (manufactured by Invitrogen), and a band was cut out. A band was cut out of the stained gel to make a gel cube with a size of 1×1 mm$^3$, and the gel was then distained using destaining solution (an aqueous solution containing 30% acetonitrile (manufactured by Wako Pure Chemical Industries, Ltd.) and 25 mM ammonium bicarbonate (manufactured by SIGMA)), and was then reduced by 10 mM DTT ((±)-dithiothreitol, manufactured by Wako Pure Chemical Industries, Ltd.) (56° C., 45 min). Thereafter, it was subjected to air cooling to a room temperature, and was then alkylated with 55 mM ICH$_2$CONH$_2$ (iodoacetoamide, manufactured by Wako Pure Chemical Industries, Ltd.) (at room temperature under light-shielding conditions for 30 min). After completion of the alkylation, in-gel digestion (37° C., 16 h) was carried out using 12.5 ng/mL trypsin (manufactured by Promega), and the digested peptide fragment was extracted from the gel and was then concentrated (Reference: Shevchenko A. et al. Anal. Chem. 68, 850-858, 1996.). The obtained peptide fragment was analyzed by LC-MS/MS (Waters nano ACQUITY UPLC, manufactured by Xevo QTOF), and the identified peptide was compared with the amino acid sequence of Trastuzumab scFv (FIG. 8). As a result of the LC-MS/MS analysis, peptide fragments matched with the amino acid sequence of Trastuzumab scFv are shown in FIG. 9.

14. Construction of Recombinant Vector (puc119 Plasmid) and Production of Trastuzumab scFv DNA, which had been artificially synthesized based on the Trastuzumab cDNA sequence obtained from the PDB database as in the aforementioned case, was incorporated into a pUC119 plasmid to produce a vector, and the thus produced vector was used as a Trastuzumab scFv expression vector. A Trastuzumab-scFv-His plasmid was introduced into Rosetta2 E. coli (Merck Millipore, Darmstadt, Germany), and colonies were then selected using agar containing ampicillin and chloramphenicol. The colonies were allowed to grow at 37° C. in 10 mL of ampicillin-containing LB medium that comprised 2% glucose. Thereafter, the colonies were transferred into 200 mL of LB medium containing IPTG, and the culture was continuously carried out at 25° C. for 20 hours. Thereafter, E. coli was recovered, and a cell lysate was then extracted with BugBuster Protein Extraction Reagent (manufactured by Novagen) containing benzonuclease. After that, the cell lysate was centrifuged at 10000×g for 5 minutes, so that a supernatant containing an antibody protein was recovered. The His tag-attached antibody protein was purified using HisTrap HP Ni Sepharose column and Sephadex G25 gel filtration. After completion of the purification, SDS-PAGE was carried out using Tris-Glycine gel, and as a result, a band of Trastuzumab scFv that was matched with 30 kDa was detected (FIG. 10). The purified scFv antibody was used in flow cytometry or a surface plasmon resonance (SPR) assay using Biacore.

15. Measurement of Affinity of Trastuzumab scFv with HER2 Extracellular Domain By Biacore X100 Using Surface Plasmon Resonance (SPR) Method Trastuzumab scFv produced using E. coli Rosetta2 strain was used, and also, a HER2 extracellular domain protein (HER2. ex.) and a Trastuzumab full-body antibody, which had been produced using an insect-derived HF cell line, were used. An SPR analysis was carried out using Biacore X100. All of reagents and sensor chips used in the measurement were purchased from GE Healthcare. For immobilization of HER2. ex. on a CM5 sensor chip, a 10 mM acetate solution with pH 5.0 was used, and for immobilization of a Trastuzumab full-body antibody thereon, the solution with pH 5.5 was used. The measurement was carried out using a 0.05% or 0.005% Tween-PBS buffer (pH 7.4) at a flow rate of 30 µL/mL at 25° C. The binding affinity of Trastuzumab scFv with an antigen was obtained by two methods, namely, a multi-cycle method, which comprises observing the interaction of the added Trastuzumab scFv with HER2. ex. immobilized on the sensor chip, then completely removing the bound Trastuzumab scFv with a regeneration solution, then repeating the same measurement as described above even on Trastuzumab scFv with a different concentration, and comprehensively analyzing the obtained results; and a single cycle method capable of obtaining information necessary for analysis only by successively adding Trastuzumab scFv with 5 different concentrations during a single measurement cycle, wherein the removal of Trastuzumab scFv binding to HER2. ex. is not required. Dynamic constants regarding binding and dissociation were calculated using Biacore X100 evaluation software. The results of analyses are shown in FIG. 11.

16. Measurement of Affinity of Anti-HER2/neu Antibody with HER2 Extracellular Domain by Biacore X100 using a Surface Plasmon Resonance (SPR) Method As described above, using Trastuzumab full-body antibody on an immobilized side and HER2. ex. on a flow channel side, the binding affinity of a Trastuzumab full-body antibody with a HER2 antigen was analyzed according to a single cycle method employing Biacore X100. The obtained results were compared with the binding affinity of the produced Trastuzumab scFv. For the sake of convenience, since HER2. ex. was used on an immobilization side and Trastuzumab scFv was used on a flow channel side in the analysis of Trastuzumab scFv, the relationship between the flow channel and the immobilization became opposite to the case of the analysis of a Trastuzumab full-body antibody (FIG. 12). As a result, it was found that the produced Trastuzumab scFv has binding affinity equivalent to that of the Trastuzumab full-body antibody. Moreover, from the ka value (the larger the ka value, the higher the affinity with an antigen) and the kd value (the smaller the kd value, the stronger the binding ability with an antigen) used as reaction rate constants, it was demonstrated that the produced Trastuzumab scFv has higher affinity with an antigen than the Trastuzumab full-body antibody, but that the binding ability thereof with an antigen is low.

17. FACS Analysis of Binding Ability of Trastuzumab scFv and Trastuzumab Full-body Antibody to Human Breast Cancer Cell Lines As human breast cancer cell lines, a HER2-positive line (SKBR-3) and a HER2-negative line (MDA-MD231, 468) were used. As an anti-His antibody used for FACS, a PE-labeled anti-His antibody (CAT. 130-092-691, manufactured by Miltenyi) was used. In addition, as a control of Trastuzumab scFv, human CMVpp65 scFv was used. Regarding reagents, PBS(−)+0.1% BSA+0.1% sodium azide was used as an Ab buffer, PBS(−)+1% FBS+0.1% sodium azide+2 mM EDTA was used as a FACS buffer, and FACS buffer+0.5% PFA (paraform aldehyde) was used as a fixation buffer. Trastuzumab scFv and human CMVpp65 scFv were each adjusted to give a concentration of 10 μg/mL. As a secondary antibody, a PE-anti-His antibody was used.

1 to $2 \times 10^5$/well cells were suspended in the FACS buffer, and the obtained suspension was then seeded on a 96-well round-bottom plate. The plate was centrifuged at 1400 rpm for 2 minutes, and a supernatant was then aspirated. 10 μL of the Ab buffer was added to and suspended in the reaction solution, and thereafter, 10 μL of Trastuzumab scFv or human CMVpp65 scFv (10 μg/mL) used as a control was added thereto. The obtained mixture was incubated at 4° C. for 15 minutes, and the reaction solution was then washed with 150 μL of the FACS buffer twice. The reaction solution was centrifuged at 1400 rpm for 4 minutes, and a supernatant was then removed by aspiration. 10 μL of the Ab buffer was added to the resulting solution, 10 μL of the PE-anti-His antibody (not diluted) was further added thereto, and the obtained mixture was incubated at 4° C. for 15 minutes. The reaction solution was washed with 150 μL of the FACS buffer twice, and was then centrifuged at 1400 rpm for 2 minutes, and thereafter, a supernatant was aspirated. 400 μL of the fixation buffer was added to the resulting solution, and the obtained solution was transferred into a FACS tube by pipetting. Thereafter, the measurement was carried out using Flow Cytometry (FACSCanto, manufactured by BD Biosciences) within 24 hours. The results are shown in FIG. 13. It was demonstrated that Trastuzumab scFv is an antibody that is sufficiently separable from negative control cells, although it is slightly inferior to a full-body antibody thereof (FIG. 13, center and right). Moreover, it was also demonstrated that Trastuzumab scFv specifically binds to an antigen, from the comparison with anti-cytomegalovirus antigen scFv as a control, in which a HER2 antigen expressed by SKBR-3 cells cannot be detected (FIG. 13, left).

18. In Vivo Dynamic Imaging of Cy5.5-Labeled Trastuzumab scFv using In Vivo Tumor Models A human mammary tumor cell line MDA-MB-361 ($5 \times 10^6$ cells/mouse [containing Matrigel]), which highly expresses a HER2 antigen, was transplanted into the mammary epithelium of a BALB/cA-nu/nu mouse (female, 7-week-old, manufactured by CLEA Japan, Inc.) that immunologically deleted T cell function. To the MDA-MB-361 cancer-bearing mouse (single mouse) whose tumor volume had reached approximately 290 mm³, fluorochrome Cy5.5-labeled Trastuzumab scFv (corresponding to 3.75 mg/kg) was intratumorally administered once (100 μL). In order to confirm the retention of the Cy5.5-labeled Trastuzumab scFv in the tumor according to intratumoral administration, the mouse was measured under isoflurane inhalation anesthesia for 1 week, using in vivo imaging device eXplore Optix (manufactured by GE Healthcare) (FIG. 14). On the first week, the mouse was sacrificed by euthanasia, the tumor, liver, spleen, lung and small intestine were then excised from the mouse, and imaging ability was then measured. As a result, it was demonstrated that the Cy5.5-labeled Trastuzumab scFv can be detected even on the 7th day after intratumoral administration thereof.

19. In Vivo Dynamic Imaging of Cy5.5-labeled Trastuzumab Full-Body Antibody using In Vivo Tumor Models As described above, using a cancer-bearing nude mouse system, into the mammary epithelium of which $4 \times 10^6$ cells/mouse MDA-MB-361 was transplanted, in order to confirm the retention of the Cy5.5-labeled Trastuzumab full-body antibody in the tumor according to intratumoral administration, a Cy5.5-labeled Trastuzumab full-body antibody (corresponding to 3.75 mg/kg) was intratumorally administered to a cancer-bearing mouse (400 mm³) on the 56th day after the transplantation. Intratumoral retention was measured until 5th day after the administration, under isoflurane inhalation anesthesia, using eXplore Optix (FIG. 15). Even 5 days after the intratumoral administration, the fluorescence-labeled antibody could be observed in the living body of the mouse. Thus, it was demonstrated that the Cy5.5-labeled Trastuzumab full-body antibody can be detected for a long period of time, as in the case of the Cy5.5-labeled Trastuzumab scFv.

20. Antitumor Effect of Trastuzumab scFv on Orthotropic Grafted Tumor of Human Breast Cancer MDA-MB-361 Cells A human mammary tumor cell line MDA-MB-361 ($5 \times 10^6$ cells/mouse [containing Matrigel]) highly expressing a HER2 antigen was transplanted into the mammary epithelium of the aforementioned BALB/cA-nu/nu mouse (n=4 to 5/group). To the MDA-MB-361 cancer-bearing mice whose mean tumor volume had reached 250 mm³, Trastuzumab scFv (corresponding to 3.75 mg/kg) was intratumorally administered (50 μL) five times every other day. The tumor volume was measured over time, after initiation of the administration of Trastuzumab scFv, and the antitumor activity thereof was compared with the antitumor activity in a non-treated group (control group). From the results obtained using the tumor volume measured every 3 or 4 days as an indicator, it was demonstrated that Trastuzumab scFv has a distinct antiproliferative effect on the tumor cells (FIG. 16).

Example 2

21. Production of Secretion Plasmid (pHuSP7L20-opt-Trastuzumab scFv) Optimized to Codon of Bifidobacteria The nucleotide sequence of a Trastuzumab scFv gene was optimized to the codon of bifidobacteria (opt-Trastuzumab scFv gene: SEQ ID NO: 92). Moreover, a secretion plasmid (pHuSP7L20-opt-Trastuzumab scFv: SEQ ID NO: 94), into which the opt-Trastuzumab scFv gene was incorporated, was produced.

The opt-Trastuzumab scFv gene was artificially synthesized as a plasmid pUC57-opt-Trastuzumab scFv subcloned into a plasmid pUC57 for *E. coli* (manufactured by GenScript Japan Inc.). As a first stage, a Trastuzumab scFv gene of pHuSP27L0-Trastuzumab scFv (SEQ ID NO: 93) that was an existing Trastuzumab scFv expression-secretion plasmid was replaced by an opt-Trastuzumab scFv gene, so as to produce a plasmid pHuSP27L0-opt-Trastuzumab scFv. As a second stage, SP27L0 that was a signal peptide+a linker sequence was replaced by SP7L20, so as to produce pHuSP7L20-opt-Trastuzumab scFv (SEQ ID NO: 94). As a third stage, the Hu promoter of pHuSP7L20-opt-Trastuzumab scFv was replaced by a P30 promoter, so as to produce pP30SP7L20-opt-Trastuzumab scFv (SEQ ID NO: 95). The details are as follows.

22. Preparation of Insert in Production of pHuSP27L0-opt-Trastuzumab ScFv

The procedures for replacing the Trastuzumab scFv gene portion of pHuSP27L0-Trastuzumab scFv with an opt-Trastuzumab scFv gene will be described below. First, an opt-Trastuzumab scFv insert was prepared as follows. Using a plasmid pUC57-opt-Trastuzumab scFv having an opt-Trastuzumab scFv-coding sequence (containing a His-tag sequence at the terminus thereof) as a template, PCR was carried out. Using, as primers, opt-Trastuzumab scFv_ins_INF_F1 primer (SEQ ID NO: 96) and opt-Trastuzumab scFv_ins_INF_R1 primer (SEQ ID NO: 97) (wherein 15 nucleotides on the 5'-terminal side of each primer have a sequence homologous to a vector as shown below), an opt-Trastuzumab scFv-coding region was amplified to obtain a 777-bp insert PCR product. Using 2.0% agarose gel (1×TEB buffer, containing ethidium bromide), the insert PCR product, together with a DNA concentration marker, was subjected to electrophoresis, so that the concentration was estimated.

23. Preparation of Vector in Production of pHuSP27L0-opt-Trastuzumab ScFv

A vector was prepared as follows. Using, as a template, pHuSP27L0-Trastuzumab scFv (comprising a Trastuzumab scFv gene, a replication origin of *E. coli*, a replication origin of bifidobacteria, and a spectinomycin resistance gene), PCR was carried out. Using, as primers, SP1_Vec_F1 primer (SEQ ID NO: 98) and d0018_0aa_Vec_R3 primer (SEQ ID NO: 99), a region from which the Trastuzumab scFv gene was excluded was amplified, so as to obtain an approximately 4-kb vector PCR product (PrimeSTAR; registered trademark: HS Premix, manufactured by TAKARA BIO INC.). Using 0.8% agarose gel (1×TEB buffer, containing ethidium bromide), the vector PCR product, together with a DNA concentration marker, was subjected to electrophoresis, so that the concentration was estimated.

24. Fusing of Insert to Vector by In-Fusion Reaction in Production of pHuSP27L0-opt-Trastuzumab scFv Using In-Fusion (registered trademark) HD Cloning Kit with Cloning Enhancer (manufactured by Clontech), the insert PCR product was fused to the vector PCR product. First, referring to the website of Clontech, In-Fusion (registered trademark) Molar Ratio Calculator (http://bioinfo.clontech.com/infusion/molarRatio.do), necessary amounts of the insert and the vector were calculated. 2 µL of 5×In-Fusion HD Enzymes premix, 1 µL of Cloning Enhancer, and necessary amounts of the insert and the vector were mixed with one another, and sterilized water was then added to the obtained mixture, so that a total amount of the reaction system was adjusted to 10 µL. After completion of a reaction at 37° C. for 15 minutes, the reaction product was treated at 50° C. for 15 minutes and was then left at rest at 4° C.

25. Transformation of *E. coli*, Plasmid Extraction and Sequencing in Production of pHuSP27L0-opt-Trastuzumab scFv Using 2 µL of In-Fusion reaction solution, *E. coli* HST16CR Competent Cells (manufactured by TAKARA BIO INC.) were transformed, and the resultant was then transferred onto an LB (75 µg/mL, containing spectinomycin) plate, followed by performing a culture at 37° C. overnight. Conditions for the transformation were as described in the product instruction. The transformed *E. coli* colonies were cultured in an LB (75 µg/mL, containing spectinomycin) liquid medium at 37° C. overnight, and a plasmid was then extracted from the culture (QIAprep Spin Miniprep Kit, manufactured by QIAGEN). It was confirmed that the whole nucleotide sequence of this plasmid was as designed, and the plasmid was designated as a plasmid pHuSP27L0-opt-Trastuzumab scFv.

26. Preparation of Insert in Production of pHuSP7L20-opt-Trastuzumab scFv

The procedures for replacing the signal peptide+linker sequence (SP27L0) of pHuSP27L0-opt-Trastuzumab scFv with SP7L20 will be described below. First, using the genomic DNA of *Bifidobacterium longum* 105A as a template, PCR was carried out, and a signal peptide insert was prepared as follows. Using SP7L20-opt-Trastuzumab scFv_ins_INF_F1 primer (SEQ ID NO: 100) and SP7L20-opt-Trastuzumab scFv_ins_INF_R1 primer (SEQ ID NO: 101) (wherein 15 nucleotides on the 5'-terminal side of each primer have a sequence homologous to a vector as shown below), PCR was carried out, so as to obtain a 189-bp insert PCR product (SP7L20). Using 2.0% agarose gel, the insert PCR product, together with a DNA concentration marker, was subjected to electrophoresis, so that the concentration was estimated.

27. Preparation of Vector in Production of pHuSP7L20-opt-Trastuzumab scFv

Using the plasmid pHuSP27L0-opt-Trastuzumab scFv as a template, PCR was carried out to prepare a vector. Using, as primers, Hu-opt-Trastuzumab_vec_F1 primer (SEQ ID NO: 102) and Hu-Vec_R1 primer (SEQ ID NO: 18), a region from which the signal peptide+linker portion was excluded was amplified, so as to obtain an approximately 4.5-kb vector PCR product. Using 0.8% agarose gel, the vector PCR product, together with a DNA concentration marker, was subjected to electrophoresis, so that the concentration was estimated.

28. Fusing of Insert to Vector by In-Fusion Reaction in Production of pHuSP7L20-opt-Trastuzumab scFv As described above, using In-Fusion (registered trademark) HD Cloning Kit with Cloning Enhancer (manufactured by Clontech), an insert PCR product was fused to a vector PCR product.

29. Transformation of *E. coli*, Plasmid Extraction and Sequencing in Production of pHuSP7L20-opt-Trastuzumab scFv As described above, using In-Fusion reaction solution, transformation of *E. coli* HST16CR Competent Cells, culture, and plasmid extraction were carried out. Thereafter, it was confirmed that the nucleotide sequence of an opt-Trastuzumab scFv expression cassette (from the Hu promoter to the terminator) of this plasmid was as designed.

30. Preparation of Insert in Production of pP30SP7L20-opt-Trastuzumab scFv

The promoter of pHuSP7L20-opt-Trastuzumab scFv was replaced by the P30 promoter of a gene existing in the genome of *B. longum* 105A.

First, using the genomic DNA of *B. longum* 105A as a template, PCR was carried out, and a signal peptide insert was prepared as follows. Using P30_ins_F1 primer (SEQ ID NO: 103) and P30_SP7_ins_R1 primer (SEQ ID NO: 104) (wherein 15 nucleotides on the 5'-terminal side of each primer have a sequence homologous to a vector as shown below), PCR was carried out to obtain a 265-bp insert PCR product. Using 2.0% agarose gel, the insert PCR product, together with a DNA concentration marker, was subjected to electrophoresis, so that the concentration was estimated.

31. Preparation of Vector in Production of pP30SP7L20-opt-Trastuzumab scFv

Using the plasmid pHuSP7L20-opt-Trastuzumab scFv as a template, PCR was carried out to prepare a vector. Using, as primers, SP7_Vec_F1 primer (SEQ ID NO: 105) and pUC_ori_Vec_R2 primer (SEQ ID NO: 106), the region of the opt-Trastuzumab scFv expression unit, from which a promoter was excluded, was amplified to obtain an approximately 4.4-kb vector PCR product. Using 0.8% agarose gel, the vector PCR product, together with a DNA concentration marker, was subjected to electrophoresis, so that the concentration was estimated.

32. Fusing of Insert to Vector by In-Fusion Reaction in Production of pP30SP7L20-opt-Trastuzumab scFv As described above, using In-Fusion (registered trademark) HD Cloning Kit with Cloning Enhancer (manufactured by Clontech), an insert PCR product was fused to a vector PCR product.

33. Transformation of E. coli, Plasmid Extraction and Sequencing in Production of pP30SP7L20-opt-Trastuzumab scFv By the same operations as those described above, transformation of E. coli HST16CR Competent Cells, culture, and plasmid extraction were carried out using In-Fusion reaction solution. Thereafter, it was confirmed that the nucleotide sequence of an opt-Trastuzumab scFv expression cassette (from the P30 promoter to the terminator) of this plasmid was as designed.

34. Transformation of Bifidobacteria

Using the plasmids pHuSP7L20-opt-Trastuzumab scFv and pP30SP7L20-opt-Trastuzumab scFv, bifidobacteria were transformed as follows. Using the plasmid DNA, bifidobacteria, B. longum 105A, was transformed according to an electroporation system (Gene Pulser II, manufactured by Bio-Rad Laboratories). After completion of the electric shock, a mixed solution of 800 µL of IMR liquid medium and 50 µL of vitamin C-added solution was immediately added to a cuvette, and it was then recovered into a 2-mL sterilized microtube. The same operations as described above were carried out on each tube, and the cap of each 2-mL tube was then loosened. The resulting solution, together with AneroPack, was placed in a hermetically sealed vessel, it was then placed in an incubator that had been set at 37° C., and it was then incubated for 3 hours. After completion of the incubation, each suspension was fully mixed, and 100 µL of the mixed suspension was taken and was then each applied to one IMR agar medium (containing 75 µg/mL SPCM). Such an agar medium, together with a deoxidant/carbon dioxide generator (AneroPack-Kenki, manufactured by Mitsubishi Gas Chemical Company), was placed in a hermetically sealed vessel, and was then cultured in an incubator that had been set at 37° C. for 2 to 3 days. The colonies growing on the plate were picked up with a disposable stick, and were then streaked on a BL-bS agar medium (containing 75 µg/mL SPCM). The medium, together with a deoxidant/carbon dioxide generator (AneroPack-Kenki, manufactured by Mitsubishi Gas Chemical Company), was placed in a hermetically sealed vessel, and was then cultured in an incubator that had been set at 37° C. for 1 day, so as to obtain a streaked culture, thereby obtaining recombinant bifidobacteria, B. longum 105A/pHuSP7L20-opt-Trastuzumab scFv and B. longum 105A/pP30SP7L20-opt-Trastuzumab scFv.

35. Purification of Trastuzumab scFv from bifidobacteria

Trastuzumab scFv was purified using the above-produced Trastuzumab scFv secretion bifidobacteria, B. longum 105A/pHuSP7L20-opt-Trastuzumab scFv.

B. longum 105A/pHuSP7L20-opt-Trastuzumab scFv was inoculated into APS-2S-2.5SE medium (containing 75 µg/mL spectinomycin), and it was then subjected to an anaerobic culture at 37° C. for 24 hours. Subsequently, 0.5% of this culture solution was added to a medium prepared by adding spectinomycin to DMEM: APS-2S-2.5SE (=9:1) to a concentration of 75 µg/mL. The thus obtained mixture was subjected to an anaerobic culture at 37° C. for 18 hours.

While a culture supernatant obtained by centrifugation of the above described culture solution was stirred, ammonium sulfate was slowly added to the culture supernatant to 80% saturation. The obtained mixture was stirred at 4° C. overnight so as to conduct salting-out. The resultant was centrifuged, and thereafter, a precipitate was recovered and was then purified by employing a histidine tag-added protein purification kit (TALON resin, manufactured by TAKARA BIO INC.), using a histidine tag as an indicator. The thus purified solution was concentrated by ultrafiltration (Amicon Ultra-0.5, manufactured by Merck Millipore).

SDS-PAGE was performed on a part of the above-purified single-chain antibody, and thereafter, Coomassie Blue staining (manufactured by Life Technologies, SimplyBlue™ SafeStain) was carried out thereon, so that it was confirmed that Trastuzumab scFv was purified at a purity of approximately 90%. The concentration of the purified protein was measured by a Bradford method (Coomassie Plus Protein Assay, manufactured by Thermo Scientific).

The results of the SDS-PAGE analysis are shown in FIG. 17. A band was detected around the size of Trastuzumab scFv (approximately 25 kDa).

36. Confirmation of Binding of Trastuzumab scFv to Human Breast Cancer Cell Lines by Fluorescent Antibody Technique Using Trastuzumab scFv purified from B. longum 105A/pHuSP7L20-opt-Trastuzumab scFv, the binding of the Trastuzumab scFv to human breast cancer cell lines was confirmed.

As human breast cancer cell lines, HER2-positive lines (SK-BR-3 and BT-474) and a HER2-negative line (SK-MEL-28) were used (all of which were purchased from American Type Culture Collection, ATCC). As an anti-His antibody for immunostaining, an Alexa Fluor 488-labeled anti-His antibody (Cat. D291-A48, manufactured by MEDICAL & BIOLOGICAL LABORATORIES CO., LTD.) was used. In addition, an anti-HER2 full-body antibody (Cat. 427041, manufactured by NICHIREI BIOSCIENCE INC.) was added, so that the expression of HER2 in the cells was confirmed. Regarding reagents, PBS(−) was used as a wash buffer, PBS(−)+1.5% BSA was used as an Ab buffer, and 4% PFA (paraformaldehyde)+phosphate buffer (manufactured by Wako Pure Chemical Industries, Ltd.) was used as a fixation buffer. Trastuzumab scFv and an anti-HER2 full-body antibody were prepared to a concentration of 5 µg/mL by addition of the Ab buffer. As a secondary antibody against Trastuzumab scFv, Anti-His-tag mAb-Alexa Fluor 488 was used, and as a secondary antibody against an anti-HER2 full-body antibody, DyLight 594 goat anti-mouse IgG (Cat. 405311, manufactured by BioLegend) was used. As a mounting agent, VECTASHIELD Mounting Medium with DAPI (Cat. H-1200, manufactured by VECTOR Laboratories) was used.

A cover glass with a size of 18 mm×18 mm (manufactured by Matsunami Glass Ind., Ltd.) was placed on a 6-well plate (manufactured by NEST), and it was then coated with Poly-L-lysine (manufactured by Sigma-Aldrich). Thereafter, the cells were cultured thereon at a density of 1 to $2\times10^4$ cells/glass. One day later, the plate was left at rest on ice, and the medium was aspirated and cells were then washed with a wash buffer three times. Thereafter, 100 μL of the Ab buffer was added to the cells, and the obtained mixture was then incubated on ice for 30 minutes. Thereafter, 100 μL of Trastuzumab scFv, or an Ab buffer used as a negative control, was added, and the obtained mixture was incubated on ice for 1 hour. After completion of a scFv reaction, the resultant was washed with a wash buffer three times. After completion of the washing, 100 μL of Anti-His-tag mAb-Alexa Fluor 488 (400-fold diluted) was added to the resultant, and the obtained mixture was then incubated on ice for 30 minutes. After completion of the incubation, the reaction product was washed with a wash buffer three times, 500 μL of the fixation buffer was then added to the resultant, and the obtained mixture was then incubated on ice for 10 minutes. Thereafter, the reaction product was washed with a wash buffer three times, and was then mounted with a DAPI-containing mounting agent, followed by observation under a fluorescence microscope (DM5000B, manufactured by Leica MICROSYSTEMS).

The results are shown in FIG. 18. It was confirmed that HER2 was expressed in HER2-positive cells, and that HER2 was not expressed in HER2-negative cells. Furthermore, it was also demonstrated that Trastuzumab scFv specifically binds to HER2-positive cells and is co-localized with HER2 on the cell surface.

37. Confirmation of Binding of Trastuzumab scFv to Human Breast Cancer Cell Lines by Flow Cytometry Using Trastuzumab scFv purified from *B. longum* 105A/pHuSP7L20-opt-Trastuzumab scFv, the binding of the Trastuzumab scFv to human breast cancer cell lines was confirmed.

BT-474 cells and SK-BR-3 cells, in which human HER2 was positive, and SK-MEL-28 cells in which human HER2 was negative (all of which were purchased from American Type Culture Collection, ATCC), were used. These cells were cultured in a 100-mm petri dish (manufactured by NIPPON Genetics Co, Ltd.). BT-474 cells were cultured in a Hybri-care medium, SK-BR-3 cells were cultured in a McCoy's 5A medium, and SK-MEL-28 cells were cultured in an E-MEM medium. Into all of these media, inactivated 10% fetal bovine serum (manufactured by EQUITECH-BIO) and penicillin/streptomycin solution (manufactured by COSMO BIO Co., Ltd.) were mixed.

At the stage in which the above described cells were gathered to a certain extent, the medium was removed, and the cells were washed with PBS(−) (manufactured by Wako Pure Chemical Industries, Ltd.). Thereafter, the cells were detached from the petri dish, using Trypsin-EDTA (manufactured by Life Technologies), and were then transferred into a 15-mL conical tube (manufactured by SANPLATEC CORP.). The cells were centrifuged at 1000 rpm for 5 minutes, using a desktop small centrifuge (manufactured by KUBOTA CO., LTD.), a supernatant was then removed, and 5 mL of medium was then added thereto. The number of cells contained in this cell suspension was counted using a hemocytometer, and the cells were then dispensed in a 1.5-mL tube (manufactured by Eppendorf) to a cell density of $3\times10^4$ cells/tube. The cells dispensed in the 1.5-mL tube were centrifuged at 5000 rpm at 4° C. for minute, using a trace-amount refrigerated centrifuge (manufactured by TOMY), and after completion of the centrifugation, a supernatant was removed. Cell pellets remaining in the tube were washed with 1 mL of PBS(−) twice, and 100 μL of the purified anti-HER2 scFv was added in a concentration of 10 μg/mL thereto. It was then left at rest on ice for 30 minutes. To the reaction product, 20 μL of a fluorescence-labeled anti-His-tag antibody (Anti-His-tag Alexa Fluor 488, manufactured by MEDICAL & BIOLOGICAL LABORATORIES CO., LTD.) was added, and the obtained mixture was fully mixed by pipetting. The reaction mixture was then left at rest on ice for 20 minutes. After leaving at rest, 500 μL of FACS buffer (PBS containing 1% BSA and 0.1% $NaN_3$) was added to the tube, and the cells were then suspended therein. The obtained mixture was centrifuged at 5000 rpm at 4° C. for 1 minute, using a trace-amount refrigerated centrifuge, and a supernatant was then removed. This washing operation was carried out again, and 500 μL of FACS buffer was added to the tube to suspend the cells therein. Thereafter, the cells were transferred into a 5-mL polystyrene round-bottom tube (manufactured by Becton, Dickinson and Company).

Immediately before performing an analysis, 5 μL of a propidium iodide solution (5 μg/mL) was added to the tube, and thereafter, an analysis was carried out using a BD FACS cantoII flow cytometer (manufactured by Becton, Dickinson and Company) and flow cytometric analysis software Kaluza ver 1.2 (manufactured by BECKMAN COULTER).

The results are shown in FIG. 19. In the upper case of FIG. 19, it was confirmed that Trastuzumab scFv binds to BT-474 cells and SK-BR-3 cells, which were both HER2-positive cells. On the other hand, in the lower case of FIG. 19, the binding of Trastuzumab scFv to SK-MEL-28 cells, which were HER2-negative cells, was not observed.

38. Antiproliferative Activity of Trastuzumab scFv Against Cancer Cells

With regard to the physiological activity of Trastuzumab scFv, Trastuzumab scFv obtained by His tag purification of a culture supernatant of *B. longum* 105A/pP30SP7L20-opt-Trastuzumab scFv (PBS replacement) was added to HER2-positive cells (BT474 (breast cancer) cells), and the antiproliferative activity was then measured.

BT474 cells were cultured in a McCoy's 5A medium (containing 10% (v/v) FBS) at 37° C. in 5% $CO_2$. Thereafter, the cells were seeded on a 96-well plate at a cell density of $1\times10^4$ cells/well, and were then cultured at 37° C. in 5% $CO_2$ for 24 hours. After completion of the culture, the medium was removed by aspiration, and 98 μL each of fresh McCoy's 5A medium (containing 10% (v/v) FBS) was added. Subsequently, 2 μL each of anti-Trastuzumab scFv in PBS(−) that was adjusted to 244 ng/mL to 1 mg/mL was added as a measurement sample. This plate was cultured at 37° C. in 5% $CO_2$ for 5 days.

After completion of the culture for 5 days, the medium was removed by aspiration, and 100 μL each of 1 mL of Cell Counting Kit-8 added to 9 mL of fresh McCoy's 5A medium (containing 10% (v/v) FBS) was added thereto. The obtained mixture was further incubated at 37° C. in 5% $CO_2$ for 3 hours, and the absorbance was then measured at wavelengths of 450 nm and 630 nm (reference wavelengths), so that the antiproliferative activity of Trastuzumab scFv against the above described HER2-positive cells was measured.

The results are shown in FIG. 20. It was confirmed that Trastuzumab scFv purified from *B. longum* 105A/pP30SP7L20-opt-Trastuzumab scFv exhibits a dose-dependent antiproliferative activity on BT474 breast cancer cells, and that Trastuzumab scFv has physiological activity.

39. Confirmation of antitumor effect of Trastuzumab scFv secretion bifidobacteria, *B. longum* 105A/pP30SP7L20-opt-Trastuzumab scFv Using cancer-bearing nude mice with the human stomach cancer cell line NCI-N87, the antitumor effect of *B. longum* 105A/pP30SP7L20-opt-Trastuzumab scFv was confirmed as follows.

The human stomach cancer cell line NCI-N87 (purchased from ATCC) was cultured in a RPMI1640 medium (manufactured by Wako Pure Chemical Industries, Ltd.), to which 10% FBS (manufactured by EQUITECH-BIO, INC.) had been added, and the cells were then transplanted into nude mice (manufactured by Japan SLC, Inc.) to produce cancer-bearing mice. For the experiment, cancer-bearing mice, the tumor volume of which had reached approximately 200 $mm^3$, were used. Constitution of groups is as follows: Group 1: a non-treated group (control group); Group 2: a B. longum 105A/pBEshuttle strain (Trastuzumab scFv-not-expressing bacteria) administration group; and Group 3: a *B. longum* 105A/pP30SP7L20-opt-Trastuzumab scFv (Trastuzumab scFv-expressing bacteria) administration group. Eight cancer-bearing mice were used for each group.

Bifidobacteria were administered to the mice through the caudal vein, at a dose of $6 \times 10^8$ cfu, twice a week. In addition, to the bifidobacteria administration groups (Group 2 and Group 3), 1 mL each of 10% maltose solution was administered to the mice at a frequency of twice a day, five times a week (administration for 5 days, then suspension for 2 days). The test period was set at 3 weeks, and tumor volume was measured over time. On the 22nd day, the tumor was excised, and was then used for Gram staining and immunohistostaining.

A change over time in tumor volume and the results regarding antitumor effect are shown in FIG. 21. The tumor volume in the *B. longum* 105A/pP30SP7L20-opt-Trastuzumab scFv administration group transited at a level lower than other groups throughout the test period. At the time of termination of the test (Day 22), the tumor volume in the *B. longum* 105A/pP30SP7L20-opt-Trastuzumab scFv administration group was significantly reduced in comparison to that in the *B. longum* 105A/pBEshuttle administration group, and *B. longum* 105A/pP30SP7L20-opt-Trastuzumab scFv was confirmed to have an antitumor effect.

40. Confirmation of the presence of *B. longum* 105A/pP30SP7L20-opt-Trastuzumab scFv in tumor, and detection of secreted Trastuzumab scFv Using the tumor excised in the above section 39, localization of the bacteria of genus *Bifidobacterium* in the tumor was confirmed by Gram staining, and localization of Trastuzumab scFv therein was confirmed by immunohistostaining using an anti-His-tag antibody.

The excised tumor was subjected to frozen embedding using O.C.T. compound (manufactured by Sakura Finetek Japan Co., Ltd.), and then, thin slide specimens were produced using freezing microtome Leica CM1900 (manufactured by Leica) and were then subjected to each histostaining.

The procedures for Gram staining will be described below. The above described thin slide specimen was air-dried, and was then immersed in 4% PFA (manufactured by Wako Pure Chemical Industries, Ltd.) for 10 minutes, so that it was fixed. After completion of the fixation, the specimen was pre-stained with Barmi M Crystal Violet Solution (manufactured by Muto Pure Chemicals Co., Ltd.) for 2 minutes, and was then treated with Barmi M Iodine-Sodium Hydroxide Solution (manufactured by Muto Pure Chemicals Co., Ltd.) for 1 minute. Thereafter, the specimen was discolored with Barmi M acetone-ethyl alcohol mixed solution (manufactured by Muto Pure Chemicals Co., Ltd.), and was then stained with Barmi M 0.1% fuchsin solution (manufactured by Muto Pure Chemicals Co., Ltd.) for 1 minute. After completion of the staining, the specimen was washed with purified water, was then dehydrated with 99.5% ethanol (manufactured by Wako Pure Chemical Industries, Ltd.), and was then dialyzed with Lemosol (manufactured by Wako Pure Chemical Industries, Ltd.). Thereafter, the specimen was mounted with Entellan new (manufactured by MERCK KGaA).

The results are shown in FIG. 22. As a result of the Gram staining, the presence of *B. longum* 105A/pBEshuttle and *B. longum* 105A/pP30SP7L20-opt-Trastuzumab scFv was confirmed in the tumor tissues (the arrow portion of FIG. 22).

The procedures for immunohistostaining using an anti-histidine tag antibody will be described below. The above described thin slide specimen was air-dried, and was then immersed in 4% PFA (manufactured by Wako Pure Chemical Industries, Ltd.) for approximately 4 hours, so that it was fixed. After completion of the fixation, the specimen was washed with purified water for 1 minute, and was then washed with 1×PBS(−) for 5 minutes three times. Water around the tissues was wiped off, and the tissues were then enclosed with Dako pen (manufactured by Dako). Thereafter, 3% BSA-PBS was added dropwise to the tissues, and the reaction was carried out for 60 minutes, so that non-specific bindings were inhibited. Anti-His-tag mAb-Alexa Fluor (registered trademark) 594 (manufactured by MBL) was mixed and diluted with Can Get Signal (registered trademark) immunostain (manufactured by TOYOBO), and the mixed solution was used as an antibody reaction solution and was added dropwise to the tissues. The reaction was carried out at 4° C. overnight. After completion of the antibody reaction, the tissues were washed with 1×PBS(−) for 5 minutes three times, and was then mounted with VECTASHIELD (registered trademark) Mounting Medium with DAPI. The stained section was subjected to microscopic examination under a microscope DM5000B (manufactured by Leica), and the image thereof was then photographed.

The results are shown in FIG. 23. As a result of the immunohistostaining for a histidine tag, a histidine tag-positive image (Trastuzumab scFv) was observed (the arrow portion of FIG. 23).

As a result of the Gram staining and the immunohistostaining, it was confirmed that, when *B. longum* 105A/pP30SP7L20-opt-Trastuzumab scFv is intravenously administered to human stomach cancer NCI-N87-bearing mice, it is engrafted in the tumor, and also that Trastuzumab scFv secreted from *B. longum* 105A/pP30SP7L20-opt-Trastuzumab scFv is present in the tumor.

INDUSTRIAL APPLICABILITY

The vector of the present invention or intestinal bacteria transformed with the vector can efficiently supply a therapeutic agent to the diseased site in anaerobic diseased tissues, when compared with conventional ones. Accordingly, the vector of the present invention or intestinal bacteria transformed with the vector is useful in the field of pharmaceutical products or therapeutic field.

The invention claimed is:

1. A DNA insert, wherein the 5'-terminus of an antibody gene is linked to the 3'-terminus of a DNA encoding a signal peptide consisting of an amino acid sequence described in SEQ ID NO: 1 or SEQ ID NO: 107.

2. The DNA insert according to claim 1, wherein the antibody gene is the gene of an antibody having an anticancer activity.

3. The DNA insert according to claim 2, wherein the antibody having an anticancer activity is Trastuzumab.

4. The DNA insert according to claim 3, wherein the Trastuzumab is a Trastuzumab single-chain antibody.

5. The DNA insert according to claim 1, wherein the DNA encoding a signal peptide consists of the nucleotide sequence shown in SEQ ID NO: 2 or SEQ ID NO: 108.

6. The DNA insert according to claim 1, wherein the 5'-terminus of an antibody gene is linked to the 3'-terminus of a DNA encoding a signal peptide consisting of an amino acid sequence described in SEQ ID NO: 1 or SEQ ID NO: 107, via a DNA encoding a linker peptide.

7. The DNA insert according to claim 6, wherein the antibody gene is a gene of an antibody having an anticancer activity.

8. The DNA insert according to claim 7, wherein the antibody having an anticancer activity is Trastuzumab.

9. The DNA insert according to claim 8, wherein the Trastuzumab is a Trastuzumab single-chain antibody.

* * * * *